US008546440B2

(12) United States Patent
Gijsen et al.

(10) Patent No.: US 8,546,440 B2
(45) Date of Patent: Oct. 1, 2013

(54) SUBSTITUTED BICYCLIC IMIDAZOLE DERIVATIVES AS GAMMA SECRETASE MODULATORS

(75) Inventors: Henricus Jacobus Maria Gijsen, Breda (BE); Gregor James MacDonald, Zoersel (BE); François Paul Bischoff, Vosselaar (BE); Gary John Tresadern, Toledo (ES); Andrés Avelino Trabanco-Suárez, Olias del Rey (ES); Sven Franciscus Anna Van Brandt, Nijlen (BE); Didier Jean-Claude Berthelot, Antwerpen (BE)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 48 days.

(21) Appl. No.: 13/133,027

(22) PCT Filed: Dec. 16, 2009

(86) PCT No.: PCT/EP2009/067321
§ 371 (c)(1),
(2), (4) Date: Jun. 6, 2011

(87) PCT Pub. No.: WO2010/070008
PCT Pub. Date: Jun. 24, 2010

(65) Prior Publication Data
US 2011/0237580 A1 Sep. 29, 2011

(30) Foreign Application Priority Data

Dec. 18, 2008 (EP) .................................... 08172202

(51) Int. Cl.
*A61K 31/5377* (2006.01)
*A61K 31/506* (2006.01)
*A61K 31/4439* (2006.01)
*A61K 31/4196* (2006.01)
*A61K 31/4188* (2006.01)
*C07D 487/04* (2006.01)

(52) U.S. Cl.
USPC ........ 514/393; 514/383; 514/338; 514/234.5; 514/256; 514/322; 544/139; 544/322; 546/199; 546/272.4; 546/273.4; 548/266.4; 548/302.7

(58) Field of Classification Search
USPC ........... 546/121, 199, 272.4, 273.4; 514/300, 514/383, 338, 393, 234.5, 256, 322; 544/139, 544/322; 548/266.4, 302.7
See application file for complete search history.

(56) References Cited

U.S. PATENT DOCUMENTS

| 7,923,563 | B2 | 4/2011 | Kushida et al. |
| 2002/0128319 | A1 | 9/2002 | Koo et al. |
| 2008/0280948 | A1 | 11/2008 | Baumann et al. |
| 2009/0062529 | A1 | 3/2009 | Kimura et al. |

FOREIGN PATENT DOCUMENTS

| EP | 1757591 A1 | 2/2007 |
| WO | WO 01/78721 A1 | 10/2001 |
| WO | WO 2004/017963 A1 | 3/2004 |
| WO | WO 2004/110350 A2 | 12/2004 |
| WO | WO 2005/085245 A1 | 9/2005 |
| WO | WO 2005/115990 A1 | 12/2005 |
| WO | WO 2006/135667 A1 | 12/2006 |
| WO | WO 2007/044895 A2 | 4/2007 |
| WO | WO 2007/105053 A2 | 9/2007 |
| WO | WO 2007/113276 A1 | 10/2007 |
| WO | WO 2007/131991 A1 | 11/2007 |
| WO | WO 2008/065199 A1 | 6/2008 |
| WO | WO 2008/097538 A1 | 8/2008 |
| WO | WO 2008/137139 A1 | 11/2008 |
| WO | WO 2008/156580 A1 | 12/2008 |
| WO | WO 2009/005729 A1 | 3/2009 |
| WO | WO 2009/032277 A1 | 3/2009 |
| WO | WO 2009/050277 A1 | 4/2009 |
| WO | WO 2009/073777 A1 | 6/2009 |

(Continued)

OTHER PUBLICATIONS

West, Anthony R., Solid State Chemistry and its Applications, Wiley, New York, 1988, pp. 358 & 365.*
Criton, M., et al. "Mutant Presenilins of Alzheimer's Disease Increase Production of 42-Residue Amyloid β-Protein in Both Transfected Cells and Transgenic Mice", Nature Medicine, vol. 3, No. 1, , pp. 67-72 (1997).
Eriksen, J., et al., NSAIDs and Enantiomers of Flurbiprofen Target γ-secretase and Lower Aγ42 In Vivo, Journal of Clinical Investigation, vol. 112, No. 3, (2003) pp. 440-449.
Greene, T., et al, "Protective Groups in Organic Synthesis", Third Edition, John Wiley & Sons, Inc.,(1999).
Larner, A. "Secretases as Therapeutic Targets in Alzheimer's Disease: Patents 200-2004", Expert Opinion ther. Patents (2004), 14(10), pp. 1403-1420.
Marjaux, E., et al. "γ-Secretase Inhibitors: Still in the Running as Alzheimer's Therapeutics", Drug Discovery Today: Therapeutic Strategies, vol. 1, No. 1, (2004).

(Continued)

*Primary Examiner* — Joseph Kosack
*Assistant Examiner* — Matthew Coughlin
(74) *Attorney, Agent, or Firm* — Peter Herridge

(57) ABSTRACT

The present invention is concerned with novel substituted bicyclic imidazole derivatives of Formula (I)

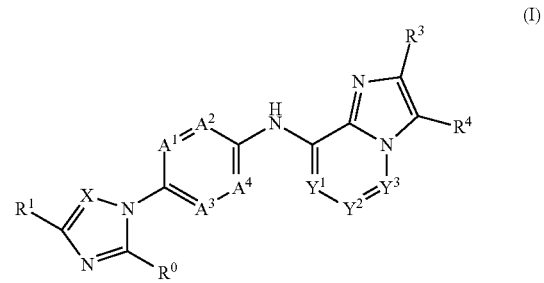

(I)

wherein $R^0$, $R^1$, $R^3$, $R^4$, X, $A^1$, $A^2$, $A^3$, $A^4$, $Y^1$, $Y^2$ and $Y^3$ have the meaning defined in the claims. The compounds according to the present invention are useful as gamma secretase modulators. The invention further relates to processes for preparing such novel compounds, pharmaceutical compositions comprising said novel compound as an active ingredient as well as the use of said compounds as a medicament.

13 Claims, No Drawings

(56) References Cited

FOREIGN PATENT DOCUMENTS

| WO | WO 2009/076352 A1 | 6/2009 |
|---|---|---|
| WO | WO 2009/103652 A1 | 8/2009 |
| WO | WO 2010/010188 A1 | 1/2010 |
| WO | WO 2010/137320 A1 | 2/2010 |
| WO | WO 2010/065310 A1 | 6/2010 |
| WO | WO 2010/070008 A1 | 6/2010 |
| WO | WO 2010/083141 A1 | 7/2010 |
| WO | WO 2010/089292 A1 | 8/2010 |
| WO | WO 2010/094647 A1 | 8/2010 |
| WO | WO 2010/098495 A1 | 9/2010 |
| WO | WO 2010/126745 A1 | 11/2010 |
| WO | WO 2010/145883 A1 | 12/2010 |
| WO | WO 2011/006903 A1 | 1/2011 |

OTHER PUBLICATIONS

Moechars, D., et al., Early Phenotypic Changes in Transgenic Mice That Overexpress Different Mutants of Amyloid Precursor Protein in Brain, Journal of Biological Chemistry, vol. 274, No. 10, pp. 6483-6492 (1999).

Morihara, T., et al. "Selective Inhibition of Aβ42 Production by NSAID R-Enantiomers", Journal of Neurochemistry, 83, pp. 1009-1012 (2002).

Peretto, I., et al. "Synthesis and Biological Activity of Flurbiprofen Analogues as Selective Inhibitors of β-Amyloid$_{1-42}$ Secretion", J. Med. Chem. 48, pp. 5705-5720 (2005).

Schweisguth, F., et al. Regulation of Notch Signaling Activity, Current Biology, vol. 14, pp. R129-R138 (2004).

Steiner, H., et al. "Uncovering γ-Secretase", Current Alzheimer Research, 175-181 (2004).

Tanzi, R., et al., "Twenty Years of the Alzheimer's Disease Amyloid Hypothesis: A Genetic Perspective", Cell, vol. 120, pp. 545-555 (2005).

Weggen, S., et al. "A subset of NSAIDs Lower Amyloidegenic Aβ42 Independently of Cyclooxygenase Activity", Letters to Nature, vol. 414, * Nov. 2001 pp. 212-216.

Jadhav, G., et al. "Amonium Metavanadate: A Novel Catalyst for Synthesis of 2-Substituted Benzimidazole Derivatives", Chinese Chemical Letters, vol. 20 (2009) pp. 292-295.

Matthews, D., et al. A Convenient Procedure for the Preparation of 4(5)-Cyanoimidazoles, Journal of Organic Chemistry, vol. 51 (1986), pp. 3228-3231.

Oumata, N., et al. "Roscovitine-Derived, Dual-Specificity Inhibitors of Cyclin-Dependent Kinases and Casein Kinases 1", Journal of Medicinal Chemistry, vol. 51, pp. 5229-5242 (2008).

Dyatkin, A., et al., "Determination of the Absolute Configuration of a Key Tricyclic Component of a Novel Vasopressin Receptor Antagonist by Use of Vibrational Circular Dichroism", Chirality, vol. 14, No. 215, pp. 215-219 (2002).

Search Report dated Jul. 20, 2012 for corresponding Application No. EP12168186.

Search Report dated Jul. 8, 2012 for corresponding Application No. PCT/EP2012/063667.

Zettle, H., "Exploring the Chemical Space of γ-Secretase Modulators", Trends in Pharmaceutical Sciences, vol. 31, No. 9, pp. 402-210 (EX027272529), 2010.

* cited by examiner

SUBSTITUTED BICYCLIC IMIDAZOLE DERIVATIVES AS GAMMA SECRETASE MODULATORS

CROSS REFERENCE TO RELATED APPLICATIONS

The instant application is a national stage application of Patent Application No. PCT/EP2009/067321, filed Dec. 16, 2009, which in turn claims the benefit of EPO Patent Application No. 08172202.7 filed Dec. 18, 2008. The complete disclosures of the aforementioned related patent applications are hereby incorporated herein by reference for all purposes.

FIELD OF THE INVENTION

The present invention is concerned with novel substituted bicyclic imidazole derivatives useful as Gamma Secretase Modulators (GSM). The invention further relates to processes for preparing such novel compounds, pharmaceutical compositions comprising said novel compound as an active ingredient as well as the use of said compounds as a medicament.

BACKGROUND OF THE INVENTION

Alzheimer's Disease (AD) is a progressive neurodegenerative disorder marked by loss of memory, cognition, and behavioral stability. AD afflicts 6-10% of the population over age 65 and up to 50% over age 85. It is the leading cause of dementia and the third leading cause of death after cardiovascular disease and cancer. There is currently no effective treatment for AD. The total net cost related to AD in the U.S. exceeds $100 billion annually.

AD does not have a simple etiology, however, it has been associated with certain risk factors including (1) age, (2) family history and (3) head trauma; other factors include environmental toxins and low levels of education. Specific neuropathological lesions in the limbic and cerebral cortices include intracellular neurofibrillary tangles consisting of hyperphosphorylated tau protein and the extracellular deposition of fibrillar aggregates of amyloid beta peptides (amyloid plaques). The major component of amyloid plaques are the amyloid beta (A-beta, Abeta or Aβ) peptides of various lengths. A variant thereof, which is the Aβ1-42-peptide (Abeta-42), is believed to be the major causative agent for amyloid formation. Another variant is the Aβ1-40-peptide (Abeta-40). Amyloid beta is the proteolytic product of a precursor protein, beta amyloid precursor protein (beta-APP or APP).

Familial, early onset autosomal dominant forms of AD have been linked to missense mutations in the β-amyloid precursor protein (β-APP or APP) and in the presenilin proteins 1 and 2. In some patients, late onset forms of AD have been correlated with a specific allele of the apolipoprotein E (ApoE) gene, and, more recently, the finding of a mutation in alpha2-macroglobulin, which may be linked to at least 30% of the AD population. Despite this heterogeneity, all forms of AD exhibit similar pathological findings. Genetic analysis has provided the best clues for a logical therapeutic approach to AD. All mutations, found to date, affect the quantitative or qualitative production of the amyloidogenic peptides known as Abeta-peptides (Aβ), specifically Aβ42, and have given strong support to the "amyloid cascade hypothesis" of AD (Tanzi and Bertram, 2005, Cell 120, 545). The likely link between Aβ peptide generation and AD pathology emphasizes the need for a better understanding of the mechanisms of Aβ production and strongly warrants a therapeutic approach at modulating Aβ levels.

The release of Aβ peptides is modulated by at least two proteolytic activities referred to as β- and γ-secretase cleaving at the N-terminus (Met-Asp bond) and the C-terminus (residues 37-42) of the Aβ peptide, respectively. In the secretory pathway, there is evidence that β-secretase cleaves first, leading to the secretion of s-APPβ (sβ) and the retention of a 11 kDa membrane-bound carboxy terminal fragment (CTF). The latter is believed to give rise to Aβ peptides following cleavage by γ-secretase. The amount of the longer isoform, Aβ42, is selectively increased in patients carrying certain mutations in a particular protein (presenilin), and these mutations have been correlated with early-onset familial Alzheimer's disease. Therefore, Aβ42 is believed by many researchers to be the main culprit of the pathogenesis of Alzheimer's disease.

It has now become clear that the γ-secretase activity cannot be ascribed to a single particular protein, but is in fact associated with an assembly of different proteins.

The gamma (γ)-secretase activity resides within a multiprotein complex containing at least four components: the presenilin (PS) heterodimer, nicastrin, aph-1 and pen-2. The PS heterodimer consists of the amino- and carboxyterminal PS fragments generated by endoproteolysis of the precursor protein. The two aspartates of the catalytic site are at the interface of this heterodimer. It has recently been suggested that nicastrin serves as a gamma-secretase-substrate receptor. The functions of the other members of gamma-secretase are unknown, but they are all required for activity (Steiner, 2004. Curr. Alzheimer Research 1(3): 175-181).

Thus, although the molecular mechanism of the second cleavage-step has remained elusive until now, the γ-secretase-complex has become one of the prime targets in the search for compounds for the treatment of Alzheimer's disease.

Various strategies have been proposed for targeting gamma-secretase in Alzheimer's disease, ranging from targeting the catalytic site directly, developing substrate-specific inhibitors and modulators of gamma-secretase activity (Marjaux et al., 2004. Drug Discovery Today: Therapeutic Strategies, Volume 1, 1-6). Accordingly, a variety of compounds were described that have secretases as targets (Larner, 2004. Secretases as therapeutics targets in Alzheimer's disease: patents 2000-2004. Expert Opin. Ther. Patents 14, 1403-1420).

Indeed, this finding was recently supported by biochemical studies in which an effect of certain NSAIDs on γ-secretase was shown (Weggen et al (2001) Nature 414, 6860, 212 and WO 01/78721 and US 2002/0128319; Morihara et al (2002) J. Neurochem. 83, 1009; Eriksen (2003) J. Clin. Invest. 112, 440). Potential limitations for the use of NSAIDs to prevent or treat AD are their inhibition activity of COX enzymes, which can lead to unwanted side effects, and their low CNS penetration (Peretto et al., 2005, J. Med. Chem. 48, 5705-5720).

WO-2006/135667 relates amongst others to imidazopyridine compounds which inhibit the activity of the enzyme 11-beta-hydroxysteroid dehydrogenase type I.

US 2008/0280948 A1 relates to aminophenyl derivatives which are modulators for amyloid beta.

WO-2008/137139 relates to heterocyclic derivatives and their use as gamma secretase modulators.

WO-2004/110350 relates to aryl compounds and their use in modulating Aβ.

There is a strong need for novel compounds which modulate γ-secretase activity thereby opening new avenues for the treatment of Alzheimer's disease. It is an object of the present invention to overcome or ameliorate at least one of the disadvantages of the prior art, or to provide a useful alternative. It is accordingly an object of the present invention to provide such novel compounds.

SUMMARY OF THE INVENTION

It has been found that the compounds of the present invention are useful as gamma secretase modulators. The compounds according to the invention and the pharmaceutically acceptable compositions thereof, may be useful in the treatment or prevention of Alzheimer's disease.

The present invention concerns novel compounds of Formula (I):

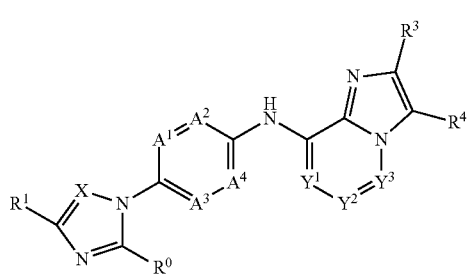

and stereoisomeric forms thereof, wherein
$R^0$ is hydrogen, halo or $C_{1-4}$alkyl;
$R^1$ is hydrogen, $C_{1-4}$alkyl or halo;
X is $CR^7$ or N; wherein $R^7$ is hydrogen or halo;
$A^1$ is $CR^2$ or N;
$A^2$ is $CR^8$ or N;
$A^3$ and $A^4$ each independently are CH or N;
provided that no more than two of $A^1$, $A^2$, $A^3$ and $A^4$ are N;
$R^2$ is hydrogen, halo or $C_{1-4}$alkyloxy;
$R^8$ is hydrogen or halo;
$R^3$ is hydrogen; $C_{1-6}$alkyl optionally substituted with one or more substituents each independently selected from the group consisting of hydroxyl, halo, morpholinyl, piperidinyl, pyrrolidinyl, tetrahydropyranyl, Ar, $C_{1-6}$alkyloxy, cyclo$C_{3-7}$alkyloxy, and cyclo$C_{3-7}$alkyl; carboxyl; $C_{2-4}$alkenyl; $NR^5R^6$-carbonyl; cyclo$C_{3-7}$alkyl; Ar; tetrahydropyranyl; $C_{1-6}$alkylcarbonyl; $C_{1-6}$alkyloxycarbonyl; or Ar—O—$CH_2$—;
  wherein each Ar independently is phenyl optionally substituted with one or more substituents each independently selected from the group consisting of halo, $C_{1-4}$alkyloxy, cyano, $NR^5R^6$, morpholinyl, $C_{1-4}$alkyl, and $C_{1-4}$alkyl substituted with one or more substituents each independently selected from the group consisting of halo, $C_{1-4}$alkyloxy, and $NR^5R^6$; benzimidazolyl optionally substituted with one or more substituents each independently selected from $C_{1-4}$alkyl; or pyridinyl optionally substituted with one or more substituents each independently selected from the group consisting of halo, $C_{1-4}$alkyloxy, cyano, $C_{1-4}$alkyl, and $C_{1-4}$alkyl substituted with one or more substituents each independently selected from halo;
each $R^5$ independently is hydrogen, $C_{1-4}$alkyl, $C_{1-6}$alkylcarbonyl, or $C_{1-4}$alkyloxy$(CH_2CH_2O)_n$—$CH_2$-carbonyl;
n is an integer selected from 1, 2, 3, 4, 5 or 6.
each $R^6$ independently is hydrogen or $C_{1-4}$alkyl;
$R^4$ is hydrogen; cyano; halo; phenyl optionally substituted with one or more substituents each independently selected from the group consisting of halo and phenyl; phenylcarbonyl optionally substituted with one or more substituents each independently selected from halo; $C_{1-4}$alkyloxy; $C_{1-6}$alkyl optionally substituted with one or more substituents each independently selected from the group consisting of halo, $NR^5R^6$, $C_{1-4}$alkyloxy, hydroxyl, and formylamino;
$Y^1$ is CH or N;
$Y^2$ is $CR^9$ or N;
$Y^3$ is CH or N;
provided that only one of $Y^1$, $Y^2$ and $Y^3$ may represent N;
$R^9$ is hydrogen; halo; $C_{1-4}$alkyloxy; cyano; cyclo$C_{3-7}$alkyl; tetrahydropyranyl; $C_{2-4}$alkenyl; phenyl optionally substituted with one or more substituents each independently selected from $C_{1-4}$alkyloxy; or $C_{1-4}$alkyl optionally substituted with one or more substituents each independently selected from the group consisting of halo and $C_{1-4}$alkyloxy;
and the pharmaceutically acceptable addition salts, and the solvates thereof.

The present invention also concerns methods for the preparation of compounds of Formula (I) and pharmaceutical compositions comprising them.

The present compounds surprisingly were found to modulate the γ-secretase activity in vitro and in vivo, and are therefore useful in the treatment or prevention of Alzheimer's disease (AD), traumatic brain injury, mild cognitive impairment (MCI), senility, dementia, dementia with Lewy bodies, cerebral amyloid angiopathy, multi-infarct dementia, Down's syndrome, dementia associated with Parkinson's disease and dementia associated with beta-amyloid, preferably Alzheimer's disease and other disorders with Beta-amyloid pathology (eg glaucoma).

In view of the aforementioned pharmacology of the compounds of Formula (I), it follows that they are suitable for use as a medicament.

More especially the compounds are suitable in the treatment or prevention of Alzheimer's disease, cerebral amyloid angiopathy, multi-infarct dementia, dementia pugilistica or Down syndrome.

The present invention also concerns to the use of a compound according to the general Formula (I), the stereoisomeric forms thereof and the pharmaceutically acceptable acid or base addition salts and the solvates thereof, for the manufacture of a medicament for the modulation of γ-secretase activity.

Use of a compound of Formula (I) for the modulation of γ-secretase activity resulting in a decrease in the relative amount of Aβ42-peptides produced are preferred.

One advantage of the compounds or a part of the compounds of the present invention may lie in their enhanced CNS-penetration.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

When indicating the number of substituents, the term "one or more" means from one substituent to the highest possible number of substitution, i.e. replacement of one hydrogen up to replacement of all hydrogens by substituents each individually selected from the indicated groups, provided that the normal valency is not exceeded, and that the substitution results in a chemically stable compound, i.e. a compound that is sufficiently robust to survive isolation to a useful degree of purity from a reaction mixture, and formulation into a therapeutic agent. Thereby, one, two, three or four substituents are preferred. In particular one, two or three substitutents are preferred. More in particular one substituent is preferred.

The term "halo" or "halogen" as a group or part of a group is generic for fluoro, chloro, bromo, iodo unless otherwise is indicated.

The term "$C_{1-6}$alkyl" as a group or part of a group refers to a hydrocarbyl radical of Formula $C_nH_{2n+1}$ wherein n is a number ranging from 1 to 6. $C_{1-6}$alkyl groups comprise from 1 to 6 carbon atoms, preferably from 1 to 4 carbon atoms, more preferably from 1 to 3 carbon atoms, still more preferably 1 to 2 carbon atoms. Alkyl groups may be linear or branched and may be substituted as indicated herein. When a subscript is used herein following a carbon atom, the subscript refers to the number of carbon atoms that the named group may contain. Thus, for example, $C_{1-6}$alkyl includes all linear, or branched alkyl groups with between 1 and 6 carbon atoms, and thus includes such as for example methyl, ethyl, n-propyl, i-propyl, 2-methyl-ethyl, butyl and its isomers (e.g. n-butyl, isobutyl and tert-butyl); pentyl and its isomers, hexyl and its isomers, and the like.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, more preferably 1 to 2 carbon atoms. Alkyl groups may be linear or branched and may be substituted as indicated herein. When a subscript is used herein following a carbon atom, the subscript refers to the number of carbon atoms that the named group may contain. Thus, for example, $C_{1-4}$alkyl includes all linear, or branched alkyl groups with between 1 and 4 carbon atoms, and thus includes such as for example methyl, ethyl, n-propyl, i-propyl, 2-methyl-ethyl, butyl and its isomers (e.g. n-butyl, isobutyl and tert-butyl); and the like.

In the framework of this application, $C_{2-4}$alkenyl is a straight or branched hydrocarbon radical having from 2 to 4 carbon atoms containing a double bond such as ethenyl, propenyl, butenyl, 1-propen-2-yl and the like.

The term "$C_{1-6}$alkyloxy" as a group or part of a group refers to a radical having the Formula $R^b$—O— wherein $R^b$ is $C_{1-6}$alkyl. Non-limiting examples of suitable alkyloxy include methyloxy, ethyloxy, propyloxy, isopropyloxy, butyloxy, isobutyloxy, sec-butyloxy, tert-butyloxy, pentyloxy, and hexyloxy.

The term "$C_{1-4}$alkyloxy" as a group or part of a group refers to a radical having the Formula $R^c$—O— wherein $R^c$ is $C_{1-4}$alkyl. Non-limiting examples of suitable alkyloxy include methyloxy, ethyloxy, propyloxy, isopropyloxy, butyloxy, isobutyloxy, sec-butyloxy and tert-butyloxy.

The term "cyclo$C_{3-7}$alkyl" alone or in combination, refers to a cyclic saturated hydrocarbon radical having from 3 to 7 carbon atoms. Non-limiting examples of suitable cyclo$C_{3-7}$alkyl include cyclopropyl, cyclobutyl, cyclopentyl, cyclohexyl and cycloheptyl.

The term "cyclo$C_{3-7}$alkyloxy" alone or in combination, refers to a saturated cyclo$C_{3-7}$alkyl-O—, wherein cyclo$C_{3-7}$alkyl is as defined above. Non-limiting examples of suitable cyclo$C_{3-7}$alkyl include cyclopropyloxy, cyclobutyloxy, cyclopentyloxy, cyclohexyloxy and cycloheptyloxy.

The chemical names of the compounds of the present invention were generated according to the nomenclature rules agreed upon by the Chemical Abstracts Service (CAS). In case of tautomeric forms, the name of the depicted tautomeric form of the structure was generated. However it should be clear that the other non-depicted tautomeric form is also included within the scope of the present invention.

When any variable occurs more than one time in any constituent, each definition is independent.

It will be appreciated that some of the compounds of Formula (I) and their pharmaceutically acceptable addition salts and stereoisomeric forms may contain one or more centers of chirality and exist as stereoisomeric forms.

The term "stereoisomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereoisomeric forms of the compounds of Formula (I) are embraced within the scope of this invention.

When a specific stereoisomeric form is indicated, this means that said form is substantially free, i.e. associated with less than 50%, preferably less than 20%, more preferably less than 10%, even more preferably less than 5%, further preferably less than 2% and most preferably less than 1% of the other isomer(s).

When a specific regioisomeric form is indicated, this means that said form is substantially free, i.e. associated with less than 50%, preferably less than 20%, more preferably less than 10%, even more preferably less than 5%, further preferably less than 2% and most preferably less than 1% of the other isomer(s).

For therapeutic use, salts of the compounds of Formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds of Formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds of formula (I) are able to form, as well as the salts thereof. Examples of such forms are e.g. hydrates, alcoholates and the like.

The compounds of Formula (I) as prepared in the processes described below may be synthesized in the form of racemic mixtures of enantiomers that can be separated from one another following art-known resolution procedures. An manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the framework of this application, a compound according to the invention is inherently intended to comprise all isotopic combinations of its chemical elements. In the framework of this application, a chemical element, in particular when mentioned in relation to a compound according to formula (I), comprises all isotopes and isotopic mixtures of this element. For example, when hydrogen is mentioned, it is understood to refer to $^{1}H$, $^{2}H$, $^{3}H$ and mixtures thereof.

A compound according to the invention therefore inherently comprises a compound with one or more isotopes of one or more element, and mixtures thereof, including a radioactive compound, also called radiolabelled compound, wherein one or more non-radioactive atoms has been replaced by one of its radioactive isotopes. By the term "radiolabelled compound" is meant any compound according to formula (I), or a pharmaceutically acceptable salt thereof, which contains at least one radioactive atom. For example, a compound can be labelled with positron or with gamma emitting radioactive isotopes. For radioligand-binding techniques, the $^{3}H$-atom or the $^{125}I$-atom is the atom of choice to be replaced. For imaging, the most commonly used positron emitting (PET) radioactive isotopes are $^{11}C$, $^{18}F$, $^{15}O$ and $^{13}N$, all of which are accelerator produced and have half-lives of 20, 100, 2 and 10 minutes respectively. Since the half-lives of these radioactive isotopes are so short, it is only feasible to use them at institutions which have an accelerator on site for their production, thus limiting their use. The most widely used of these are $^{18}F$, $^{99m}Tc$, $^{201}Tl$ and $^{123}I$. The handling of these radioactive isotopes, their production, isolation and incorporation in a molecule are known to the skilled person.

In particular, the radioactive atom is selected from the group of hydrogen, carbon, nitrogen, sulfur, oxygen and halogen. In particular, the radioactive isotope is selected from the group of $^{3}H$, $^{11}C$, $^{18}F$, $^{122}I$, $^{123}I$, $^{125}I$, $^{131}I$, $^{75}Br$, $^{76}Br$, $^{77}Br$ and $^{82}Br$.

As used in the specification and the appended claims, the singular forms "a", "an," and "the" also include plural references unless the context clearly dictates otherwise. By way of example, "a compound" means one compound or more than one compound.

The terms described above and others used in the specification are well understood to those in the art.

Preferred features of the compounds of this invention are now set forth.

In an embodiment, the present invention concerns novel compounds of Formula (I):

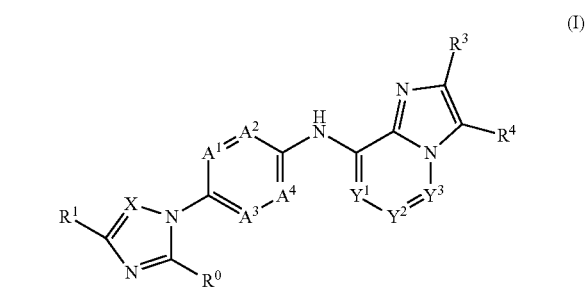

and stereoisomeric forms thereof, wherein
$R^{0}$ is hydrogen, halo or $C_{1-4}$alkyl;
$R^{1}$ is hydrogen, $C_{1-4}$alkyl or halo;
X is $CR^{7}$ or N; wherein $R^{7}$ is hydrogen or halo;
$A^{1}$ is $CR^{2}$ or N;
$A^{2}$ is $CR^{8}$ or N;
$A^{3}$ and $A^{4}$ each independently are CH or N;
provided that no more than two of $A^{1}$, $A^{2}$, $A^{3}$ and $A^{4}$ are N;
$R^{2}$ is hydrogen, halo or $C_{1-4}$alkyloxy;
$R^{8}$ is hydrogen or halo;
$R^{3}$ is hydrogen; $C_{1-6}$alkyl optionally substituted with one or more substituents each independently selected from the group consisting of hydroxyl, halo, morpholinyl, piperidinyl, pyrrolidinyl, tetrahydropyranyl, Ar, $C_{1-6}$alkyloxy, cycloC$_{3-7}$alkyloxy, and cycloC$_{3-7}$alkyl; carboxyl; $C_{2-4}$alkenyl; $NR^{5}R^{6}$-carbonyl; cycloC$_{3-7}$alkyl; Ar; tetrahydropyranyl; $C_{1-6}$alkylcarbonyl; $C_{1-6}$alkyloxycarbonyl; or Ar—O—CH$_{2}$—;
wherein each Ar independently is phenyl optionally substituted with one or more substituents each independently selected from the group consisting of halo, $C_{1-4}$alkyloxy, cyano, $NR^{5}R^{6}$, morpholinyl, $C_{1-4}$alkyl, and $C_{1-4}$alkyl substituted with one or more substituents each independently selected from the group consisting of halo, $C_{1-4}$alkyloxy, and $NR^{5}R^{6}$; benzimidazolyl optionally substituted with one or more substituents each independently selected from $C_{1-4}$alkyl; or pyridinyl optionally substituted with one or more substituents each independently selected from the group consisting of halo, $C_{1-4}$alkyloxy, cyano, $C_{1-4}$alkyl, and $C_{1-4}$alkyl substituted with one or more substituents each independently selected from halo;
each $R^{5}$ independently is hydrogen, $C_{1-4}$alkyl, $C_{1-6}$alkylcarbonyl, or $C_{1-4}$alkyloxy(CH$_{2}$CH$_{2}$O)$_{n}$—CH$_{2}$-carbonyl;
n is an integer selected from 1, 2, 3, 4, 5 or 6.
each $R^{6}$ independently is hydrogen or $C_{1-4}$alkyl;
$R^{4}$ is hydrogen; cyano; halo; phenyl optionally substituted with one or more substituents each independently selected from the group consisting of halo and phenyl; phenylcarbonyl optionally substituted with one or more substituents each independently selected from halo; $C_{1-4}$alkyloxy; $C_{1-6}$alkyl optionally substituted with one or more substituents each independently selected from the group consisting of halo, $NR^5R^6$, $C_{1-4}$alkyloxy, hydroxyl, and formylamino;
$Y^1$ is CH or N;
$Y^2$ is $CR^9$ or N;
$Y^3$ is CH or N;
provided that only one of $Y^1$, $Y^2$ and $Y^3$ may represent N;
$R^9$ is hydrogen; halo; $C_{1-4}$alkyloxy; cyano; cyclo$C_{3-7}$alkyl; tetrahydropyranyl; $C_{2-4}$alkenyl; phenyl optionally substituted with one or more substituents each independently selected from $C_{1-4}$alkyloxy; or $C_{1-4}$alkyl optionally substituted with one or more substituents each independently selected from the group consisting of halo and $C_{1-4}$alkyloxy;
and the pharmaceutically acceptable addition salts, and the solvates thereof.

In an embodiment, the invention relates to compounds of Formula (I) and stereoisomeric forms thereof, wherein one or more, preferably all, of the following restrictions apply:
(a) $R^0$ is hydrogen or $C_{1-4}$alkyl;
(b) $R^1$ is hydrogen or $C_{1-4}$alkyl;
(c) X is CH or N;
(d) $R^3$ is hydrogen; $C_{1-6}$alkyl optionally substituted with one or more substituents each independently selected from the group consisting of hydroxyl, halo, morpholinyl, piperidinyl, tetrahydropyranyl, Ar, $C_{1-6}$alkyloxy, and cyclo$C_{3-7}$alkyl; carboxyl; $C_{2-4}$alkenyl; $NR^5R^6$-carbonyl; cyclo$C_{3-7}$alkyl; Ar; tetrahydropyranyl; $C_{1-6}$alkylcarbonyl; $C_{1-6}$alkyloxycarbonyl; or Ar—O—CH$_2$—;
wherein each Ar independently is phenyl optionally substituted with one or more substituents each independently selected from the group consisting of halo, $C_{1-4}$alkyloxy, cyano, $NR^5R^6$, morpholinyl, $C_{1-4}$alkyl, and $C_{1-4}$alkyl substituted with one or more substituents each independently selected from the group consisting of halo and $NR^5R^6$; benzimidazolyl optionally substituted with one or more substituents each independently selected from $C_{1-4}$alkyl; or pyridinyl;
(e) n is 2;
(f) $R^4$ is hydrogen; cyano; halo; phenyl optionally substituted with one or more substituents each independently selected from the group consisting of halo and phenyl; phenylcarbonyl optionally substituted with one or more substituents each independently selected from halo; $C_{1-4}$alkyloxy; $C_{1-6}$alkyl optionally substituted with one or more substituents each independently selected from the group consisting of $NR^5R^6$, $C_{1-4}$alkyloxy, hydroxyl, and formylamino;
(g) $Y^1$ is CH or N;
$Y^2$ is $CR^9$;
$Y^3$ is CH or N;
provided that only one of $Y^1$ and $Y^3$ may represent N;
(h) $R^9$ is hydrogen; halo; tetrahydropyranyl; $C_{2-4}$alkenyl; phenyl optionally substituted with one or more substituents each independently selected from $C_{1-4}$alkyloxy; or $C_{1-4}$alkyl optionally substituted with one or more substituents each independently selected from halo;
and the pharmaceutically acceptable addition salts, and the solvates thereof.

In an embodiment, the invention relates to compounds of Formula (I) and stereoisomeric forms thereof, wherein one or more, preferably all, of the following restrictions apply:
(a) $R^0$ is hydrogen or methyl;
(b) $R^1$ is hydrogen, methyl or ethyl;
(c) X is CH or N;
(d) $A^1$ is $CR^2$ or N;
(e) $A^2$ is $CR^8$ or N;
(f) $A^3$ and $A^4$ each independently are CH or N;
provided that no more than two of $A^1$, $A^2$, $A^3$ and $A^4$ are N;
(g) $R^2$ is hydrogen, fluoro or methoxy;
(h) $R^8$ is hydrogen or fluoro;
(i) $R^3$ is hydrogen; $C_{1-6}$alkyl optionally substituted with one or more substituents each independently selected from the group consisting of hydroxyl, fluoro, morpholinyl, piperidinyl, tetrahydropyranyl, Ar, isopropyloxy, and cyclohexyl; carboxyl; ethenyl; $NR^5R^6$-carbonyl; cyclopropyl; Ar; tetrahydropyranyl; ethylcarbonyl; $C_{1-6}$alkyloxycarbonyl; or Ar—O—CH$_2$—;
wherein each Ar independently is phenyl optionally substituted with one or more substituents each independently selected from the group consisting of chloro, fluoro, methoxy, cyano, $NR^5R^6$, morpholinyl, isobutyl, methyl, and methyl substituted with one or more substituents each independently selected from the group consisting of fluoro and $NR^5R^6$; benzimidazolyl optionally substituted with one or more methyl groups; or pyridinyl;
(j) each $R^5$ independently is hydrogen, methyl, ethyl, methylcarbonyl, ethylcarbonyl, or methoxy(CH$_2$CH$_2$O)$_n$—CH$_2$-carbonyl;
(k) n is 2;
(l) each $R^6$ independently is hydrogen, methyl, or ethyl;
(m) $R^4$ is hydrogen; cyano; bromo; chloro; phenyl optionally substituted with one or more substituents each independently selected from the group consisting of fluoro and phenyl; phenylcarbonyl optionally substituted with one or more fluoro atoms; methoxy; $C_{1-6}$alkyl optionally substituted with one or more substituents each independently selected from the group consisting of $NR^5R^6$, methoxy, hydroxyl, and formylamino;
(n) $Y^1$ is CH or N;
$Y^2$ is $CR^9$;
$Y^3$ is CH or N;
provided that only one of $Y^1$ and $Y^3$ may represent N;
(o) $R^9$ is hydrogen; fluoro; chloro; bromo; tetrahydropyranyl; 2-methyl-1-propen-3-yl;
phenyl optionally substituted with one or more methoxy groups; or $C_{1-4}$alkyl optionally substituted with one or more fluoro atoms;
and the pharmaceutically acceptable addition salts, and the solvates thereof.

In an embodiment, the present invention relates to compounds according to any of the other embodiments or any combination of the other embodiments wherein the compounds of Formula (I) are restricted to the compounds of Formula (I-a)

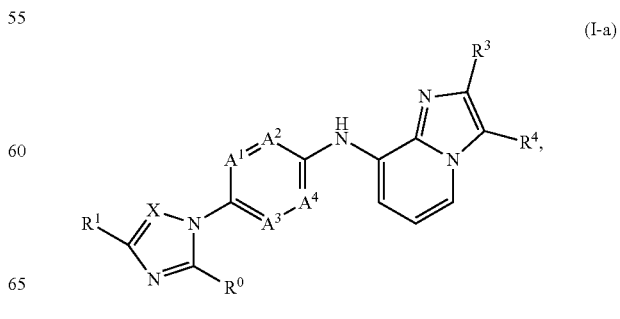

including any stereochemically isomeric form thereof,
and the pharmaceutically acceptable addition salts, and the solvates thereof.

In an embodiment, the present invention relates to novel compounds wherein Formula (I) is restricted to Formula (I-a):

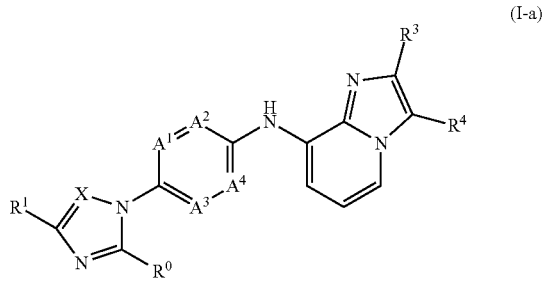

(I-a)

and stereoisomeric forms thereof, wherein
$R^0$ is hydrogen or $C_{1-4}$alkyl; preferably hydrogen, methyl or ethyl; more preferably hydrogen or methyl; even more preferably hydrogen;
$R^1$ is hydrogen, $C_{1-4}$alkyl or halo; preferably hydrogen or $C_{1-4}$alkyl; more preferably hydrogen or methyl; even more preferably methyl;
X is $CR^7$ or N; wherein $R^7$ is hydrogen or halo; preferably X is CH or N;
$A^1$ is $CR^2$ or N;
$A^2$, $A^3$ and $A^4$ each independently are CH or N; provided that no more than two of $A^1$, $A^2$, $A^3$ and $A^4$ are N;
$R^2$ is hydrogen, halo or $C_{1-4}$alkyloxy;
$R^3$ is hydrogen; $C_{1-6}$alkyl optionally substituted with one or more substituents each independently selected from the group consisting of halo, morpholinyl, piperidinyl, pyrrolidinyl, Ar, $C_{1-6}$alkyloxy, cyclo$C_{3-7}$alkyloxy, and cyclo$C_{3-7}$ alkyl; cyclo$C_{3-7}$alkyl; tetrahydropyranyl; Ar; or Ar—O—CH$_2$—;
preferably $R^3$ is hydrogen; $C_{1-6}$alkyl optionally substituted with one or more substituents each independently selected from the group consisting of morpholinyl, piperidinyl, Ar, $C_{1-6}$alkyloxy, and cyclo$C_{3-7}$alkyl; tetrahydropyranyl; Ar; or Ar—O—CH$_2$—; more preferably $R^3$ is $C_{1-6}$alkyl optionally substituted with one or more substituents each independently selected from Ar; tetrahydropyranyl; or Ar;
even more preferably $R^3$ is methyl substituted with one or more substituents each independently selected from Ar; or Ar;
each Ar independently is phenyl optionally substituted with one or more substituents each independently selected from the group consisting of halo, $C_{1-4}$alkyloxy, cyano, $NR^5R^6$, morpholinyl, $C_{1-4}$alkyl, and $C_{1-4}$alkyl substituted with one or more substituents each independently selected from halo; benzimidazolyl optionally substituted with one or more substituents each independently selected from $C_{1-4}$alkyl; or pyridinyl optionally substituted with one or more substituents each independently selected from the group consisting of halo, $C_{1-4}$alkyloxy, cyano, $C_{1-4}$alkyl, and $C_{1-4}$alkyl substituted with one or more substituents each independently selected from halo;
preferably each Ar independently is phenyl optionally substituted with one or more substituents each independently selected from the group consisting of halo, methoxy, cyano, $NR^5R^6$, $CF_3$, morpholinyl, and $C_{1-4}$alkyl; 1-methyl-benzimidazolyl; or pyridinyl;
wherein each $R^5$ independently is hydrogen or $C_{1-4}$alkyl; preferably $C_{1-4}$alkyl; more preferably ethyl;
wherein each $R^6$ independently is hydrogen or $C_{1-4}$alkyl; preferably $C_{1-4}$alkyl; more preferably ethyl;
$R^4$ is hydrogen; cyano; halo; phenyl optionally substituted with one or more substituents each independently selected from the group consisting of halo and phenyl; phenylcarbonyl optionally substituted with one or more substituents each independently selected from halo; $C_{1-6}$alkyl optionally substituted with one or more substituents each independently selected from $C_{1-4}$alkyloxy; or $C_{1-4}$alkyl substituted with one or more substituents each independently selected from halo;
preferably $R^4$ is hydrogen; halo; phenyl optionally substituted with one or more substituents each independently selected from the group consisting of halo and phenyl; phenylcarbonyl optionally substituted with one or more substituents each independently selected from halo; or $C_{1-6}$alkyl optionally substituted with one or more substituents each independently selected from $C_{1-4}$alkyloxy;
more preferably $R^4$ is hydrogen; or $C_{1-6}$alkyl;
and the pharmaceutically acceptable addition salts, and the solvates thereof.

In an embodiment, the invention relates to compounds of Formula (I) and stereoisomeric forms thereof, wherein
$R^0$ is hydrogen or $C_{1-4}$alkyl;
$R^1$ is hydrogen, $C_{1-4}$alkyl or halo;
X is $CR^7$ or N; wherein $R^7$ is hydrogen or halo;
$A^1$ is $CR^2$ or N;
$A^2$, $A^3$ and $A^4$ each independently are CH or N; provided that no more than two of $A^1$, $A^2$, $A^3$ and $A^4$ are N;
$R^2$ is hydrogen, halo or $C_{1-4}$alkyloxy;
$R^3$ is hydrogen; $C_{1-6}$alkyl optionally substituted with one substituent selected from the group consisting of morpholinyl, piperidinyl, Ar, $C_{1-6}$alkyloxy, and cyclo$C_{3-7}$alkyl; tetrahydropyranyl; Ar; or Ar—O—CH$_2$—;
wherein each Ar independently is phenyl optionally substituted with one or more substituents each independently selected from the group consisting of halo, $C_{1-4}$alkyloxy, cyano, $NR^5R^6$, morpholinyl, $C_{1-4}$alkyl, and $C_{1-4}$alkyl substituted with one or more substituents each independently selected from halo; benzimidazolyl optionally substituted with one or more substituents each independently selected from $C_{1-4}$alkyl; or pyridinyl;
wherein each $R^5$ independently is $C_{1-4}$alkyl;
wherein each $R^6$ independently is $C_{1-4}$alkyl;
$R^4$ is hydrogen; cyano; halo; phenyl optionally substituted with one or more substituents each independently selected from the group consisting of halo and phenyl; phenylcarbonyl optionally substituted with one or more substituents each independently selected from halo; $C_{1-6}$alkyl optionally substituted with one or more substituents each independently selected from $C_{1-4}$alkyloxy; or $C_{1-4}$alkyl substituted with one or more substituents each independently selected from halo;
and the pharmaceutically acceptable addition salts, and the solvates thereof.

In an embodiment, the invention relates to compounds of Formula (I) and stereoisomeric forms thereof, wherein
$R^0$ is hydrogen or $C_{1-4}$alkyl;
$R^1$ is hydrogen or $C_{1-4}$alkyl;
X is CH or N;
$A^1$ is $CR^2$ or N;

$A^2$, $A^3$ and $A^4$ each independently are CH or N; provided that no more than two of $A^1$, $A^2$, $A^3$ and $A^4$ are N;

$R^2$ is hydrogen, halo or $C_{1-4}$alkyloxy;

$R^3$ is hydrogen; $C_{1-6}$alkyl optionally substituted with one substituent selected from the group consisting of morpholinyl, piperidinyl, Ar, $C_{1-6}$alkyloxy, and cyclo$C_{3-7}$alkyl; tetrahydropyranyl; Ar; or Ar—O—CH$_2$—;

wherein each Ar independently is phenyl optionally substituted with one or more substituents each independently selected from the group consisting of halo, $C_{1-4}$alkyloxy, cyano, NR$^5$R$^6$, morpholinyl, $C_{1-4}$alkyl, and $C_{1-4}$alkyl substituted with one or more substituents each independently selected from halo; benzimidazolyl optionally substituted with one or more substituents each independently selected from $C_{1-4}$alkyl; or pyridinyl;

wherein each $R^5$ independently is $C_{1-4}$alkyl;

wherein each $R^6$ independently is $C_{1-4}$alkyl;

$R^4$ is hydrogen; cyano; halo; phenyl optionally substituted with one or more substituents each independently selected from the group consisting of halo and phenyl; phenylcarbonyl optionally substituted with one or more substituents each independently selected from halo; or $C_{1-6}$alkyl;

and the pharmaceutically acceptable addition salts, and the solvates thereof.

In another embodiment, the invention relates to compounds of Formula (I) and stereoisomeric forms thereof, wherein $R^0$ is hydrogen or methyl;

$R^1$ is hydrogen, methyl, ethyl or bromo;

X is CR$^7$ or N; wherein R$^7$ is hydrogen or chloro;

$A^1$ is CR$^2$ or N;

$A^2$, $A^3$ and $A^4$ each independently are CH or N; provided that no more than two of $A^1$, $A^2$, $A^3$ and $A^4$ are N;

$R^2$ is hydrogen, fluoro, or methoxy;

$R^3$ is hydrogen; $C_{1-6}$alkyl optionally substituted with one substituent selected from the group consisting of morpholinyl, piperidinyl, Ar, isopropyloxy, cyclopentyl, and cyclohexyl; tetrahydropyranyl; Ar; or Ar—O—CH$_2$—;

wherein each Ar independently is phenyl optionally substituted with one or more substituents each independently selected from the group consisting of fluoro, chloro, methoxy, cyano, NR$^5$R$^6$, morpholinyl, methyl, isobutyl, and trifluoromethyl; benzimidazolyl optionally substituted with one methyl; or pyridinyl;

wherein $R^5$ is ethyl;

wherein $R^6$ is ethyl;

$R^4$ is hydrogen; cyano; chloro; iodo; bromo; phenyl optionally substituted with one or more substituents each independently selected from the group consisting of fluoro and phenyl; phenylcarbonyl optionally substituted with one or more fluoro atoms; $C_{1-6}$alkyl optionally substituted with one or more methoxy groups; or trifluoromethyl;

and the pharmaceutically acceptable addition salts, and the solvates thereof.

In another embodiment, the invention relates to compounds of Formula (I) and stereoisomeric forms thereof, wherein $R^0$ is hydrogen or methyl;

$R^1$ is hydrogen, methyl or ethyl;

X is CH or N;

$A^1$ is CR$^2$ or N;

$A^2$, $A^3$ and $A^4$ each independently are CH or N; provided that no more than two of $A^1$, $A^2$, $A^3$ and $A^4$ are N;

$R^2$ is hydrogen, fluoro or methoxy;

$R^3$ is hydrogen; $C_{1-6}$alkyl optionally substituted with one substituent selected from the group consisting of morpholinyl, piperidinyl, Ar, isopropyloxy, and cyclohexyl; tetrahydropyranyl; Ar; or Ar—O—CH$_2$—;

wherein each Ar independently is phenyl optionally substituted with one or more substituents each independently selected from the group consisting of fluoro, chloro, methoxy, cyano, NR$^5$R$^6$, morpholinyl, methyl, isobutyl, and trifluoromethyl; benzimidazolyl optionally substituted with one or more methyl groups; or pyridinyl;

wherein $R^5$ is ethyl;

wherein $R^6$ is ethyl;

$R^4$ is hydrogen; cyano; chloro; iodo; bromo; phenyl optionally substituted with one or more substituents each independently selected from the group consisting of fluoro and phenyl; phenylcarbonyl optionally substituted with one or more fluoro atoms;

or $C_{1-6}$alkyl;

and the pharmaceutically acceptable addition salts, and the solvates thereof.

In an embodiment, the present invention provides compounds according to any of the other embodiments wherein $R^0$ is hydrogen or $C_{1-4}$alkyl;

$R^1$ is hydrogen, $C_{1-4}$alkyl or halo;

X is CR$^7$ or N; wherein R$^7$ is hydrogen or halo;

$A^1$ is CR$^2$ or N;

$A^2$, $A^3$ and $A^4$ each independently are CH or N; provided that no more than two of $A^1$, $A^2$, $A^3$ and $A^4$ are N;

$R^2$ is hydrogen, halo or $C_{1-4}$alkyloxy;

$R^3$ is hydrogen; $C_{1-6}$alkyl optionally substituted with one or more substituents each independently selected from the group consisting of halo, morpholinyl, piperidinyl, pyrrolidinyl, Ar, $C_{1-6}$alkyloxy, cyclo$C_{3-7}$alkyloxy, and cyclo$C_{3-7}$ alkyl; cyclo$C_{3-7}$alkyl; tetrahydropyranyl; Ar; or Ar—O—CH$_2$—;

each Ar independently is phenyl optionally substituted with one or more substituents each independently selected from the group consisting of halo, $C_{1-4}$alkyloxy, cyano, NR$^5$R$^6$, morpholino, $C_{1-4}$alkyl, and $C_{1-4}$alkyl substituted with one or more substituents selected from halo; benzimidazolyl optionally substituted with one or more substituents each independently selected from $C_{1-4}$alkyl; or pyridinyl optionally substituted with one or more substituents independently selected from the group consisting of halo, $C_{1-4}$alkyloxy, cyano, $C_{1-4}$alkyl, and $C_{1-4}$alkyl substituted with one or more substituents each independently selected from halo;

wherein each $R^5$ independently is hydrogen or $C_{1-4}$alkyl;

wherein each $R^6$ independently is hydrogen or $C_{1-4}$alkyl;

$R^4$ is hydrogen; cyano; halo; phenyl optionally substituted with one or more substituents each independently selected from the group consisting of halo and phenyl; phenylcarbonyl optionally substituted with one or more substituents each independently selected from halo; $C_{1-6}$alkyl optionally substituted with one or more substituents independently selected from $C_{1-4}$alkyloxy; or $C_{1-4}$alkyl substituted with one or more substituents each independently selected from halo.

In another embodiment, the invention concerns compounds of formula (I-a)

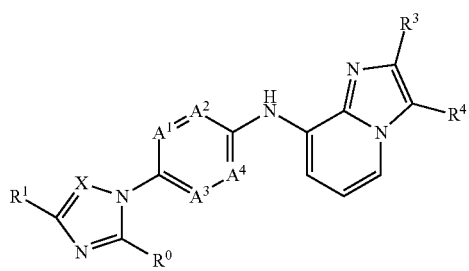

and stereoisomeric forms thereof, wherein
$R^0$ is hydrogen or $C_{1-4}$alkyl;
$R^1$ is hydrogen, $C_{1-4}$alkyl or halo;
X is $CR^7$ or N; wherein $R^7$ is H or halo;
$A^1$ is $CR^2$ or N;
$A^2$, $A^3$ and $A^4$ each independently are CH or N; provided that no more than two of $A^1$, $A^2$, $A^3$ and $A^4$ are N;
$R^2$ is hydrogen, halo or $C_{1-4}$alkyloxy;
$R^3$ is hydrogen; $C_{1-6}$alkyl optionally substituted with one or more substituents selected from halo, morpholino, piperidinyl, pyrrolidinyl, Ar, $C_{1-6}$alkyloxy, cyclo$C_{3-7}$alkyloxy, or cyclo$C_{3-7}$alkyl; cyclo$C_{3-7}$alkyl; tetrahydropyranyl; Ar; or —$CH_2$—O—Ar;
wherein each Ar independently is phenyl optionally substituted with one or more substituents each independently selected from halo, $C_{1-4}$alkyloxy, cyano, $NR^5R^6$, morpholino, $C_{1-4}$alkyl, or $C_{1-4}$alkyl substituted with one or more substituents selected from halo; benzimidazolyl optionally substituted with $C_{1-4}$alkyl; or pyridinyl optionally substituted with 1 or more substituents each independently selected from halo, $C_{1-4}$alkyloxy, cyano, $C_{1-4}$alkyl, or $C_{1-4}$alkyl substituted with one or more substituents selected from halo;
wherein each $R^5$ independently is hydrogen or $C_{1-4}$alkyl;
wherein each $R^6$ independently is hydrogen or $C_{1-4}$alkyl;
$R^4$ is hydrogen; phenyl optionally substituted with halo or phenyl; carbonylphenyl optionally substituted with halo; $C_{1-6}$alkyl optionally substituted with $C_{1-4}$alkyloxy; $C_{1-4}$alkyl substituted with one or more selected from halo; cyano; or halo;
and the pharmaceutically acceptable addition salts, and the solvates thereof.

In another embodiment, the invention relates to compounds according to any of the other embodiments, wherein one or more, preferably all, of the following restrictions apply:
(a) $R^0$ is hydrogen;
(b) $R^1$ is $C_{1-4}$alkyl;
(c) X is CH or N;
(d) $A^1$ is $CR^2$;
(e) $A^2$ is N;
(f) $A^3$ and $A^4$ are CH;
(g) $R^2$ is $C_{1-4}$alkyloxy;
(i) $R^3$ is Ar; or $C_{1-6}$alkyl optionally substituted with one or more substituents each independently selected from halo;
(j) each Ar independently is phenyl optionally substituted with one or more substituents each independently selected from halo;
(k) $R^4$ is hydrogen or $C_{1-6}$alkyl;
(l) $Y^1$ is CH;
(m) $Y^2$ is CH;
(n) $Y^3$ is CH.

In another embodiment, the invention relates to compounds according to any of the other embodiments, wherein one or more, preferably all, of the following restrictions apply:
(a) $R^1$ is methyl;
(b) $R^2$ is methoxy;
(c) $R^3$ is Ar; or $C_{1-6}$alkyl substituted with one or more fluoro atoms;
(d) each Ar independently is phenyl substituted with one or more chloro atoms;
(e) $R^4$ is hydrogen or methyl.

In another embodiment, the invention relates to compounds according to any of the other embodiments, or any combination of the other embodiments wherein $R^3$ is $C_{1-6}$alkyl optionally substituted with one or more substituents each independently selected from halo.

In a next embodiment, the invention relates to compounds according to any of the preceding embodiments, wherein
$R^3$ is phenyl;
$R^4$ is methyl.

In an embodiment, the invention relates to compounds according to any of the preceding embodiments, wherein
$R^3$ is phenyl substituted in a meta position and optionally further substituted in other positions;
$R^4$ is hydrogen or methyl.

In an embodiment, the invention relates to compounds according to any of the preceding embodiments, wherein
$R^3$ is phenyl substituted in an ortho position and optionally further substituted in other positions;
$R^4$ is hydrogen or methyl.

In a further embodiment, the invention relates to compounds according to any of the preceding embodiments, wherein
$R^3$ is methyl substituted with one or more phenyl groups, wherein phenyl is optionally substituted with one or more substituents each independently selected from the group consisting of halo, $C_{1-4}$alkyloxy, cyano, $NR^5R^6$, morpholinyl, $C_{1-4}$alkyl, and $C_{1-4}$alkyl substituted with one or more substituents each independently selected from halo;
$R^4$ is hydrogen.

In an embodiment, the present invention provides compounds according to any of the preceding embodiments, wherein $R^2$ represents $C_{1-4}$alkyloxy, preferably methoxy.

In an embodiment, the present invention provides compounds according to any of the preceding embodiments, wherein $C_{1-6}$alkyl is selected from the group comprising methyl, ethyl, n-propyl, n-butyl, isobutyl and tert-butyl.

In an embodiment, the present invention provides compounds according to any of the preceding embodiments, wherein $C_{1-4}$alkyl is selected from the group comprising methyl, ethyl and n-propyl.

In another embodiment, the present invention relates to compounds according to any of the preceding embodiments, wherein
X is N.

In a further embodiment, the invention relates to compounds according to any of the other embodiments, wherein $Y^1$ is CH or N; $Y^2$ is $CR^4$; and $Y^3$ is CH or N; provided that only one of $Y^1$ and $Y^3$ may represent N.

In a further embodiment, the invention relates to compounds according to any of the other embodiments, wherein $Y^1$ is CH; $Y^2$ is $CR^4$; and $Y^3$ is CH.

In a further embodiment, the invention relates to compounds according to any of the other embodiments, wherein $Y^1$ is CH; $Y^2$ is CH; and $Y^3$ is CH.

In a further embodiment, the invention relates to compounds according to any of the other embodiments, wherein $Y^1$ is N; $Y^2$ is $CR^4$; and $Y^3$ is CH.

In a further embodiment, the invention relates to compounds according to any of the other embodiments, wherein $Y^1$ is CH; $Y^2$ is N; and $Y^3$ is CH.

In a further embodiment, the invention relates to compounds according to any of the other embodiments, wherein $Y^1$ is CH; $Y^2$ is $CR^4$; and $Y^3$ is N.

In a next embodiment, the present invention relates to compound according to any of the preceding embodiments, wherein
$A^1$ represents $CR^2$;
$A^2$, $A^3$ and $A^4$ represents CH.

In an embodiment, the present invention relates to compounds according to any of the preceding embodiments or any combination of the preceding embodiments wherein the compounds are restricted to the compounds of formula (I-a).

In an embodiment the compound of Formula (I) is selected from the group comprising:

2-(4-fluorophenyl)-N-[3-methoxy-4-(4-methyl-1H-imidazol-1-yl)phenyl]-imidazo[1,2-a]pyridin-8-amine, 3-(4-fluorophenyl)-N-[3-methoxy-4-(4-methyl-1H-imidazol-1-yl)phenyl]-imidazo[1,2-a]pyridin-8-amine, 2-(2,4-dimethoxyphenyl)-N-[3-methoxy-4-(4-methyl-1H-imidazol-1-yl)phenyl]-imidazo[1,2-a]pyridin-8-amine, 4-[8-[[3-methoxy-4-(4-methyl-1H-imidazol-1-yl)phenyl]amino]-imidazo[1,2-a]pyridin-2-yl]benzonitrile, N-[3-methoxy-4-(4-methyl-1H-imidazol-1-yl)phenyl]-2-(2-methoxyphenyl)-imidazo[1,2-a]pyridin-8-amine, 2-[4-(diethylamino)phenyl]-N-[3-methoxy-4-(4-methyl-1H-imidazol-1-yl)phenyl]-imidazo[1,2-a]pyridin-8-amine, N-[3-methoxy-4-(4-methyl-1H-imidazol-1-yl)phenyl]-3-methyl-2-phenyl-imidazo[1,2-a]pyridin-8-amine, N-[4-(2,4-dimethyl-1H-imidazol-1-yl)-3-methoxyphenyl]-2-(4-fluorophenyl)-imidazo[1,2-a]pyridin-8-amine, 2-(4-fluorophenyl)-N-[3-methoxy-4-(2-methyl-1H-imidazol-1-yl)phenyl]-imidazo[1,2-a]pyridin-8-amine, 2-[(4-fluorophenyl)methyl]-N-[3-methoxy-4-(4-methyl-1H-imidazol-1-yl)phenyl]-imidazo[1,2-a]pyridin-8-amine.2HCl.2H$_2$O, 2-(4-fluorophenyl)-N-[3-methoxy-4-(4-methyl-1H-imidazol-1-yl)phenyl]-3-propyl-imidazo[1,2-a]pyridin-8-amine.2HCl, N-[3-methoxy-4-(4-methyl-1H-imidazol-1-yl)phenyl]-3-methyl-2-[2-(trifluoromethyl)phenyl]-imidazo[1,2-a]pyridin-8-amine.2HCl, 2-(2-fluorophenyl)-N-[3-methoxy-4-(4-methyl-1H-imidazol-1-yl)phenyl]-3-methyl-imidazo[1,2-a]pyridin-8-amine, 3-ethyl-N-[3-methoxy-4-(4-methyl-1H-imidazol-1-yl)phenyl]-2-propyl-imidazo[1,2-a]pyridin-8-amine, 2-butyl-N-[3-methoxy-4-(4-methyl-1H-imidazol-1-yl)phenyl]-3-propyl-imidazo[1,2-a]pyridin-8-amine, 2-(4-chlorophenyl)-N-[3-methoxy-4-(4-methyl-1H-imidazol-1-yl)phenyl]-imidazo[1,2-a]pyridin-8-amine, N-[3-methoxy-4-(4-methyl-1H-imidazol-1-yl)phenyl]-2-phenyl-imidazo[1,2-a]pyridin-8-amine, N-[3-methoxy-4-(4-methyl-1H-imidazol-1-yl)phenyl]-2-[4-(4-morpholinyl)phenyl]-imidazo[1,2-a]pyridin-8-amine, N-[3-methoxy-4-(4-methyl-1H-imidazol-1-yl)phenyl]-2-(3-methoxyphenyl)-imidazo[1,2-a]pyridin-8-amine, N-[3-methoxy-4-(4-methyl-1H-imidazol-1-yl)phenyl]-2-(4-methoxyphenyl)-imidazo[1,2-a]pyridin-8-amine, N-[3-methoxy-4-(4-methyl-1H-imidazol-1-yl)phenyl]-2-(2-pyridinyl)-imidazo[1,2-a]pyridin-8-amine, N-[3-methoxy-4-(4-methyl-1H-imidazol-1-yl)phenyl]-3-methyl-2-[4-(2-methylpropyl)phenyl]-imidazo[1,2-a]pyridin-8-amine, 2-(2-chlorophenyl)-N-[3-methoxy-4-(4-methyl-1H-imidazol-1-yl)phenyl]-3-methyl-imidazo[1,2-a]pyridin-8-amine, 3-chloro-2-(4-fluorophenyl)-N-[3-methoxy-4-(4-methyl-1H-imidazol-1-yl)phenyl]-imidazo[1,2-a]pyridin-8-amine, 2-(2,4-difluorophenyl)-N-[3-methoxy-4-(4-methyl-1H-imidazol-1-yl)phenyl]-3-methyl-imidazo[1,2-a]pyridin-8-amine, 3-ethyl-2-(4-fluorophenyl)-N-[3-methoxy-4-(4-methyl-1H-imidazol-1-yl)phenyl]-imidazo[1,2-a]pyridin-8-amine, 2-(2,6-difluorophenyl)-N-[3-methoxy-4-(4-methyl-1H-imidazol-1-yl)phenyl]-3-methyl-imidazo[1,2-a]pyridin-8-amine, 2-(2-chlorophenyl)-N-[3-methoxy-4-(4-methyl-1H-imidazol-1-yl)phenyl]-imidazo[1,2-a]pyridin-8-amine, 2-(2,4-difluorophenyl)-N-[3-methoxy-4-(4-methyl-1H-imidazol-1-yl)phenyl]-imidazo[1,2-a]pyridin-8-amine, N-[3-methoxy-4-(4-methyl-1H-imidazol-1-yl)phenyl]-2-(1-methyl-1H-benzimidazol-5-yl)-imidazo[1,2-a]pyridin-8-amine, N-[3-methoxy-4-(4-methyl-1H-imidazol-1-yl)phenyl]-2-[4-(trifluoromethyl)phenyl]-imidazo[1,2-a]pyridin-8-amine, 2-(4-fluorophenyl)-N-[3-methoxy-4-(3-methyl-1H-1,2,4-triazol-1-yl)phenyl]-imidazo[1,2-a]pyridin-8-amine, 3-bromo-2-(4-fluorophenyl)-N-[3-methoxy-4-(4-methyl-1H-imidazol-1-yl)phenyl]-imidazo[1,2-a]pyridin-8-amine, 2-(4-fluorophenyl)-N-[3-methoxy-4-(5-methyl-1H-1,2,4-triazol-1-yl)phenyl]-imidazo[1,2-a]pyridin-8-amine, 2-(1,1-dimethylethyl)-N-[3-methoxy-4-(4-methyl-1H-imidazol-1-yl)phenyl]-imidazo[1,2-a]pyridin-8-amine, N-[3-methoxy-4-(4-methyl-1H-imidazol-1-yl)phenyl]-2-(3-pyridinyl)-imidazo[1,2-a]pyridin-8-amine, 2-(3-fluorophenyl)-N-[3-methoxy-4-(4-methyl-1H-imidazol-1-yl)phenyl]-imidazo[1,2-a]pyridin-8-amine, 2-(3-chlorophenyl)-N-[3-methoxy-4-(4-methyl-1H-imidazol-1-yl)phenyl]-imidazo[1,2-a]pyridin-8-amine, N-[3-methoxy-4-(4-methyl-1H-imidazol-1-yl)phenyl]-2,3-diphenyl-imidazo[1,2-a]pyridin-8-amine, N-[3-methoxy-4-(4-methyl-1H-imidazol-1-yl)phenyl]-2-(3-methoxyphenyl)-3-methyl-imidazo[1,2-a]pyridin-8-amine, N-[4-(1H-imidazol-1-yl)-3-methoxyphenyl]-2-(3-methoxyphenyl)-3-methyl-imidazo[1,2-a]pyridin-8-amine, 2-[(4-fluorophenoxy)methyl]-N-[3-methoxy-4-(4-methyl-1H-imidazol-1-yl)phenyl]-imidazo[1,2-a]pyridin-8-amine, N-[3-methoxy-4-(4-methyl-1H-imidazol-1-yl)phenyl]-2-(tetrahydro-2H-pyran-4-yl)-imidazo[1,2-a]pyridin-8-amine, N-[3-methoxy-4-(4-methyl-1H-imidazol-1-yl)phenyl]-2-(4-pyridinyl)-imidazo-[1,2-a]pyridin-8-amine, 2-(4-fluorophenyl)-N-[3-methoxy-4-(4-methyl-1H-imidazol-1-yl)phenyl]-imidazo[1,2-a]pyrazin-8-amine, 8-[[3-methoxy-4-(4-methyl-1H-imidazol-1-yl)phenyl]amino]-6-(trifluoromethyl)-imidazo[1,2-a]pyridine-2-carboxylic acid ethyl ester.HCl, N-[3-fluoro-4-(5-methyl-1H-1,2,4-triazol-1-yl)phenyl]-2-[2-methyl-5-(trifluoromethyl)phenyl]-imidazo[1,2-a]pyridin-8-amine, 3-[8-[[3-methoxy-4-(3-methyl-1H-1,2,4-triazol-1-yl)phenyl]amino]imidazo[1,2-a]pyridin-2-yl]-4-methyl-benzonitrile, 8-[[3-methoxy-4-(4-methyl-1H-imidazol-1-yl)phenyl]amino]-6-(trifluoromethyl)-imidazo[1,2-a]pyridine-2-carboxylic acid, 2-[(4-fluorophenoxy)methyl]-N-[3-methoxy-4-(3-methyl-1H-1,2,4-triazol-1-yl)phenyl]-6-(trifluoromethyl)-imidazo[1,2-a]pyridin-8-amine, 8-[[3-methoxy-4-(3-methyl-1H-1,2,4-triazol-1-yl)phenyl]amino]-6-(trifluoromethyl)-imidazo[1,2-a]pyridine-2-methanol, 6-bromo-2-(4-fluoro-2-methylphenyl)-N-[3-methoxy-4-(3-methyl-1H-1,2,4-triazol-1-yl)phenyl]-imidazo[1,2-a]pyrazin-8-amine, 2-(4-fluoro-2-methylphenyl)-N-[3-methoxy-4-(3-methyl-1H-1,2,4-triazol-1-yl)phenyl]-imidazo[1,2-a]pyrazin-8-amine, 2-(4-fluoro-2-methylphenyl)-N-[3-fluoro-4-(5-methyl-1H-1,2,4-triazol-1-yl)phenyl]-imidazo[1,2-a]pyridin-8-amine, 2-ethenyl-N-[3-methoxy-4-(3-methyl-1H-1,2,4-triazol-1-yl)phenyl]-6-(trifluoromethyl)-imidazo[1,2-a]pyridin-8-amine, 2-ethyl-N-[3-methoxy-4-(3-methyl-1H-1,2,4-triazol-1-yl)phenyl]-6-(trifluoromethyl)-imidazo[1,2-a]pyridin-8-amine, 2-(2-chlorophenyl)-N-[2-fluoro-4-(3-methyl-1H-1,2,4-triazol-1-yl)phenyl]-3-methyl-imidazo[1,2-a]pyridin-8-amine, 2-[(4-fluorophenyl)methyl]-N-[3-methoxy-4-(3-methyl-1H-1,2,4-triazol-1-yl)phenyl]-6-(trifluoromethyl)-imidazo[1,2-a]pyridin-8-amine, N-[3-methoxy-4-(4-methyl-1H-imidazol-1-yl)phenyl]-2-methyl-6-(trifluoromethyl)-imidazo[1,2-b]pyridazin-8-amine, 2-(4-fluorophenyl)-8-[[3-methoxy-4-(4-methyl-1H-imidazol-1-yl)phenyl]amino]-imidazo[1,2-a]pyridine-3-methanol, N-[3-methoxy-4-(3-methyl-1H-1,2,4-triazol-1-yl)phenyl]-2-(tetrahydro-2H-pyran-4-yl)-imidazo[1,2-a]pyridin-8-amine.1.1HCl.1.5H$_2$O, 2-(4-fluorophenyl)-8-[[3-methoxy-4-(4-methyl-1H-imidazol-1-yl)phenyl]amino]-imidazo[1,2-a]pyridine-3-methanamine, N-[[2-(4-fluorophenyl)-8-[[3-methoxy-4-(4-methyl-1H-imidazol-1-yl)phenyl]amino]imidazo[1,2-a]pyridin-3-yl]methyl]-formamide, 8-[[3-methoxy-4-(4-methyl-1H-imidazol-1-yl)phenyl]amino]-alpha,alpha-dimethyl-6-(trifluoromethyl)-imidazo[1,2-a]pyridine-2-methanol, 2-(4-fluorophenyl)-3-(methoxymethyl)-N-[3-methoxy-4-(3-methyl-1H-1,2,4-triazol-1-yl)phenyl]-imidazo[1,2-a]pyridin-8-amine, 8-[[3-methoxy-4-(3-methyl-1H-1,2,4-triazol-1-yl)phenyl]amino]-6-(trifluoromethyl)-imidazo[1,2-a]pyridine-2-carboxylic acid ethyl ester, N-[3-fluoro-4-(4-methyl-1H-imidazol-1-yl)phenyl]-2-(tetrahydro-2H-pyran-4-yl)-imidazo[1,2-a]pyridin-8-amine.1HCl.0.4H$_2$O, 8-[[3-methoxy-4-(4-methyl-1H-imidazol-1-yl)phenyl]amino]-imidazo[1,2-a]pyridine-2-carboxylic acid ethyl ester, N-[3-fluoro-4-(4-methyl-1H-imidazol-1-yl)phenyl]-2-methyl-6-(trifluoromethyl)-imidazo[1,2-b]pyridazin-8-amine, 6-chloro-N-[3-methoxy-4-(4-methyl-1H-imidazol-1-yl)phenyl]-2-methyl-imidazo[1,2-b]pyridazin-8-amine, 2-(4-fluorophenyl)-N-[3-methoxy-4-(3-methyl-1H-1,2,4-triazol-1-yl)phenyl]-3-(3-methoxypropyl)-imidazo[1,2-a]pyridin-8-amine.1HCl, 2-cyclopropyl-N-[3-fluoro-4-(4-methyl-1H-imidazol-1-yl)phenyl]-imidazo[1,2-a]pyridin-8-amine, 2-cyclopropyl-N-[3-methoxy-4-(3-methyl-1H-1,2,4-triazol-1-yl)phenyl]-imidazo[1,2-a]pyridin-8-amine, 2-cyclopropyl-N-[3-methoxy-4-(4-methyl-1H-imidazol-1-yl)phenyl]-imidazo[1,2-a]pyridin-8-amine, N-[3-methoxy-4-(4-methyl-1H-imidazol-1-yl)phenyl]-2-(tetrahydro-2H-pyran-4-yl)-6-(trifluoromethyl)-imidazo[1,2-b]pyridazin-8-amine, 6-chloro-N-[3-fluoro-4-(4-methyl-1H-imidazol-1-yl)phenyl]-2-(tetrahydro-2H-pyran-4-yl)-imidazo[1,2-a]pyridin-8-amine, 6-fluoro-N-[3-fluoro-4-(4-methyl-1H-imidazol-1-yl)phenyl]-2-(tetrahydro-2H-pyran-4-yl)-imidazo[1,2-a]pyridin-8-amine.1.8HCl.0.9H$_2$O, 2-(4-fluorophenyl)-3-(2-methoxyethyl)-N-[3-methoxy-4-(3-methyl-1H-1,2,4-triazol-1-yl)phenyl]-imidazo[1,2-a]pyridin-8-amine, 2-(4-fluorophenyl)-N-[3-methoxy-4-(3-methyl-1H-1,2,4-triazol-1-yl)phenyl]-imidazo[1,2-a]pyrazin-8-amine, N-[3-methoxy-4-(4-methyl-1H-imidazol-1-yl)phenyl]-2-(2,2,2-trifluoroethyl)-imidazo[1,2-a]pyridin-8-amine, 6-chloro-2-(5-fluoro-2-methylphenyl)-N-[3-methoxy-4-(4-methyl-1H-imidazol-1-yl)phenyl]-imidazo[1,2-b]pyridazin-8-amine, 6-chloro-2-(5-fluoro-2-methylphenyl)-N-[3-methoxy-4-(3-methyl-1H-1,2,4-triazol-1-yl)phenyl]-imidazo[1,2-b]pyridazin-8-amine, 6-chloro-N-[3-fluoro-4-(4-methyl-1H-imidazol-1-yl)phenyl]-2-(5-fluoro-2-methylphenyl)-imidazo[1,2-b]pyridazin-8-amine, 3-[8-[[3-methoxy-4-(4-methyl-1H-imidazol-1-yl)phenyl]amino]imidazo[1,2-a]pyridin-2-yl]-4-methyl-benzonitrile, N-[6-methoxy-5-(4-methyl-1H-imidazol-1-yl)-2-pyridinyl]-3-methyl-2-[2-(trifluoromethyl)phenyl]-imidazo[1,2-a]pyridin-8-amine, N-[3-fluoro-4-(4-methyl-1H-imidazol-1-yl)phenyl]-2-[(tetrahydro-2H-pyran-4-yl)methyl]-imidazo[1,2-a]pyridin-8-amine.1.7HCl.0.25H$_2$O, 2-(4-fluorophenyl)-3-methoxy-N-[3-methoxy-4-(3-methyl-1H-1,2,4-triazol-1-yl)phenyl]-imidazo[1,2-a]pyridin-8-amine, N-[[2-(2-chlorophenyl)-8-[[3-fluoro-4-(4-methyl-1H-imidazol-1-yl)phenyl]amino]imidazo[1,2-a]pyridin-3-yl]methyl]-N-methyl-acetamide, 2-(2-chlorophenyl)-N-[3-methoxy-4-(3-methyl-1H-1,2,4-triazol-1-yl)phenyl]-3-methyl-imidazo[1,2-a]pyridin-8-amine, 2-[5-(aminomethyl)-2-methylphenyl]-N-[3-methoxy-4-(4-methyl-1H-imidazol-1-yl)phenyl]-imidazo[1,2-a]pyridin-8-amine, N-[3-methoxy-4-(3-methyl-1H-1,2,4-triazol-1-yl)phenyl]-2-[(tetrahydro-2H-pyran-4-yl)methyl]-imidazo[1,2-a]pyridin-8-amine.1.8HCl.2.1H$_2$O, 8-[[3-methoxy-4-(3-methyl-1H-1,2,4-triazol-1-yl)phenyl]amino]-N,N-dimethyl-2-phenyl-imidazo[1,2-a]pyridine-3-methanamine, 2-(2-chlorophenyl)-8-[[3-methoxy-4-(3-methyl-1H-1,2,4-triazol-1-yl)phenyl]amino]-N,N-dimethyl-imidazo[1,2-a]pyridine-3-methanamine, N-[3-fluoro-4-(4-methyl-1H-imidazol-1-yl)phenyl]-3-(methoxymethyl)-2-phenyl-imidazo[1,2-a]pyridin-8-amine, 2-(2-chlorophenyl)-N-[3-fluoro-4-(4-methyl-1H-imidazol-1-yl)phenyl]-3-(methoxymethyl)-imidazo[1,2-a]pyridin-8-amine,
N-[6-methoxy-5-(4-methyl-1H-imidazol-1-yl)-2-pyridinyl]-2-methyl-imidazo[1,2-a]pyridin-8-amine,
N-[3-fluoro-4-(4-methyl-1H-imidazol-1-yl)phenyl]-2-methyl-imidazo[1,2-a]pyridin-8-amine,
N-[3-fluoro-4-(4-methyl-1H-imidazol-1-yl)phenyl]-2-(tetrahydro-2H-pyran-4-yl)-6-(trifluoromethyl)-imidazo[1,2-b]pyridazin-8-amine,
6-fluoro-N-[3-fluoro-4-(4-methyl-1H-imidazol-1-yl)phenyl]-2-(4-fluoro-2-methylphenyl)-imidazo[1,2-a]pyridin-8-amine,
N-[6-methoxy-5-(4-methyl-1H-imidazol-1-yl)-2-pyridinyl]-2-(tetrahydro-2H-pyran-4-yl)-imidazo[1,2-a]pyridin-8-amine
2-(5-fluoro-2-methylphenyl)-N-[3-methoxy-4-(4-methyl-1H-imidazol-1-yl)phenyl]-imidazo[1,2-b]pyridazin-8-amine,
2-(5-fluoro-2-methylphenyl)-N-[3-methoxy-4-(3-methyl-1H-1,2,4-triazol-1-yl)phenyl]-imidazo[1,2-b]pyridazin-8-amine,
2-(2-chlorophenyl)-3-(methoxymethyl)-N-[6-methoxy-5-(4-methyl-1H-imidazol-1-yl)-2-pyridinyl]-imidazo[1,2-a]pyridin-8-amine,
N-[[3-[8-[[3-methoxy-4-(4-methyl-1H-imidazol-1-yl)phenyl]amino]imidazo[1,2-a]pyridin-2-yl]-4-methylphenyl]methyl]-propanamide,
N-[3-fluoro-4-(4-methyl-1H-imidazol-1-yl)phenyl]-2-(5-fluoro-2-methylphenyl)-imidazo[1,2-b]pyridazin-8-amine,
8-[[3-methoxy-4-(4-methyl-1H-imidazol-1-yl)phenyl]amino]-alpha,alpha-dimethyl-imidazo[1,2-a]pyridine-2-methanol,
N-[3-methoxy-4-(4-methyl-1H-imidazol-1-yl)phenyl]-2-methyl-imidazo[1,2-b]pyridazin-8-amine,
8-[[3-methoxy-4-(4-methyl-1H-imidazol-1-yl)phenyl]amino]-N,N-dimethyl-imidazo[1,2-a]pyridine-2-carboxamide,
N-[3-fluoro-4-(4-methyl-1H-imidazol-1-yl)phenyl]-2-(4-fluorophenyl)-3-methoxy-imidazo[1,2-a]pyridin-8-amine,
N-[3-methoxy-4-(4-methyl-1H-imidazol-1-yl)phenyl]-6-(2-methoxyphenyl)-2-methyl-imidazo[1,2-b]pyridazin-8-amine,
N-[3-methoxy-4-(4-methyl-1H-imidazol-1-yl)phenyl]-2-methyl-6-(1-methylethyl)-imidazo[1,2-b]pyridazin-8-amine,
N-[3-methoxy-4-(4-methyl-1H-imidazol-1-yl)phenyl]-2-methyl-6-(tetrahydro-2H-pyran-4-yl)-imidazo[1,2-b]pyridazin-8-amine,
8-[[3-methoxy-4-(4-methyl-1H-imidazol-1-yl)phenyl]amino]-imidazo[1,2-a]pyridine-2-carboxylic acid 1-methylethyl ester,
8-[[3-methoxy-4-(4-methyl-1H-imidazol-1-yl)phenyl]amino]-imidazo[1,2-a]pyridine-2-carboxylic acid 1,1-dimethylethyl ester.1.5HCl,
1-[8-[[3-methoxy-4-(4-methyl-1H-imidazol-1-yl)phenyl]amino]imidazo[1,2-a]pyridin-2-yl]-1-propanone.H$_2$O.3HCl,
6-fluoro-N-[6-methoxy-5-(4-methyl-1H-imidazol-1-yl)-2-pyridinyl]-2-(2-methylpropyl)-imidazo[1,2-a]pyridin-8-amine,
2-(4-fluorophenyl)-3-methoxy-N-[6-methoxy-5-(4-methyl-1H-imidazol-1-yl)-2-pyridinyl]-imidazo[1,2-a]pyridin-8-amine,
2-[2-(2-methoxyethoxy)ethoxy]-N-[[3-[8-[[3-methoxy-4-(4-methyl-1H-imidazol-1-yl)phenyl]amino]imidazo[1,2-a]pyridin-2-yl]-4-methylphenyl]methyl]-acetamide.3H$_2$O.1.7HCl,
6-chloro-2-(2-chlorophenyl)-N-[6-methoxy-5-(4-methyl-1H-imidazol-1-yl)-2-pyridinyl]-imidazo[1,2-b]pyridazin-8-amine,
2-(2-chlorophenyl)-N-[6-methoxy-5-(4-methyl-1H-imidazol-1-yl)-2-pyridinyl]-6-(1-methylethenyl)-imidazo[1,2-b]pyridazin-8-amine,
2-(2-chlorophenyl)-N-[6-methoxy-5-(4-methyl-1H-imidazol-1-yl)-2-pyridinyl]-6-(1-methylethyl)-imidazo[1,2-b]pyridazin-8-amine,
2-(1-chloro-2,2,2-trifluoroethyl)-N-[6-methoxy-5-(4-methyl-1H-imidazol-1-yl)-2-pyridinyl]-imidazo[1,2-a]pyridin-8-amine,
2-(2-chlorophenyl)-N-[6-methoxy-5-(4-methyl-1H-imidazol-1-yl)-2-pyridinyl]-3-methyl-imidazo[1,2-a]pyridin-8-amine,
2-(2-chlorophenyl)-N-[6-methoxy-5-(3-methyl-1H-1,2,4-triazol-1-yl)-2-pyridinyl]-3-methyl-imidazo[1,2-a]pyridin-8-amine,
8-[[3-methoxy-4-(4-methyl-1H-imidazol-1-yl)phenyl]amino]-alpha-(trifluoromethyl)-imidazo[1,2-a]pyridine-2-methanol,
N-[6-methoxy-5-(4-methyl-1H-imidazol-1-yl)-2-pyridinyl]-2-(2,2,2-trifluoroethyl)-imidazo[1,2-a]pyridin-8-amine,
N-[6-methoxy-5-(3-methyl-1H-1,2,4-triazol-1-yl)-2-pyridinyl]-2-(2,2,2-trifluoroethyl)-imidazo[1,2-a]pyridin-8-amine
2-(3-methoxyphenyl)-N-[3-methoxy-4-(1H-1,2,4-triazol-1-yl)phenyl]-3-methyl-imidazo[1,2-a]pyridin-8-amine,
2-(3-methoxyphenyl)-3-methyl-N-[5-(4-methyl-1H-imidazol-1-yl)-2-pyridinyl]-imidazo[1,2-a]pyridin-8-amine,
2-butyl-N-[3-methoxy-4-(4-methyl-1H-imidazol-1-yl)phenyl]-imidazo[1,2-a]-pyridin-8-amine.2HCl,
2-butyl-N-[3-methoxy-4-(4-methyl-1H-imidazol-1-yl)phenyl]-imidazo[1,2-a]-pyridin-8-amine,
N-[3-methoxy-4-(4-methyl-1H-imidazol-1-yl)phenyl]-2-[(1-methylethoxy)methyl]-imidazo[1,2-a]pyridin-8-amine.2HCl,
2-(4-fluorophenyl)-3-iodo-N-[3-methoxy-4-(4-methyl-1H-imidazol-1-yl)phenyl]-imidazo[1,2-a]pyridin-8-amine,
N-[4-(4-ethyl-1H-imidazol-1-yl)-3-methoxyphenyl]-2-(3-methoxyphenyl)-3-methyl-imidazo[1,2-a]pyridin-8-amine,
N-[3-methoxy-4-(4-methyl-1H-imidazol-1-yl)phenyl]-imidazo[1,2-a]pyridin-8-amine,
N-[3-methoxy-4-(3-methyl-1H-1,2,4-triazol-1-yl)phenyl]-2-(3-methoxyphenyl)-3-methyl-imidazo[1,2-a]pyridin-8-amine,
N-[3-methoxy-4-(4-methyl-1H-imidazol-1-yl)phenyl]-2-methyl-imidazo[1,2-a]-pyridin-8-amine,
N-[3-methoxy-4-(4-methyl-1H-imidazol-1-yl)phenyl]-2-(1-piperidinylmethyl)-imidazo[1,2-a]pyridin-8-amine,
2-(3-methoxyphenyl)-3-methyl-N-[2-(4-methyl-1H-imidazol-1-yl)-5-pyrimidinyl]-imidazo[1,2-a]pyridin-8-amine,
N-[3-methoxy-4-(4-methyl-1H-imidazol-1-yl)phenyl]-2-(4-morpholinylmethyl)-imidazo[1,2-a]pyridin-8-amine,
2-(4-fluoro-2-methylphenyl)-N-[3-methoxy-4-(4-methyl-1H-imidazol-1-yl)phenyl]-imidazo[1,2-a]pyridin-8-amine,
2-(3-methoxyphenyl)-3-methyl-N-[4-(4-methyl-1H-imidazol-1-yl)phenyl]-imidazo[1,2-a]pyridin-8-amine,
2-(3-methoxyphenyl)-3-methyl-N-[4-(2-methyl-1H-imidazol-1-yl)phenyl]-imidazo[1,2-a]pyridin-8-amine, N-[3-methoxy-4-(4-methyl-1H-imidazol-1-yl)phenyl]-2-[2-(trifluoromethyl)phenyl]-imidazo[1,2-a]pyridin-8-amine,
N-[3-methoxy-4-(4-methyl-1H-imidazol-1-yl)phenyl]-2-[3-(trifluoromethyl)phenyl]-imidazo[1,2-a]pyridin-8-amine,
3-hexyl-N-[3-methoxy-4-(4-methyl-1H-imidazol-1-yl)phenyl]-imidazo[1,2-a]-pyridin-8-amine,
N-[3-fluoro-4-(4-methyl-1H-imidazol-1-yl)phenyl]-2-(3-methoxyphenyl)-3-methyl-imidazo[1,2-a]pyridin-8-amine,
2-(4-fluorophenyl)-8-[[3-methoxy-4-(4-methyl-1H-imidazol-1-yl)phenyl]amino]-imidazo[1,2-a]pyridine-3-carbonitrile,
3-[1,1'-biphenyl]-2-yl-N-[3-methoxy-4-(4-methyl-1H-imidazol-1-yl)phenyl]-imidazo[1,2-a]pyridin-8-amine,
3-chloro-2-(cyclohexylmethyl)-N-[3-methoxy-4-(4-methyl-1H-imidazol-1-yl)phenyl]-imidazo[1,2-a]pyridin-8-amine,
(4-fluorophenyl)[8-[[3-methoxy-4-(4-methyl-1H-imidazol-1-yl)phenyl]amino]-imidazo[1,2-a]pyridin-3-yl]-methanone,
3-[1,1'-biphenyl]-3-yl-N-[3-methoxy-4-(4-methyl-1H-imidazol-1-yl)phenyl]-imidazo[1,2-a]pyridin-8-amine,
2-methyl-N-[4-(3-methyl-1H-1,2,4-triazol-1-yl)phenyl]-imidazo[1,2-a]pyridin-8-amine,
2-(2-methylphenyl)-N-[4-(3-methyl-1H-1,2,4-triazol-1-yl)phenyl]-imidazo[1,2-a]-pyridin-8-amine,
N-[3-methoxy-4-(3-methyl-1H-1,2,4-triazol-1-yl)phenyl]-2-(2-methylphenyl)-imidazo[1,2-a]pyridin-8-amine,
2-(5-fluoro-2-methylphenyl)-N-[3-methoxy-4-(3-methyl-1H-1,2,4-triazol-1-yl)phenyl]-imidazo[1,2-a]pyridin-8-amine,
N-[4-(3-methyl-1H-1,2,4-triazol-1-yl)phenyl]-2-[2-methyl-5-(trifluoromethyl)-phenyl]-imidazo[1,2-a]pyridin-8-amine,
2-(2-fluorophenyl)-N-[3-methoxy-4-(4-methyl-1H-imidazol-1-yl)phenyl]-imidazo[1,2-a]pyridin-8-amine,
N-[3-methoxy-4-(3-methyl-1H-1,2,4-triazol-1-yl)phenyl]-2-methyl-imidazo[1,2-a]-pyridin-8-amine,
2-(2-methylphenyl)-N-[6-(3-methyl-1H-1,2,4-triazol-1-yl)-3-pyridinyl]-imidazo-[1,2-a]pyridin-8-amine,
2,3-dimethyl-N-[4-(3-methyl-1H-1,2,4-triazol-1-yl)phenyl]-imidazo[1,2-a]pyridin-8-amine,
2-(2-chlorophenyl)-3-methyl-N-[5-(3-methyl-1H-1,2,4-triazol-1-yl)-2-pyridinyl]-imidazo[1,2-a]pyridin-8-amine,
N-[3-methoxy-4-(1H-1,2,4-triazol-1-yl)phenyl]-2-methyl-imidazo[1,2-a]pyridin-8-amine,
2-butyl-N-[4-(3-methyl-1H-1,2,4-triazol-1-yl)phenyl]-imidazo[1,2-a]pyridin-8-amine.2HCl,
2-(2-chlorophenyl)-3-methyl-N-[6-(3-methyl-1H-1,2,4-triazol-1-yl)-3-pyridinyl]-imidazo[1,2-a]pyridin-8-amine,
N-[5-(3-methyl-1H-1,2,4-triazol-1-yl)-2-pyridinyl]-2-[2-methyl-5-(trifluoromethyl)-phenyl]-imidazo[1,2-a]pyridin-8-amine,
2-(2-methylphenyl)-N-[5-(3-methyl-1H-1,2,4-triazol-1-yl)-2-pyridinyl]-imidazo-[1,2-a]pyridin-8-amine,
2-(5-fluoro-2-methylphenyl)-N-[6-(3-methyl-1H-1,2,4-triazol-1-yl)-3-pyridinyl]-imidazo[1,2-a]pyridin-8-amine,
2-(4-fluoro-2-methylphenyl)-N-[6-(3-methyl-1H-1,2,4-triazol-1-yl)-3-pyridinyl]-imidazo[1,2-a]pyridin-8-amine,
N-[6-(3-methyl-1H-1,2,4-triazol-1-yl)-3-pyridinyl]-2-[2-methyl-5-(trifluoromethyl)-phenyl]-imidazo[1,2-a]pyridin-8-amine,
N-[4-(5-methyl-1H-1,2,4-triazol-1-yl)phenyl]-2-[2-methyl-5-(trifluoromethyl)-phenyl]-imidazo[1,2-a]pyridin-8-amine,
N-[3-fluoro-4-(3-methyl-1H-1,2,4-triazol-1-yl)phenyl]-2-[2-methyl-5-(trifluoromethyl)phenyl]-imidazo[1,2-a]pyridin-8-amine,
2-(4-fluoro-2-methylphenyl)-N-[3-methoxy-4-(3-methyl-1H-1,2,4-triazol-1-yl)phenyl]-imidazo[1,2-a]pyridin-8-amine, 2-(4-fluoro-2-methylphenyl)-N-[4-(3-methyl-1H-1,2,4-triazol-1-yl)phenyl]-imidazo[1,2-a]pyridin-8-amine, 2-(4-fluoro-2-methylphenyl)-N-[3-fluoro-4-(3-methyl-1H-1,2,4-triazol-1-yl)phenyl]-imidazo[1,2-a]pyridin-8-amine, and N-[3-fluoro-4-(3-methyl-1H-1,2,4-triazol-1-yl)phenyl]-2-(5-methoxy-2-methylphenyl)-imidazo[1,2-a]pyridin-8-amine, including any stereochemically isomeric form thereof,
and the pharmaceutically acceptable addition salts and the solvates thereof.

In an embodiment the compound of Formula (I) is 2-(2-chlorophenyl)-N-[6-methoxy-5-(3-methyl-1H-1,2,4-triazol-1-yl)-2-pyridinyl]-3-methyl-imidazo[1,2-a]pyridin-8-amine, including any stereochemically isomeric form thereof, and the pharmaceutically acceptable addition salts and the solvates thereof.

In an embodiment the compound of Formula (I) is N-[6-methoxy-5-(4-methyl-1H-imidazol-1-yl)-2-pyridinyl]-2-(2,2,2-trifluoroethyl)-imidazo[1,2-a]pyridin-8-amine, including any stereochemically isomeric form thereof, and the pharmaceutically acceptable addition salts and the solvates thereof.

In an embodiment the compound of Formula (I) is N-[6-methoxy-5-(3-methyl-1H-1,2,4-triazol-1-yl)-2-pyridinyl]-2-(2,2,2-trifluoroethyl)-imidazo[1,2-a]pyridin-8-amine, including any stereochemically isomeric form thereof, and the pharmaceutically acceptable addition salts and the solvates thereof.

The present invention also encompasses processes for the preparation of compounds of Formula (I) and subgroups thereof. In the reactions described, it can be necessary to protect reactive functional groups, for example hydroxy, amino, or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1999.

The compounds of Formula (I) and the subgroups thereof can be prepared by a succession of steps as described hereunder. They are generally prepared from starting materials which are either commercially available or prepared by standard means obvious to those skilled in the art. The compounds of the present invention can be also prepared using standard synthetic processes commonly used by those skilled in the art of organic chemistry.

The general preparation of some typical examples is shown below:

Experimental Procedure 1

In general, compounds of formula (I), can be prepared as set out below in Scheme 1 wherein halo is defined as Br, Cl or I, and wherein all other variables are defined as hereabove:

Scheme 1

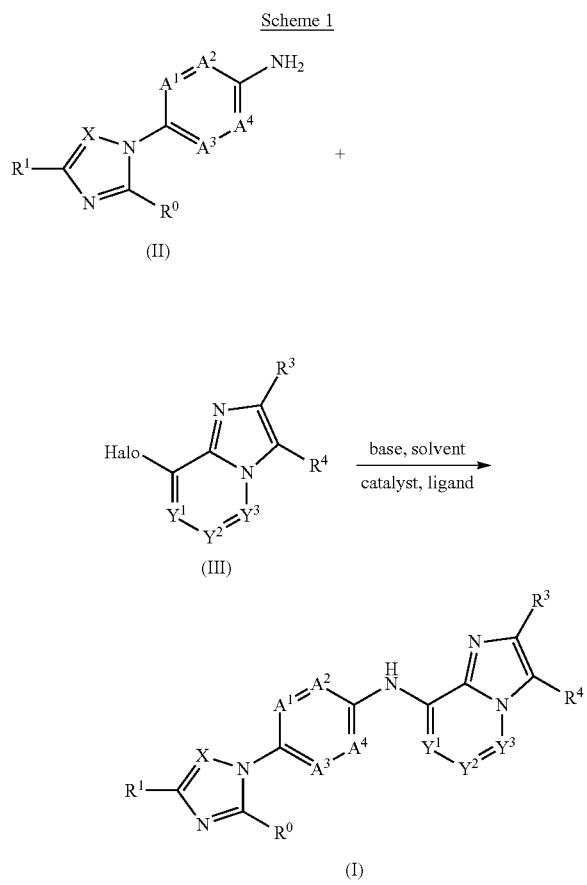

Compounds of formula (I) can be prepared via a coupling reaction between an intermediate of formula (II) and formula (III). This reaction may be performed in the presence of a suitable base such as, for example, $Cs_2CO_3$ or sodium tert-butoxide. The reaction can be performed in a reaction-inert solvent such as, for example, toluene, N,N-dimethylformamide (DMF), tert-butanol or dioxane. The reaction typically is performed in the presence of a catalyst system comprising a suitable catalyst such as palladium(II) acetate($Pd(OAc)_2$) or tris(dibenzylideneacetone)dipalladium ($Pd_2(dba)_3$) and a ligand such as (9,9-dimethyl-9H-xanthene-4,5-diyl)bis[diphenylphosphine](Xantphos), [1,1'-binaphthalene]-2,2'-diylbis[diphenylphosphine] (BINAP), or dicyclohexyl[2',4',6'-tris(1-methylethyl)[1,1'-biphenyl]-2-yl]-phosphine (X-phos). Preferably this reaction is carried out under an inert atmosphere, such as a nitrogen or an argon atmosphere. Reaction rate and yield may be enhanced by microwave assisted heating. For compounds of formula (I), where $Y^1=N$, no catalyst may be required, and couplings can also be performed under acidic conditions, for example using HCl or methanesulfonic acid in an alcoholic solvent such as 2-propanol.

Experimental Procedure 2

Compounds of formula (I) wherein X represents CH and wherein $R^0$ represents H, hereby named compounds of formula (I-x), can also be prepared via a condensation reaction of intermediate (IV) with an ammonia source such as, for example, ammonium acetate($NH_4(OAc)$) to yield compounds of formula (I-x).

Scheme 2

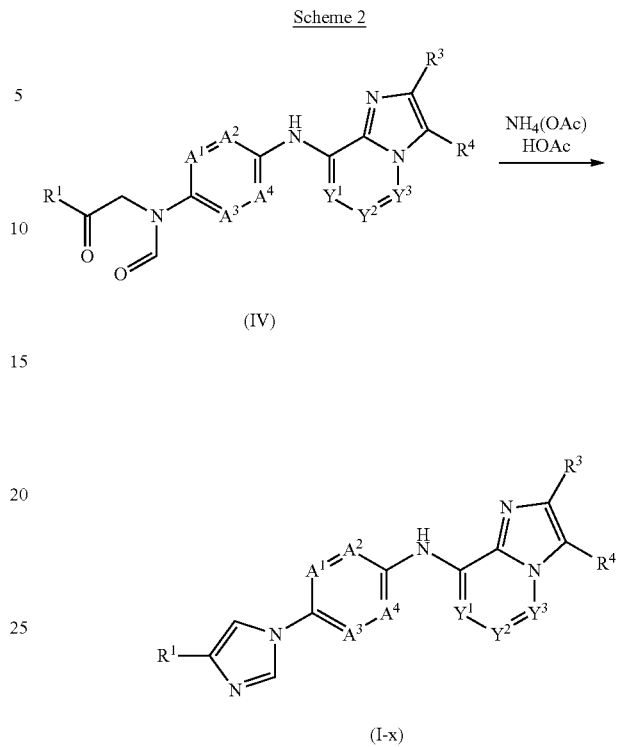

Compounds of formula (I) or formula (I-x) wherein $R^4$ represents hydrogen, can be further derivatized towards other $R^4$ groups via electrophilic aromatic substitution reactions, such as halogenation (such as, for example, chlorination or bromination). The obtained compounds (I) or (I-x) wherein $R^4$ represents halo can be further derivatized to other $R^4$ groups. Both $R^3$ and $R^4$ groups containing suitable functional groups such as, for example, halo, (protected) amines, alcohols or ketones, can be used to incorporate further substitution patterns in compounds of formula (I) or formula (I-x).

Experimental Procedure 3

An intermediate of formula (II) can be prepared by reduction of an intermediate of formula (V) as is shown in Scheme 3, wherein all variables are as defined before. The reduction of (V) to (II) can be conducted by a conventional method such as, for example, a reductive hydrogenation or reduction with a metal or a metal salt and an acid [for example a metal such as iron or a metal salt such as $SnCl_2$ and acid such as an inorganic acid (hydrochloric acid, sulfuric acid or the like) or an organic acid (acetic acid or the like)], or other well-known methods for converting a nitro-group to the corresponding amine.

Scheme 3

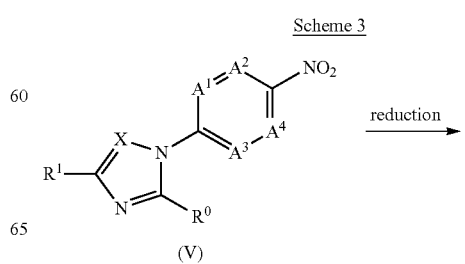

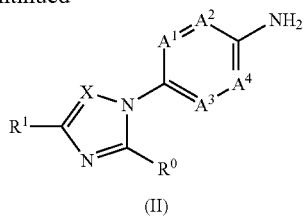

(II)

Experimental Procedure 4

An intermediate of formula (II) can also be prepared by a copper catalysed reaction of an intermediate of formula (VI) with an optionally substituted imidazole or triazole of formula (VII), according to Scheme 4. In Scheme 4, halo is defined as Br or I and all other variables are defined as mentioned hereabove. The reaction may be performed under a protecting atmosphere such as, for example, a $N_2$ atmosphere. Stirring, elevated temperatures (for example between 70-200° C.) and/or pressure may enhance the rate of the reaction. The reaction typically is performed in an organic solvent such as, for example, dimethylsulfoxide (DMSO) or DMF. The reaction may performed in the presence of a base such as, for example $K_2CO_3$, $Cs_2CO_3$ or triethylamine ($Et_3N$). The reaction may be performed in the presence of a ligand such as N,N'-dimethylethylenediamine or 1,10-phenanthroline. Typical copper catalysts that can be used in this reaction in catalytic or stoichiometric amounts, are copper salts such as, for example, copper(I)oxide, copper(I)iodide or copper(I)bromide. The amino-group in intermediate (VI) can be protected before reaction (and deprotected after reaction) via the use of a suitable amino-protecting group in accordance with standard practice, for example, see T. W. Greene and P. G. M. Wuts in "Protective Groups in Organic Chemistry", John Wiley and Sons, 1999.

Scheme 4

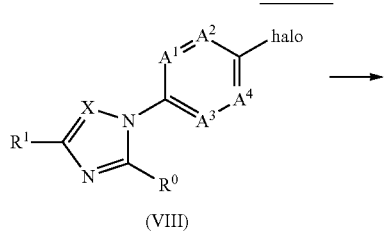

Intermediates according to formula (VI) or (VII) are commercially available or can be prepared by those skilled in the art.

Experimental Procedure 5

Alternatively, an intermediate of formula (II) can also be prepared by conversion of the halo-substituent in an intermediate of formula (VIII), wherein halo is defined as Br or I, and wherein all other variables are defined as mentioned hereabove, into an amino-group or a masked amino functionality, which can subsequently be converted into an amino-group, according to Scheme 5.

Scheme 5

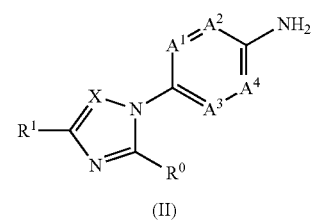

(II)

Experimental Procedure 6

An intermediate of formula (V) can be prepared via a nucleophilic aromatic substitution of an intermediate (IX) with an optionally substituted imidazole or triazole of formula (VII) according to Scheme 6, wherein halo is defined as F, Cl, or Br and wherein all other variables are defined as mentioned hereabove. The reaction may be performed under a protecting atmosphere such as, for example, $N_2$ atmosphere. Stirring, elevated temperatures (for example between 70-170° C.) and/or increased pressure may enhance the rate of the reaction. The reaction typically may be performed in an organic solvent such as, for example, DMSO, DMF or N-methylpyrrolidinone (NMP) in the presence of a base such as, for example, $K_2CO_3$, $Cs_2CO_3$, or $Et_3N$.

Scheme 6

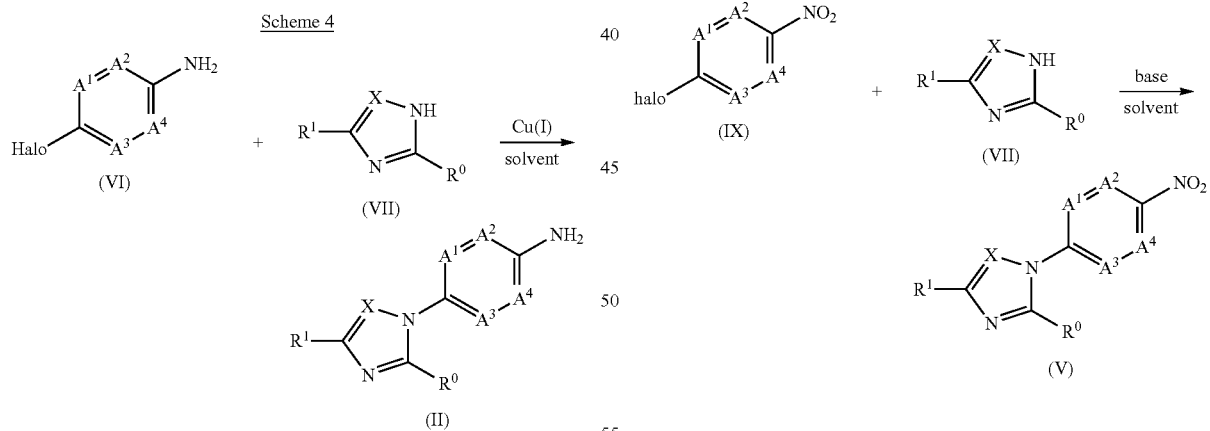

Intermediates of formula (IX) and formula (VII) are commercially available or can be prepared by those skilled in the art.

Experimental Procedure 7

An intermediate of formula (VIII) wherein at least one of $A^1$ or $A^3$ represents N, hereby named an intermediate of formula (VIII-a), can be prepared via a nucleophilic aromatic substitution of an intermediate of formula (X), wherein at least one of $A^1$ or $A^3$ represents N, with an optionally substituted imidazole or triazole of formula (VII) according to Scheme 7, wherein halo$^2$ is defined as F, Cl or Br, wherein halo is defined as Br or I, and wherein all other substituents are defined as mentioned before. The reaction may be performed under similar conditions as described for Experimental procedure 6.

Scheme 7

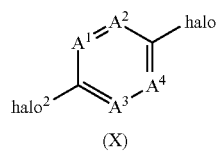

(X)

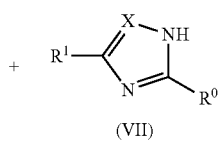

(VII)

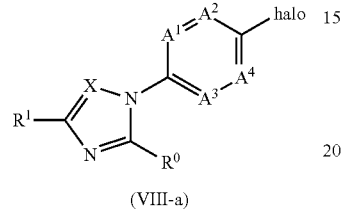

(VIII-a)

Experimental Procedure 8

An intermediate of formula (III) can be prepared via a condensation reaction between an intermediate of formula (XI) and an intermediate of formula (XVII) as is illustrated in Scheme 8, wherein halo² is restricted to Br and Cl, and wherein all other variables are defined as hereabove. The reaction may be performed in a reaction-inert solvent such as, for example, ethanol or n-butanol, or by mixing the reagents without a solvent. The reaction may conveniently be carried out at elevated temperatures ranging between 50° C. and the reflux temperature of the reaction mixture. Reaction rate and yield may be enhanced by microwave assisted heating.

Scheme 8

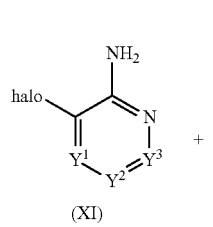

(XI)

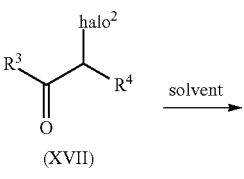

(XVII)

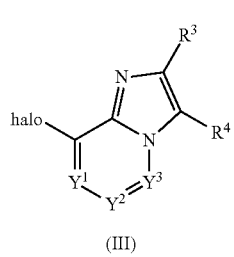

(III)

Experimental Procedure 9

An intermediate of formula (XII) can be formylated to yield intermediate (IV) according to Scheme 9, wherein all substituents are defined as mentioned hereabove. A formylation reaction can be performed in the presence of an acid anhydride such as, for example, acetic anhydride ($Ac_2O$). Typically, the reaction may be performed in the presence of a solvent such as, for example, formic acid (HCOOH).

Scheme 9

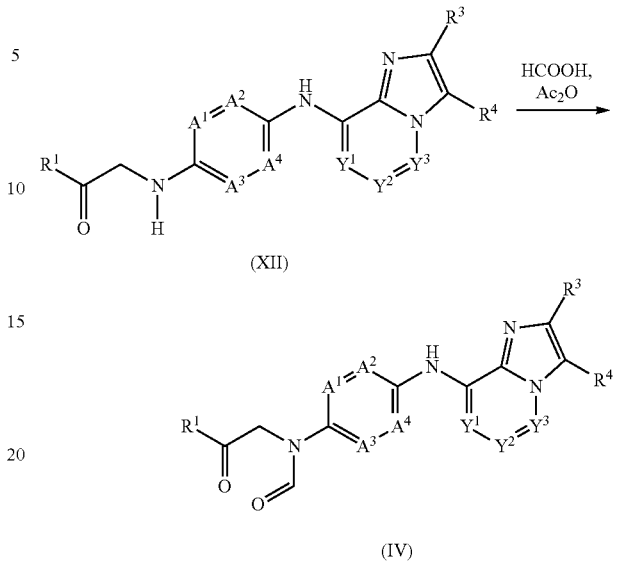

(XII)

(IV)

Experimental Procedure 10

An intermediate of formula (XII) can be prepared via a coupling reaction between an intermediate of formula (XIII) and an intermediate of formula (III) under similar conditions as described for experimental procedure 1. In Scheme 10, R represents H or trifluoromethylcarbonyl ($CF_3C(O)$) and all other substituents are defined as before.

Scheme 10

R = H or $CF_3C(O)$
(XIII)

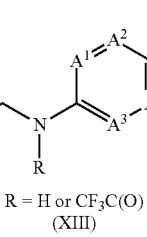

(III)

(XII)

Experimental Procedure 11

An intermediate of formula (XIII) can be prepared by reduction of an intermediate of formula (XIV) according to Scheme 11. This reaction can be performed using a conventional method such as, for example, a reductive hydrogenation or reduction with a metal or a metal salt and an acid [for example a metal such as iron, or a metal salt such as SnCl2 and acid such as an inorganic acid (hydrochloric acid, sulfuric acid or the like) or an organic acid (acetic acid or the like)], or other well-known methods for converting a nitro-group to the corresponding amine. In Scheme 11, R represents H or trifluoromethylcarbonyl ($CF_3C(O)$) and all other substituents are defined as before.

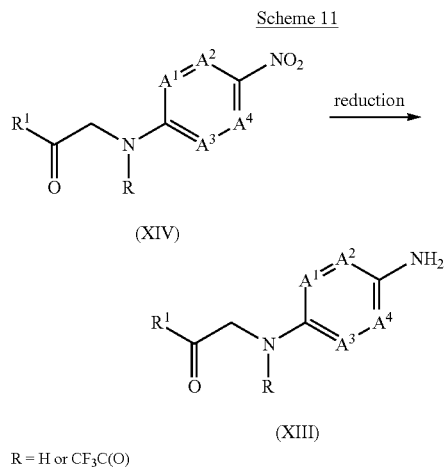

EXPERIMENTAL PROCEDURE 12

An intermediate of formula (XIV), can be prepared via alkylation of intermediate (XVI) with an intermediate of formula (XV), wherein halo is defined as Cl or Br, in the presence of a reaction inert solvent such as, for example, DMF, and a suitable base such as, for example, $Cs_2CO_3$ or $K_2CO_3$. In Scheme 12, R represents H or trifluoromethylcarbonyl ($CF_3C(O)$) and all other substituents are defined as before.

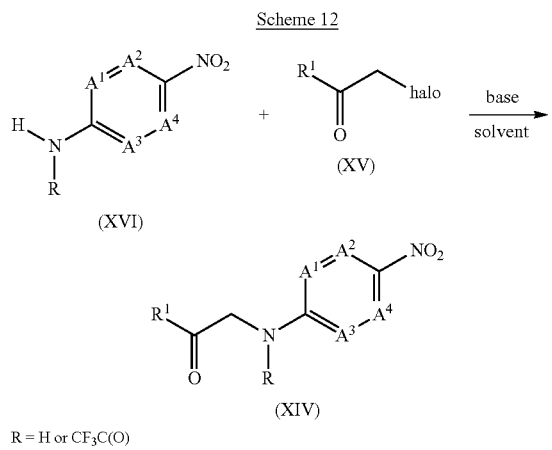

Intermediates of formula (VI), (VII), (IX), (X), (XI), (XV), (XVI) and formula (XVII) are commercially available or can be prepared by those skilled in the art.

Where necessary or desired, any one or more of the following further steps in any order may be performed:

Compounds of Formula (I) or (III), any subgroup thereof, addition salts, solvates, and stereochemical isomeric forms thereof can be converted into further compounds according to the invention using procedures known in the art.

It will be appreciated by those skilled in the art that in the processes described above the functional groups of intermediate compounds may need to be blocked by protecting groups. In case the functional groups of intermediate compounds were blocked by protecting groups, they can be deprotected after a reaction step.

Pharmacology

It has been found that the compounds of the present invention modulate the γ-secretase activity. The compounds according to the invention and the pharmaceutically acceptable compositions thereof are therefore useful in the treatment or prevention of Alzheimer's disease (AD), traumatic brain injury, mild cognitive impairment (MCI), senility, dementia, dementia with Lewy bodies, cerebral amyloid angiopathy, multi-infarct dementia, Down's syndrome, dementia associated with Parkinson's disease and dementia associated with beta-amyloid, preferably Alzheimer's disease.

As used herein, the term "modulation of γ-secretase activity" refers to an effect on the processing of APP by the γ-secretase-complex. Preferably it refers to an effect in which the overall rate of processing of APP remains essentially as without the application of said compounds, but in which the relative quantities of the processed products are changed, more preferably in such a way that the amount of the Aβ42-peptide produced is reduced. For example a different Abeta species can be produced (e.g. Abeta-38 or other Abeta peptide species of shorter amino acid sequence instead of Abeta-42) or the relative quantities of the products are different (e.g. the ratio of Abeta-40 to Abeta-42 is changed, preferably increased).

It has been previously shown that the γ-secretase complex is also involved in the processing of the Notch-protein. Notch is a signaling protein which plays a crucial role in developmental processes (e.g. reviewed in Schweisguth F (2004) Curr. Biol. 14, R129). With respect to the use of γ-secretase modulators in therapy, it seems particularly advantageous not to interfere with the Notch-processing activity of the γ-secretase activity in order to avoid putative undesired side-effects. While γ-secretase inhibitors show side effects due to concomitant inhibition of Notch processing, γ-secretase modulators may have the advantage of selectively decreasing the production of highly aggregatable and neurotoxic forms of Aβ, i.e. Aβ42. Thus, compounds are preferred which do not show an effect on the Notch-processing activity of the γ-secretase-complex.

As used herein, the term "treatment" is intended to refer to all processes, wherein there may be a slowing, interrupting, arresting, or stopping of the progression of a disease, but does not necessarily indicate a total elimination of all symptoms.

The invention relates to a compound according to the general Formula (I), the stereoisomeric forms thereof and the pharmaceutically acceptable acid or base addition salts and the solvates thereof, for use as a medicament.

The invention also relates to a compound according to the general Formula (I), the stereoisomeric forms thereof and the pharmaceutically acceptable acid or base addition salts and the solvates thereof, for the treatment or prevention of diseases or conditions selected from Alzheimer's disease (AD), traumatic brain injury, mild cognitive impairment (MCI), senility, dementia, dementia with Lewy bodies, cerebral amyloid angiopathy, multi-infarct dementia, or Down's syndrome.

In an embodiment, said disease or condition is preferably Alzheimer's disease.

The invention also relates to a compound according to the general Formula (I), the stereoisomeric forms thereof and the pharmaceutically acceptable acid or base addition salts and the solvates thereof, for the treatment of said diseases.

The invention also relates to a compound according to the general formula (I), the stereoisomeric forms thereof and the pharmaceutically acceptable acid or base addition salts and the solvates thereof, for the treatment or prevention, in particular treatment, of γ-secretase mediated diseases or conditions.

The invention also relates to the use of a compound according to the general Formula (I), the stereoisomeric forms thereof and the pharmaceutically acceptable acid or base addition salts and the solvates thereof, for the manufacture of a medicament.

The invention also relates to the use of a compound according to the general Formula (I), the stereoisomeric forms thereof and the pharmaceutically acceptable acid or base addition salts and the solvates thereof, for the manufacture of a medicament for the modulation of γ-secretase activity.

The invention also relates to the use of a compound according to the general Formula (I), the stereoisomeric forms thereof and the pharmaceutically acceptable acid or base addition salts and the solvates thereof, for the manufacture of a medicament for the treatment or prevention of any one of the disease conditions mentioned hereinbefore.

The invention also relates to the use of a compound according to the general Formula (I), the stereoisomeric forms thereof and the pharmaceutically acceptable acid or base addition salts and the solvates thereof, for the manufacture of a medicament for the treatment of any one of the disease conditions mentioned hereinbefore.

In the invention, particular preference is given to compounds of Formula (I), or any subgroup thereof with a $IC_{50}$ value for the inhibition of the production of Aβ42-peptide of less than 1000 nM, preferably less than 100 nM, more preferably less than 50 nM, even more preferably less than 20 nM as determined by a suitable assay, such as the assays used in the Examples below.

The compounds of the present invention can be administered to mammals, preferably humans for the treatment or prevention of any one of the diseases mentioned hereinbefore.

In view of the utility of the compound of Formula (I), there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I), a stereoisomeric form thereof and a pharmaceutically acceptable addition salt or solvate thereof, to warm-blooded animals, including humans.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that are suitable to treat or prevent Alzheimer's disease or the symptoms thereof, may be administered alone or in combination with one or more additional therapeutic agents. Combination therapy includes administration of a single pharmaceutical dosage formulation which contains a compound of Formula (I) and one or more additional therapeutic agents, as well as administration of the compound of Formula (I) and each additional therapeutic agents in its own separate pharmaceutical dosage formulation. For example, a compound of Formula (I) and a therapeutic agent may be administered to the patient together in a single oral dosage composition such as a tablet or capsule, or each agent may be administered in separate oral dosage formulations.

While it is possible for the active ingredient to be administered alone, it is preferable to present it as a pharmaceutical composition.

Accordingly, the present invention further provides a pharmaceutical composition comprising a pharmaceutically acceptable carrier and, as active ingredient, a therapeutically effective amount of a compound according to Formula (I).

The carrier or diluent must be "acceptable" in the sense of being compatible with the other ingredients of the composition and not deleterious to the recipients thereof.

For ease of administration, the subject compounds may be formulated into various pharmaceutical forms for administration purposes. The compounds according to the invention, in particular the compounds according to Formula (I), a pharmaceutically acceptable acid or base addition salt thereof, a stereochemically isomeric form thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing compounds of Formula (I) may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally administrable compounds, pharmaceutical compositions comprising said compounds for administration orally are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of formula (I), and, from 1 to 99.95% by weight, more preferably from 30 to 99.9% by weight, even more preferably from 50 to 99.9% by weight of a pharmaceutically acceptable carrier, all percentages being based on the total weight of the composition.

The following examples illustrate the present invention.

EXAMPLES

Hereinafter, the term "DCM" means dichloromethane; "MeOH" means methanol; "LCMS" means Liquid Chromatography/Mass spectrometry; "HPLC" means high-performance liquid chromatography; "r.t." means room temperature; "AcOH" means acetic acid; "m.p." means melting point; "RP" means reversed phase; "q.s." means quantum suffice; "BDS" means base deactivated silica; "min" means minute(s); "h" means hour(s); "I.D." means internal diameter; "EtOAc" means ethyl acetate; "Ac$_2$O" means acetic anhydride; "Et$_3$N" means triethylamine; "BINAP" means [1,1'-binaphthalene]-2,2'-diylbis-[diphenylphosphine] (racemic); "sat." means saturated; "aq." means aqueous; "Et$_2$O" means diethyl ether; "EtOH" means ethanol; "eq" means equivalent; "DAPCy catalyst" means (SP-4-1)-bis(acetato-κO)bis(N-cyclohexyl-cyclohexanamine)palladium, also named trans-bis(dicyclohexyl-amine)palladium-diacetate; "DME" means 1,2-dimethoxyethane; "DIPE" means diisopropyl ether; "r.m." means reaction mixture(s); "DMA" means N,N-dimethylacetamide; "NMP" means N-methyl-2-pyrrolidinone, "THF" means tetrahydrofuran, "DMSO" means dimethyl sulfoxide; "w/v' means weight/volume; "DMF" means N,N-dimethyl formamide; "DIPEA" means diisopropylethylamine; "KOtBu" means potassium tert-butoxide; "NaOMe" means sodium methoxide; "mCPBA" means meta-chloroperbenzoic acid; "PPh3" means triphenylphosphine; "HBTU" means O-(benzotriazol-1-yl)-N,N,N',N'-tetramethyluronium hexafluoro-phosphate; "X-phos" means dicyclohexyl[2',4',6'-tris(1-methylethyl)[1,1'-biphenyl]-2-yl]phosphine; "DIBAH" means diisobutylaluminum hydride; "KOAc" means potassium acetate; and "Pd$_2$(dba)$_3$" means tris[μ-[(1,2-η:4,5-η)-(1E,4E)-1,5-diphenyl-1,4-pentadien-3-one]]dipalladium.

A. Preparation of the Intermediates

Example A1 a) Preparation of Intermediate 1

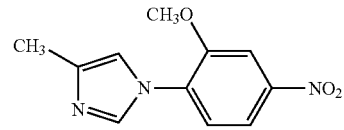

A mixture of 1-chloro-2-methoxy-4-nitrobenzene (50 g, 0.26 mol), 4-methyl-1H-imidazole (43.77 g, 0.53 mol) and K$_2$CO$_3$ (36.84 g, 0.26 mol) in DMSO (500 ml) was reacted in an autoclave under a N$_2$ atmosphere for 6 h at 150° C. This reaction was performed 3 times with 50 g of 1-chloro-2-methoxy-4-nitrobenzene. Subsequently, the three r.m. were worked up together. The mixture was poured into 6l of ice-water. The solid was filtered off and washed with H$_2$O. The solid was dissolved in DCM and this solution was washed with H$_2$O. The separated organic layer was dried (MgSO$_4$), filtered and the solvent was evaporated in vacuo. The residue was purified over silicagel on a glass filter (eluent: DCM/MeOH from 100/0 to 97/3). The product fractions were collected and the solvent was evaporated. The residue was suspended in DIPE, filtered off and dried in the oven. Yield: 48.54 g of intermediate 1 (26.0%).

b) Preparation of Intermediate 2a and Intermediate 2

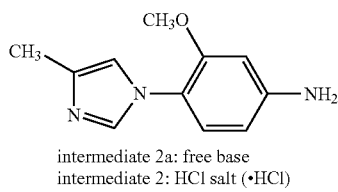

intermediate 2a: free base
intermediate 2: HCl salt (•HCl)

Intermediate 1 (13.2 g, 56.6 mmol) was dissolved in MeOH (250 ml). Pd/C (0.5 g) was added to the solution and the resulting suspension was stirred at 50° C. under $H_2$ (atmospheric pressure) overnight. After uptake of $H_2$ (1 eq), the catalyst was filtered off. The organic layer was evaporated, yielding intermediate 2a (free base). Intermediate 2a was dissolved in a solution of HCl/EtOH and stirred for 30 min. The solvent was removed in vacuo. The residue was crystallized from EtOH with petroleum ether (q.s.) to yield the desired product. Yield: 4.7 g of intermediate 2 (41.0%).

Example A2 a) Preparation of Intermediate 3

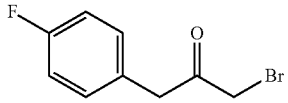 [SMILES: O=C(CBr)Cc1ccc(F)cc1]

A solution of bromine (10.49 g, 65.67 mmol) in AcOH (15 ml) was added to a solution of 1-(4-fluorophenyl)-2-propanone (4.54 g, 29.85 mmol) in AcOH (10 ml) and a 48% HBr solution (5 ml). The r.m. was stirred for 6 h at r.t. Subsequently, acetone (50 ml) was added and the mixture was stirred overnight at r.t. The mixture was concentrated in vacuo and extracted with DCM. The organic layer was dried (MgSO$_4$) and concentrated in vacuo overnight. The residue was purified by column chromatography (eluent: EtOAc/heptane 5/95). The product fractions were collected and the solvent was evaporated in vacuo. Yield: 5.00 g of intermediate 3 (72.5%).

b) Preparation of Intermediate 4

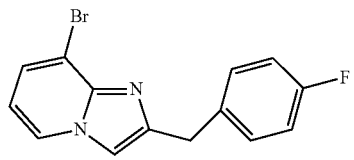 [SMILES: Fc1ccc(Cc2cn3cccc(Br)c3n2)cc1]

A mixture of 3-bromo-2-pyridinamine (3.12 g, 18.03 mmol) and intermediate 3 (5.00 g, 21.64 mmol) in 100 ml EtOH was stirred and heated overnight at 75° C. The solvents were evaporated in vacuo and the residue was partitioned between DCM and a 0.5 N NaOH solution. The separated organic layer was dried (MgSO$_4$), filtered and the solvent was evaporated in vacuo, to yield 7 g of the crude product. A part of the crude product (3.5 g) was purified by reversed-phase (RP) preparative HPLC [RP Shandon Hyperprep® C18 BDS (8 μm, 250 g, I.D. 5 cm); mobile phase: a gradient of (0.25% NH$_4$HCO$_3$ solution in H$_2$O)/MeOH/CH$_3$CN]. The desired fractions were collected and worked-up. Yield: 1.70 g of intermediate 4 (30.9%).

Example A3 a) Preparation of Intermediate 5

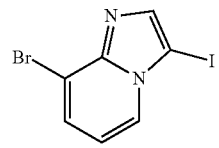 [SMILES: Brc1cccn2c(I)cnc12]

1-Iodo-2,5-pyrrolidinedione (2.28 g, 10.15 mmol) was added to a solution of 8-bromo-imidazo[1,2-a]pyridine (2 g, 10.15 mmol) in CH$_3$CN (8 ml). The r.m. was stirred at r.t. for 30 min. The mixture was concentrated in vacuo and the residue was purified by flash chromatography over silicagel (eluent: DCM/MeOH(NH$_3$) from 100/0 to 99/1). The product fractions were collected and the solvent was evaporated in vacuo. Yield: 2.89 g of intermediate 5 (84.6%).

b) Preparation of Intermediate 6

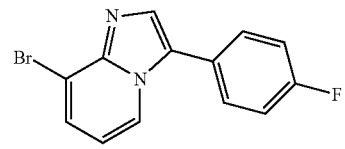 [SMILES: Fc1ccc(-c2cnc3c(Br)cccn23)cc1]

A mixture of intermediate 5 (0.577 g, 1.79 mmol), (4-fluorophenyl)boronic acid (275 mg, 1.97 mmol), DAPCy catalyst (52.28 mg, 0.089 mmol) and K$_3$PO$_4$ (1.14 g, 5.36 mmol) in EtOH (10 ml) was stirred at r.t. for 2 h. The solids were filtered off and the filtrate was evaporated in vacuo. The residue was taken up in DCM, washed with a sat. aq. NaHCO$_3$ solution, dried (MgSO$_4$), filtered and the solvent was evaporated in vacuo to yield a residue that was purified by flash chromatography over silicagel (eluent: DCM/MeOH(NH$_3$) from 100/0 to 98/2). The product fractions were combined and the solvent was evaporated in vacuo. Yield: 0.101 g of intermediate 6 (19.4%).

Example A4 a) Preparation of Intermediate 7

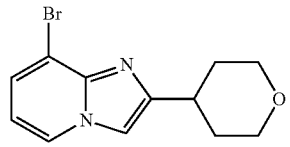 [SMILES: Brc1cccn2cc(C3CCOCC3)nc12]

3-Bromo-2-pyridinamine (0.504 g, 2.9 mmol) and K$_2$CO$_3$ (0.392 g, 2.84 mmol) were added to a solution of 2-bromo-1-(tetrahydro-2H-pyran-4-yl)ethanone (0.784 g, 3.8 mmol) in EtOH (10 ml). The r.m. was stirred at 75° C. for 4 h. and was then cooled to r.t. Subsequently, DCM was added and the solution was washed with a sat. aq. NaHCO$_3$ solution. The organic layer was dried (MgSO$_4$), filtered and the solvent was evaporated in vacuo. The residue was purified by flash chromatography over silicagel (eluent: mixtures of hexane:EtOAc (ratios: 15:1; 10:1; 5:1; 1:1)). The desired fractions were collected and worked up. Yield 0.096 g of intermediate 7 (12.0%).

Example A5 a) Preparation of Intermediate 8

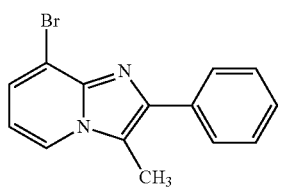 [SMILES: Cc1c(-c2ccccc2)nc2c(Br)cccn12]

A mixture of 3-bromo-2-pyridinamine (1 g, 5.78 mmol) and 2-bromo-1-phenyl-1-propanone (1.48 g, 6.94 mmol) in EtOH (20 ml) was stirred and heated at 100° C. for 2 days. The solvent was evaporated in vacuo and the residue was purified by flash chromatography (eluent: DCM/MeOH(NH$_3$) from 100/0 to 98/2). The product fractions were collected and the solvent was evaporated. The residue was purified by RP preparative HPLC [RP Shandon Hyperprep® C18 BDS (8 μm, 250 g, I.D. 5 cm); mobile phase: a gradient of (0.25% NH$_4$HCO$_3$ solution in H$_2$O)/MeOH]. The product fractions were collected and worked up. Yield: 0.850 g of intermediate 8 (51.2%).

Example A6 a) Preparation of Intermediate 9 and Intermediate 10

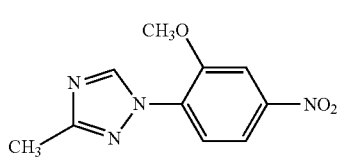
intermediate 9

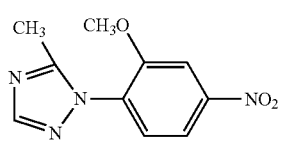
intermediate 10

A mixture of 1-fluoro-2-methoxy-4-nitrobenzene (821.414 mg, 4.8 mmol), 5-methyl-1H-1,2,4-triazole (800 mg, 9.63 mmol), K$_2$CO$_3$ (4.8 mmol) and DMSO (8 ml) was stirred at 120° C. for 1 h. After cooling to r.t., the r.m. was poured into ice H$_2$O. The solid was filtered off, washed with H$_2$O and dried in vacuo at 50° C. Yield: 0.554 g of intermediate 9 (49%). The aq. layer was sat. with NaCl, extracted with DCM and the organic layer was dried (MgSO$_4$), filtered and the solvent was evaporated in vacuo. The residue was purified by column chromatography over silicagel (eluent: DCM). The desired fraction was collected and the solvent was evaporated in vacuo. Yield: 0.147 g of intermediate 10 (13%).

b) Preparation of Intermediate 11

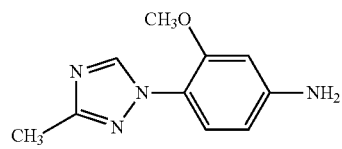

MeOH (50 ml) was added to Pd/C 10% (150 mg) under a N$_2$ atmosphere. Subsequently, a 0.4% thiophene solution in DIPE (1 ml) and intermediate 9 (550 mg, 2.35 mmol) were added. The r.m. was stirred at 25° C. under a H$_2$ atmosphere until 3 eq of H$_2$ was absorbed. The catalyst was filtered off over diatomaceous earth. The filtrate was evaporated and the residue was suspended in DIPE, filtered off and dried in vacuo. Yield: 0.350 g of intermediate 11 (73.0%).

Example A7 a) Preparation of Intermediate 12

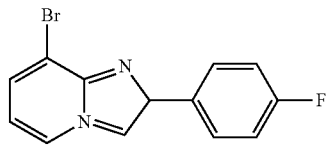

A mixture of 3-bromo-2-pyridinamine (50 g, 289 mmol) and 2-bromo-1-(4-fluorophenyl)ethanone (75.3 g, 346.8 mmol) in EtOH (300 ml) was heated at 75° C. for 17 h. The r.m. was cooled to r.t. The formed precipitate was filtered off, washed with EtOH (50 ml) and dried in vacuo, yielding fraction 1. The corresponding filtrate was concentrated to a volume of 100 ml. EtOH (20 ml) and DIPE (100 ml) were added to the concentrate resulting in precipitation of the product. The solids were filtered off, washed with a mixture of DIPE (50 ml) and EtOH (10 ml), and dried in vacuo, yielding fraction 2. Fractions 1 and 2 were combined and stirred for 30 min in a sat. aq. NaHCO$_3$ solution (500 ml). This mixture was extracted with DCM (500 ml). The separated organic layer was dried (Na$_2$SO$_4$), filtered and the solvent was evaporated in vacuo. The residue was recrystallized from EtOAc. The solid was filtered off and dried in vacuo. Yield: 46.5 g of intermediate 12 (55.3%).

Example A8 a) Preparation of Intermediate 13

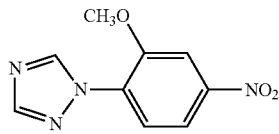

A mixture of 1-fluoro-2-methoxy-4-nitrobenzene (7 g, 40 mmol), 1H-1,2,4-triazole (4.28 g, 60 mmol), K$_2$CO$_3$ (8.31 g, 60 mmol) and DMF (50 ml) was stirred for 1 h at 75° C. The solvent was evaporated and the residue was taken up in EtOAc/H$_2$O. The aq. layer was extracted 3 times with EtOAc. The combined organic layers were dried (MgSO$_4$), filtered and the solvent was evaporated in vacuo. Yield: 4.4 g of intermediate 13. The crude product was used as such in the next reaction step.

b) Preparation of Intermediate 14

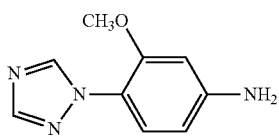

MeOH (50 ml) was added to Pd/C 10% (300 mg) under a N$_2$ atmosphere. A 0.4% thiophene solution in DIPE (2 ml) and intermediate 13 (3.13 g, 11.4 mmol) was added. The r.m. was stirred at 25° C. under a H$_2$ atmosphere until 3 eq of H$_2$ was absorbed. The catalyst was filtered off over diatomaceous earth and the filtrate was evaporated. The residue was purified by flash chromatography over silicagel (eluent: DCM/MeOH (NH$_3$) from 100/0 to 98/2). The desired fraction was collected and the solvent was evaporated in vacuo. Yield: 1.4 g of intermediate 14 (64.8%).

Example A9 a) Preparation of Intermediate 15

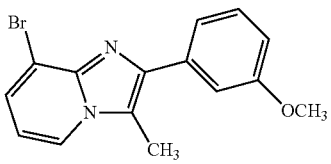 [SMILES: COc1cccc(-c2nc3c(Br)cccn3c2C)c1]

3-Bromo-2-pyridinamine (24.9 g, 144 mmol), 2-bromo-1-(3-methoxyphenyl)-1-propanone (42 g, 172.8 mmol) and 250 ml n-butanol were heated at reflux temperature for 3 nights. The mixture was separated between DCM and H$_2$O. The organic layer was dried (MgSO$_4$), filtered and the solvent was evaporated in vacuo. The residue was purified by column chromatography over silicagel (eluent: DCM/MeOH(NH$_3$) from 100/0 to 98/2). The purest fractions were concentrated under reduced pressure and the residue was crystallized from DIPE. Yield: 19 g of intermediate 15 (41.6%).

Example A10 a) Preparation of Intermediate 16

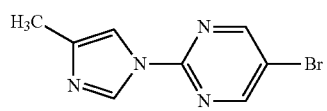

A mixture of 4-bromo-2-chloropyrimidine (5 g, 25.8 mmol), 4-methyl-1H-imidazole (4.25 g, 51.7 mmol) and K$_2$CO$_3$ (10.72 g, 77.5 mmol) in NMP (100 ml) was heated at 85° C. overnight. The mixture was separated between DCM and H$_2$O. The organic layer was dried (MgSO$_4$), filtered and the solvent was evaporated. H$_2$O was added to the residue and the resulting precipitate was collected by filtration and dried in vacuo. Yield: 4.7 g of intermediate 16 (76%).

b) Preparation of Intermediate 17

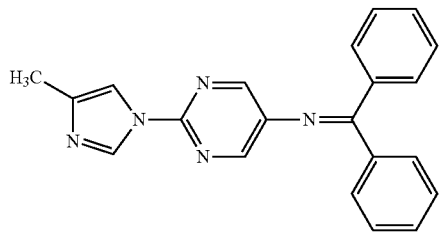 [SMILES: Cc1cn(-c2ncc(N=C(c3ccccc3)c3ccccc3)cn2)cn1]

A mixture of 2-methyl-2-propanol, sodium salt (1.688 g, 17.6 mmol), BINAP (195 mg, 0.314 mmol), Pd$_2$(dba)$_3$ (287 mg, 0.314 mmol), intermediate 16 (3 g, 12.5 mmol) and benzophenone imine (2.27 g, 12.5 mmol) in toluene (40 ml; previously deoxygenated) was stirred and heated at 120° C. for 4 h. The mixture was separated between DCM and H$_2$O. The organic phase was separated, dried (MgSO$_4$), filtered and the solvent was evaporated in vacuo. Yield: 3.4 g of crude intermediate 17.

c) Preparation of Intermediate 18

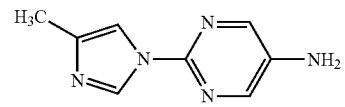

A 1 N aq. HCl solution (11 ml, 11 mmol) was added to a solution of intermediate 17 (3.4 g, 4.1 mmol) in THF (10 ml). The r.m. was stirred at r.t. for 2 h. The solvent was evaporated in vacuo and the residue was separated between DCM and H$_2$O, basified with an aq. NH$_4$OH solution to pH 10. The organic phase was separated, dried (MgSO$_4$), filtered and the solvent was evaporated in vacuo. The product was purified by flash column chromatography over silicagel (eluent: DCM/MeOH from 98/2 to 95/5). The product fractions were collected and the solvent was evaporated in vacuo. Yield: 0.36 g of intermediate 18 (16% over 2 steps).

Example A11 a) Preparation of Intermediate 19

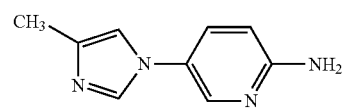

CuI (8.25 g, 43 mmol) was added under a N₂ flow to a solution of 5-bromo-pyridin-2-ylamine (5 g, 28.9 mmol), 4-methyl-1H-imidazole (5.9 g, 72 mmol), and Cs₂CO₃ (9.4 g, 28.9 mmol) in DMSO (100 ml). The r.m. was heated at 130° C. for 2 days, then cooled, and CH₃CN was added. A blue precipitate was filtered off. The filtrate was concentrated, and the residue was separated between DCM and H₂O. The organic phase was dried (MgSO₄), filtered and the solvent was evaporated. The residue was purified by flash column chromatography over silicagel (eluent: DCM/MeOH 98/2 to 95/5). The product fractions were collected and the solvent was evaporated. Yield: 0.628 g of intermediate 19. The aq. layer was concentrated to precipitate more product, which was filtered off and dried in vacuo. Yield: 0.16 g of intermediate 19 (total yield 15%).

Example A12 a) Preparation of Intermediate 20

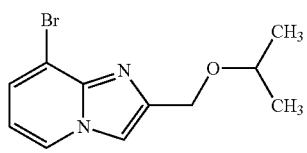

8-Bromo-2-chloromethyl-imidazo[1,2-a]pyridine hydrochloric acid salt (0.3 g, 1.06 mmol), and 2-propanol (0.122 ml g, 1.59 mmol) were dissolved in DMF (3 ml) and sodium hydride (60% dispersion in mineral oil, 0.106 g, 2.3 mmol) was added. The r.m. was stirred at r.t. overnight. The mixture was separated between EtOAc and H₂O. The organic layer was dried (MgSO₄), filtered and the solvent was evaporated. The residue was purified by flash column chromatography over silicagel (eluent: hexane/EtOAc from 91/9 to 83/17). The purest fractions were concentrated under reduced pressure. Yield: 0.11 g of intermediate 20 (44%).

Example A13 a) Preparation of Intermediate 21

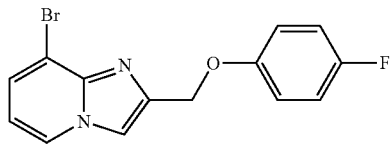 [SMILES: Fc1ccc(OCc2cn3cccc(Br)c3n2)cc1]

8-Bromo-2-chloromethyl-imidazo[1,2-a]pyridine hydrochloric acid salt (0.14 g, 0.5 mmol), 4-fluoro-phenol (0.072 g, 0.64 mmol), and Cs₂CO₃ (0.419 g, 1.29 mmol) in DMF (1.3 ml) were stirred at 45° C. overnight. The mixture was separated between EtOAc and H₂O. The organic layer was dried (MgSO₄), filtered and the solvent was evaporated in vacuo. The residue was purified by flash column chromatography over silicagel (eluent: hexane/EtOAc from 100/1 to 83/17). The purest fractions were concentrated under reduced pressure. Yield: 0.111 g of intermediate 21 (69%).

Example A14 a) Preparation of Intermediate 22

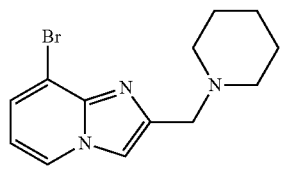 [SMILES: Brc1cccn2cc(CN3CCCCC3)nc12]

8-Bromo-2-chloromethyl-imidazo[1,2-a]pyridine hydrochloric acid salt (0.4 g, 1.42 mmol), piperidine (0.14 ml, 1.56 mmol), and diisopropylethylamine (0.367 ml, 2.13 mmol) in DMA (5 ml) were stirred at 50° C. overnight. The mixture was separated between EtOAc and a sat. aq. NaHCO₃ solution. The organic layer was dried (MgSO₄), filtered and the solvent was evaporated in vacuo. The residue was purified by flash column chromatography over silicagel (eluent: DCM/MeOH from 95/5 to 91/9). The purest fractions were concentrated under reduced pressure. Yield: 0.136 g of intermediate 22 (33%).

Example A15 a) Preparation of Intermediate 23

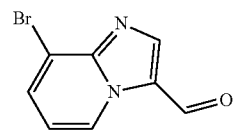

Phosphoroxychloride (0.59 ml, 6.34 mmol) was added to DMF (7 ml) at 0° C. and the mixture was stirred for 0.5 h at this temperature. 8-Bromo-imidazo[1,2-a]pyridine (0.5 g, 2.53 mmol) was added at 0° C., and the r.m. was stirred at r.t. overnight. The r.m. was poured into an ice-cooled aq. Na₂CO₃ solution and extracted with DCM. The organic layer was dried (MgSO₄), filtered and the solvent was evaporated in vacuo. The residue was triturated with DIPE. The solid was collected and air dried. Yield: 0.45 g of intermediate 23 (78%).

b) Preparation of Intermediate 24

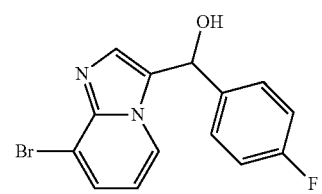 [SMILES: OC(c1ccc(F)cc1)c1cnc2c(Br)cccn12]

A solution of 1-Bromo-4-fluoro benzene (0.5 g, 2.86 mmol) in THF (6.4 ml) was added to a suspension of magnesium (63 mg, 2.6 mmol) and ethyl magnesiumchloride (2 drops of a 1 M solution in THF) in THF (6 ml) at r.t. under a N₂ atmosphere. The mixture was heated at reflux for 10 min., then cooled to r.t. The resulting mixture was added to a solution of intermediate 23 (0.234 g, 1.04 mmol) in THF (0.9 ml), and the r.m. was stirred at r.t. overnight. The r.m. was poured in a sat. aq. NH₄Cl solution and extracted with DCM. The organic layer was dried (MgSO₄), filtered and the solvent was evaporated in vacuo. The residue was purified by flash column chromatography over silicagel (eluent: EtOAc/MeOH from 83/17 to 50/50). The purest fractions were concentrated under reduced pressure. Yield: 0.07 g of intermediate 24 (21%).

c) Preparation of Intermediate 25

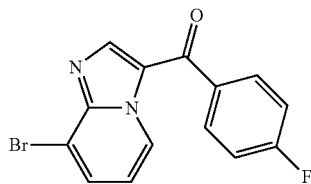 [SMILES: O=C(c1ccc(F)cc1)c1cnc2c(Br)cccn12]

A solution of Na₂Cr₂O₇ in aq. H₂SO₄ (Jones reagent) (0.092 ml, 0.44 mmol) was added to a solution of intermediate 24 (0.07 g, 0.22 mmol) in acetone (3 ml), and the r.m. was stirred at r.t. for 15 min. Et₂O (1.5 ml) and 2-propanol (0.046 ml) were added, and the green solid was filtered off. The filtrate was separated between EtOAc and a sat. aq. NaHCO₃ solution. The organic layer was dried (MgSO₄), filtered and the solvent was evaporated. Yield: 0.07 g of intermediate 25 which was used as such in the next step.

Example A16 a) Preparation of Intermediate 26

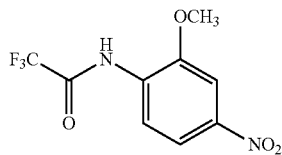 [SMILES: COc1cc([N+](=O)[O-])ccc1NC(=O)C(F)(F)F]

Trifluoroacetic acid anhydride (41.4 ml, 0.297 mol) was added dropwise to a solution of 2-methoxy-4-nitro-aniline (50 g, 0.297 mol) in pyridine (125 ml). The r.m. was stirred at r.t. for 1 h. and then separated between DCM and ice-water. The organic layer was dried (MgSO₄), filtered and the solvent was evaporated in vacuo. The residue was triturated with heptane. The solid was collected and air dried. Yield: 75 g of intermediate 26 (95%).

b) Preparation of Intermediate 27

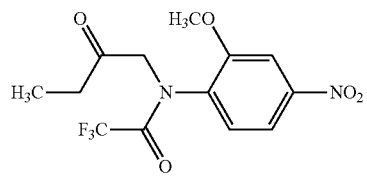

1-Bromo-butan-2-one (5 g, 31.8 mmol) was added dropwise to a suspension of intermediate 26 (4.2 g, 15.9 mmol), potassium iodide (0.264 g, 1.59 mmol) and Cs₂CO₃ (10.4 g, 31.8 mmol) in DMF (320 ml). The formed yellow precipitate was filtered off, washed with H₂O, and dried in vacuo. Yield: 4.2 g of intermediate 27 (79%).

c) Preparation of Intermediate 28

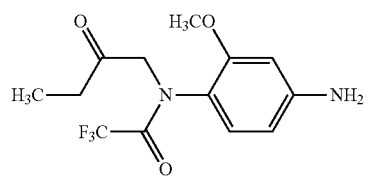 [SMILES: CCC(=O)CN(C(=O)C(F)(F)F)c1ccc([N+](=O)[O-])cc1OC]

MeOH (150 ml) was added to Pd/C 10% (1 g) under a N₂ atmosphere. Subsequently, a 0.4% thiophene solution in DIPE (2 ml) and intermediate 27 (4 g, 12 mmol) were added. The r.m. was stirred at 25° C. under a H₂ atmosphere until 3 eq of H₂ was absorbed. The catalyst was filtered off over diatomaceous earth and the filtrate was evaporated. The residue was separated between DCM and H₂O. The organic layer was dried (MgSO₄), filtered and the solvent was evaporated in vacuo. Yield: 2.7 g of intermediate 28 (74%).

d) Preparation of Intermediate 29

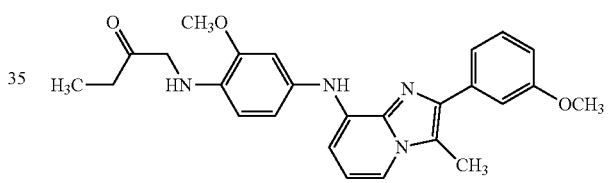

2-Methyl-2-propanol, sodium salt (0.99 g, 10.3 mmol), BINAP (0.12 g, 0.193 mmol), palladium(II) diacetate (29 mg, 0.13 mmol) and intermediate 28 (1.18 g, 3.87 mmol) were added to a solution of intermediate 15 (818 mg, 2.58 mmol) in toluene (15 ml) and the mixture was purged with N₂ for 5 min. The r.m. was stirred and heated at 100° C. overnight under a N₂ atmosphere. H₂O was added and the mixture was extracted with DCM. The organic layer was dried (MgSO₄), filtered and concentrated in vacuo. The residue was purified by RP preparative HPLC [RP Shandon Hyperprep® C18 BDS (8 µm, 250 g, I.D. 5 cm); mobile phase: a gradient of (0.25% NH₄HCO₃ solution in H₂O)/MeOH/CH₃CN]. The product fractions were collected and worked up. Yield: 236 mg of intermediate 29 (21%).

e) Preparation of Intermediate 30

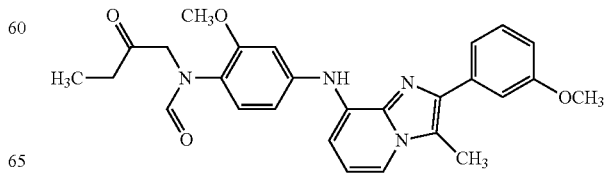

A mixture of formic acid (0.2 ml, 2.07 mmol) and Ac₂O (3 ml) was stirred at 0° C. for 0.5 h. Subsequently, a solution of intermediate 29 (230 mg, 0.52 mmol) in DCM (6 ml) was added dropwise and the resulting r.m. was stirred at r.t. for 1 h. The r.m. was neutralized to pH 7 with an aq. 1 N NaOH solution, and then extracted with DCM. The organic layer was dried (MgSO₄), filtered and concentrated in vacuo. Yield: 250 mg of intermediate 30 which was used as such in the next step.

Example A17 a) Preparation of Intermediate 31

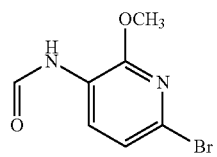 [SMILES: COc1nc(Br)ccc1NC=O]

A mixture of formic acid (12.8 ml, 340 mmol) and Ac₂O (8.54 ml, (91 mmol) was stirred at r.t. for 40 min. A solution of 3-amino-6-bromo-2-methoxy-pyridine (5 g, 24.6 mmol) in THF (30 ml) was added dropwise and the resulting r.m. was stirred overnight at 60° C. The r.m. was cooled and poured into ice-water. The precipitate was filtered off, washed (H₂O) and dried. Yield: 5.2 g of intermediate 31 (76%).

b) Preparation of Intermediate 32

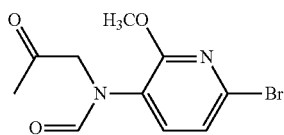 [SMILES: COc1nc(Br)ccc1N(C=O)CC(C)=O]

1-Chloro-propan-2-one (4.34 g, 46.9 mmol) was added dropwise to a mixture of intermediate 42 (5.2 g, 18.8 mmol), KI (0.343 g, 2.06 mmol) and Cs₂CO₃ (21.4 g, 65.9 mmol) in DMF (50 ml). The r.m. was stirred at r.t. overnight and was then poured into ice-water. The mixture was extracted with EtOAc. The combined organic layers were dried (MgSO₄), filtered and concentrated in vacuo. The residue was suspended in DIPE. The precipitate was filtered off, washed with DIPE and dried. Yield: 4.43 g of intermediate 32 (82%).

c) Preparation of Intermediate 33

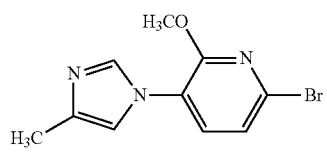

Intermediate 43 (4.4 g, 15.3 mmol) was added to a mixture of CH₃COONH₄ (5.41 g, 70.2 mmol) in AcOH (10 ml). The r.m. was heated at reflux for 1 h. The r.m. was cooled to r.t. and poured into a mixture of ice-water and EtOAc. The mixture was basified with a 50% w/v aq. NaOH solution to pH 9. The organic layer was separated, dried (MgSO₄), filtered and concentrated in vacuo. The solid was used as such in the next reaction step. Yield: 3.78 g of crude intermediate 33.

d) Preparation of Intermediate 34

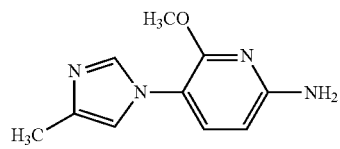

2-Methyl-2-propanol sodium salt (0.717 g, 7.46 mmol), BINAP (464 mg, 0.746 mmol), Pd₂(dba)₃ (342 mg, 0.373 mmol), intermediate 44 (1.0 g, 3.73 mmol) and benzophenone imine (0.845 g, 4.66 mmol) in toluene (20 ml; previously deoxygenated) were stirred and heated at 100° C. for 2 h under microwave conditions. The mixture was cooled, and the solvent was removed in vacuo. THF (50 ml) and a 1 N aq. HCl solution (50 ml) were added to the residue and the mixture was stirred at r.t. for 1 h. The r.m. was basified with a 10% aq. Na₂CO₃ solution and extracted with EtOAc. The organic layers were dried (MgSO₄), filtered and the solvent was evaporated in vacuo. The product was purified by flash column chromatography over silica gel (eluent: DCM/MeOH from 100/0 to 95/5). The product fractions were collected and the solvent was evaporated. Yield: 0.6 g of intermediate 34 (52% yield over 2 reaction steps).

Example A18 a) Preparation of Intermediate 35

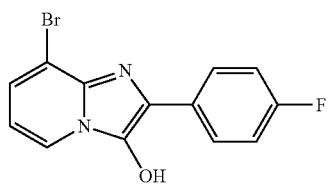 [SMILES: Oc1c(-c2ccc(F)cc2)nc2c(Br)cccn12]

BF₃ etherate (0.154 ml, 1.32 mmol) was added to a mixture of 4-fluorophenylglyoxal hydrate (4.5 g, 26.5 mmol) and 2-amino-3-bromopyridine (4.72 g, 26.5 mmol) in DCM (100 ml). The r.m. was stirred at r.t. for 6 h. The resulting precipitate was filtered off and dried in vacuo. Yield: 4 g of intermediate 35 (49%).

b) Preparation of Intermediate 36

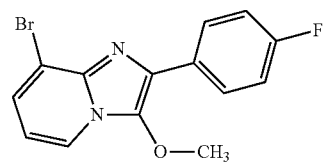 [SMILES: COc1c(-c2ccc(F)cc2)nc2c(Br)cccn12]

NaH (60% in mineral oil, 414 mg, 10.3 mmol) was added to an ice-cooled solution of intermediate 35 (1.06 g, 3.45 mmol) in DMF (50 ml). The r.m. was stirred at 0° C. for 15 min, then CH₃I (0.258 ml, 4.14 mmol) was added and the resulting r.m. was stirred at r.t. overnight. The r.m. was quenched with H₂O, and then concentrated in vacuo. The residue was partitioned between DCM and H₂O, the organic layer was dried (MgSO₄), filtered and concentrated in vacuo. The residue was purified by flash column chromatography over silicagel (eluent: n-heptane/EtOAc from 100/0 to 50/50). The product fractions were collected and the solvent was evaporated in vacuo. The residue was suspended in DIPE and dried in vacuo. Yield: 445 mg of intermediate 36 (40%).

Example A19 a) Preparation of Intermediate 37

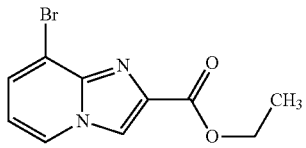

2-Amino-3-bromopyridine (12.0 g, 69 mmol) and 3-bromo-pyruvic acid ethyl ester (20.0 g, 0.104 mol) were dissolved in EtOH and heated to reflux for 60 h. The solution was cooled to r.t. and the solvent was evaporated. The residue was dissolved in EtOAc and washed with sat. aq. NaHCO₃, H₂O and brine. The organic layer was dried (MgSO₄), filtered and evaporated under reduced pressure. The residue was purified by RP preparative HPLC [RP Shandon Hyperprep® C18 BDS (8 μm, 250 g, I.D. 5 cm); mobile phase: a gradient of (0.25% NH₄HCO₃ solution in H₂O)/MeOH]. The product fractions were collected and worked up. Yield: 10 g of intermediate 37 (50%).

b) Preparation of Intermediate 38

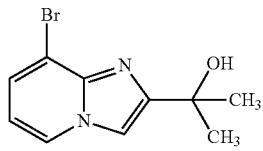

Intermediate 37 (350 mg, 1.3 mmol) was added to a refluxing solution of CH₃MgBr (3 M in THF, 0.91 ml, 2.73 mmol) in THF (10.5 ml), and refluxing was continued for 15 min. The solution was cooled to r.t. Then H₂O was added and the solution was stirred for 5 min. The solution was acidified with aq. 1 N HCl until pH 2. The THF was evaporated under reduced pressure. A sat. K₂CO₃ solution was added until neutral pH. The mixture was extracted twice with ether. The combined organic layers were dried (MgSO₄), filtered and evaporated under reduced pressure. The residue was purified via flash column chromatography over silicagel (eluent: DCM/MeOH from 100/0 to 97.5/2.5). The product fractions were collected and the solvent was evaporated in vacuo. Yield: 240 mg of intermediate 38 (72%).

c) Preparation of Intermediate 39

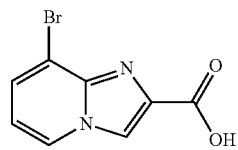 [SMILES: O=C(O)c1cn2cccc(Br)c2n1]

Intermediate 37 (2.02 g, 7.4 mmol) was dissolved in a mixture of dioxane/H₂O (16 ml/4 ml) and the mixture was cooled on an ice-bath. LiOH (355 mg, 14.8 mmol) was added and the resulting mixture was stirred for 20 h at r.t. The volatiles were evaporated under reduced pressure. The mixture was cooled using an ice-bath, and was acidified with an aq. 1N HCl solution until pH 4. The precipitate was filtered off, washed with cold water (10 ml), and dried in vacuo. Yield 1.5 g of intermediate 39 (88%).

d) Preparation of Intermediate 40

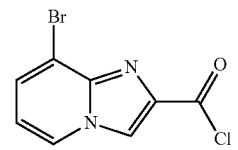 [SMILES: O=C(Cl)c1cn2cccc(Br)c2n1]

SOCl₂ (15 ml, 206 mmol) was added slowly to intermediate 39 (1.6 g, 6.6 mmol) while cooling on ice. The resulting solution was heated to reflux temperature for 4 h, and was then cooled to r.t. and concentrated in vacuo. The residue was triturated with DIPE and finally the product was dried. Yield: 1.7 g of intermediate 40 (99%).

e) Preparation of Intermediate 41

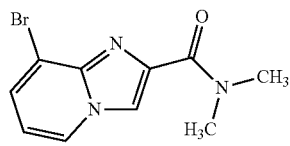

A 2 M solution of dimethylamine in THF (0.58 ml, 1.16 mmol) was added to an ice-cooled suspension of intermediate 40 (300 mg, 1.16 mmol) in THF (5 ml). The reaction vial was sealed off and stirred for 3 h at r.t. Another equivalent of dimethylamine (0.58 ml, 1.16 mmol) was added and the resulting mixture was stirred overnight. The solvent was evaporated. Yield: 151 mg of intermediate 41 (49%).

f) Preparation of Intermediate 42

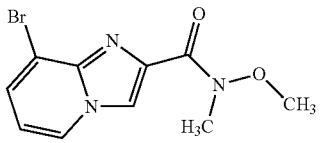 [SMILES: CON(C)C(=O)c1cn2cccc(Br)c2n1]

A suspension of intermediate 39 (322 mg, 1.34 mmol) and carbonyldiimidazole (238 mg, 1.47 mmol) in THF (11 ml) was stirred at r.t. for 2 h. DIPEA (0.233 ml, 1.34 mmol) was added and the resulting mixture was stirred for 30 min. at r.t. Then DMF (2 ml) was added to the suspension and the mixture was stirred for 60 h at r.t. The r.m. was cooled to 0° C. and O,N-dimethyl-hydroxylamine (143 mg, 1.47 mmol) was added. The mixture was stirred for 20 h at r.t. The solvents were evaporated under reduced pressure. The residue was dissolved in DCM and washed 3 times with $H_2O$. The organic layer was dried ($MgSO_4$), filtered and evaporated under reduced pressure. The residue was purified via flash column chromatography over silicagel (eluent: DCM/MeOH($NH_3$) from 100/0 to 99/1). The product fractions were collected and the solvent was evaporated in vacuo. Yield: 216 mg of intermediate 42 (57%).

g) Preparation of Intermediate 43

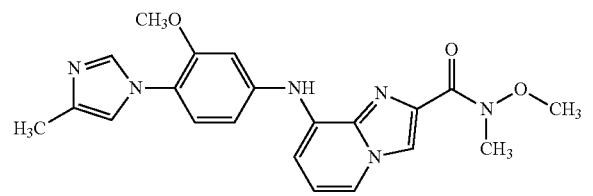

Intermediate 2a (80 mg, 0.396 mmol), $Pd_2(dba)_3$ (40 mg, 0.044 mmol), X-phos (42 mg, 0.088 mmol) and $Cs_2CO_3$ (430 mg, 1.32 mmol) were added to a solution of intermediate 42 (125 mg, 0.44 mmol) in 2-methyl-2-propanol (10 ml) under a $N_2$ atmosphere. The r.m. was heated at 90° C. for 22 h. Then, $H_2O$ was added and the mixture was extracted with DCM. The organic layer was dried ($MgSO_4$), filtered and evaporated. The residue was purified by flash chromatography over silicagel (eluent: DCM/MeOH($NH_3$) from 100/0 to 97/3). The product fractions were collected and the solvent was evaporated in vacuo. Yield: 71 mg of intermediate 43 (40%).

Example A20 a) Preparation of Intermediate 44

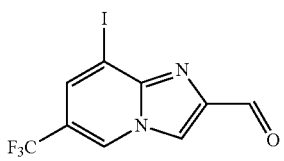 [SMILES: O=Cc1cn2cc(C(F)(F)F)cc(I)c2n1]

DIBAH (1 M in hexane, 2.6 ml, 2.6 mmol) was added to a cooled (−78° C.) solution of ethyl 8-iodo-6-(trifluoromethyl) imidazo[1,2-a]pyridine-2-carboxylate (1.0 g, 2.6 mmol) in THF (30 ml). The r.m. was stirred at −78° C. for 1 h, then another eq of DIBAH (1 M in hexane) was added and stirring was continued at −78° C. for 1 h. The r.m. was quenched with $H_2O$ (5 ml). The mixture was partitioned between DCM and $H_2O$. The organic layer was separated, dried ($MgSO_4$), and filtered. $MnO_2$ (4.53 g, 52 mmol) was added and the r.m. was stirred at r.t. overnight. The mixture was filtered over a pad of diatomaceous earth, and the filtrate was concentrated in vacuo. Yield: 0.51 g of intermediate 44 (used as such in the next reaction step).

b) Preparation of Intermediate 45

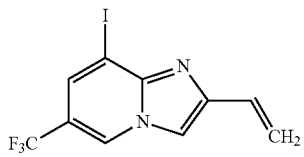 [SMILES: C=Cc1cn2cc(C(F)(F)F)cc(I)c2n1]

A solution of KOtBu (0.505 g, 4.5 mmol) and methyltriphenylphosphonium bromide (1.6 g, 4.5 mmol) in $Et_2O$ (15 ml) was stirred at 0° C. for 1 h. A solution of intermediate 44 (0.51 g, 1.5 mmol) in $Et_2O$ (10 ml) was added at 0° C., and the r.m. was stirred for 18 h at r.t. The r.m. was filtered over diatomaceous earth and the filtrate was concentrated in vacuo. The residue was reacted again under the same reaction conditions and worked-up. The now obtained residue was purified by column chromatography over silicagel (eluent: DCM). The product fractions were collected and the solvent was evaporated in vacuo. Yield: 55 mg of intermediate 45 (11%).

Example A21 a) Preparation of Intermediate 46

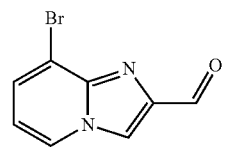 [SMILES: O=Cc1cn2cccc(Br)c2n1]

1,1,3-Trichloroacetone (11.3 mL, 88.7 mmol) in DME (10 ml) was added dropwise to a solution of 2-amino-3-bromopyridine (10.0 g, 57.8 mmol) in DME (90 ml) and heated at 40° C. overnight. The r.m. was then heated at 80° C. for 4 h, cooled to r.t., and DIPEA (10 ml, 57.8 mmol) was added. Subsequently, the r.m. was heated at 80° C. for 60 h. The mixture was cooled to r.t. and DCM and $H_2O$ were added. The mixture was made alkaline by the addition of $K_2CO_3$, then filtered, and the layers were separated. The aq. layer was extracted with DCM, and the combined organic layer was washed with $H_2O$ and brine, dried ($MgSO_4$), filtered and evaporated under reduced pressure. The residue was purified via column chromatography over silicagel (eluent: DCM). The product fractions (a mixture of intermediate 46 and the dichloro precursor) were collected and the solvent was evaporated in vacuo. A suspension of $CaCO_3$ (13.1 g, 131 mmol) in $H_2O$ (200 ml) was added to the residue, and the r.m. was heated at 90° C. for 1 h, and then overnight at r.t. The mixture was extracted with DCM. The organic layer was washed with brine, dried (MgSO$_4$), filtered and evaporated under reduced pressure. The residue was purified via column chromatography over silicagel (eluent: DCM/MeOH from 100/0 to 97.5/2.5). The product fractions were collected and the solvent was evaporated in vacuo. Yield: 7.25 g of intermediate 46 (56%).

b) Preparation of Intermediate 64

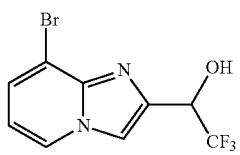

Trimethyl-trifluoromethyl-silane (8.25 ml, 55.8 mmol) was added to a degassed and ice-cooled sol. of intermediate 46 (6.1 g, 27.1 mmol) in DME (92 ml). CsF (823 mg, 5.4 mmol) was added to this mixture, and the r.m. was stirred ar r.t. for 30 min. Another eq of trimethyl-trifluoromethyl-silane was added, and the r.m. was stirred at r.t. for 1 h. The r.m. was cooled on an ice-bath, and a 1 N aq. HCl sol. (40 ml) was added and the mixture was stirred at r.t. for 5 h. Additional a 1 N aq. HCl sol. (10 ml) was added and the mixture was stirred at 45° C. overnight. The mixture was partly concentrated in vacuo to remove the organic solvents. H$_2$O was added, and the mixture was cooled and basified with a sat. aq. NaHCO$_3$ solution to pH 8. The resulting solids were filtered off, washed with H$_2$O and dried in vacuo. Yield: 5.9 g of intermediate 64 (74%).

c) Preparation of Intermediate 65

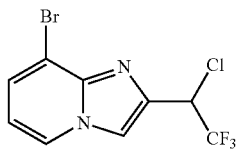 [SMILES: FC(F)(F)C(Cl)c1cn2cccc(Br)c2n1]

SOCl$_2$ (0.44 ml, 6 mmol) and pyridine (0.244 ml, 3 mmol) were added to a solution of intermediate 64 (490 mg, 1.51 mmol) in DCM (10 ml) while cooling on ice. The resulting solution was heated at 45° C. overnight, and was then cooled to r.t. and concentrated in vacuo. The residue was partitioned between DCM and an aq. K$_2$CO$_3$ solution. The organic layer was dried (MgSO$_4$), filtered and concentrated in vacuo. Yield: 0.55 g of crude intermediate 65 which was used as such in the next reaction step.

Example A22 a) Preparation of Intermediate 47

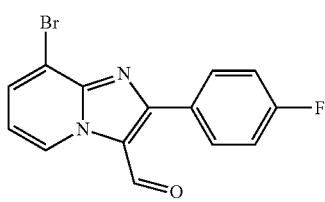 [SMILES: O=Cc1c(-c2ccc(F)cc2)nc2c(Br)cccn12]

Phosphoroxychloride (1.25 ml, 13.7 mmol) was added to DMF (3.5 ml) at 0° C. and the mixture was stirred for 30 min at 0° C. Intermediate 12 (1 g, 3.44 mmol) was added at 0° C., and the r.m. was stirred at r.t. and DMF (5 ml) was added. The r.m. was stirred at r.t. overnight. The r.m. was poured on ice and the mixture was neutralized by adding NaHCO$_3$. The mixture was extracted with DCM. The organic layer was dried (MgSO$_4$), filtered and the solvent was evaporated in vacuo. The residue was triturated with DIPE. The solid was collected and dried. Yield: 0.625 g of intermediate 47 (57%).

b) Preparation of Intermediate 48

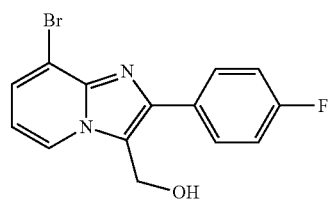

NaBH$_4$ (28 mg, 0.75 mmol) was added to a solution of intermediate 47 (200 mg, 0.63 mmol) in MeOH (5 ml) and THF (2 ml). The r.m. was stirred at r.t for 15 min and then the solvents were removed. The residue was partitioned between DCM and H$_2$O. The organic layer was dried (MgSO$_4$), filtered and the solvent was evaporated in vacuo. Yield: 90 mg of intermediate 48 (45%).

c) Preparation of Intermediate 49

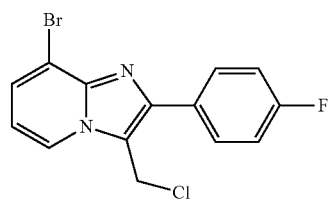 [SMILES: Fc1ccc(-c2nc3c(Br)cccn3c2CCl)cc1]

SOCl$_2$ (33 mg, 0.28 mmol) was added to intermediate 48 (90 mg, 0.28 mmol) in DCM (2 ml). The r.m. was stirred at r.t for 30 min, then an aq.sat. NaHCO$_3$ sol. was added, and the organic layer was separated. The organic layer was filtered over diatomaceous earth and the filtrate was concentrated. Yield: 90 mg of intermediate 49 (95%).

d) Preparation of Intermediate 50

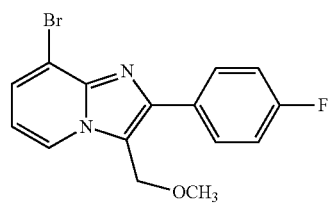 [SMILES: COCc1c(-c2ccc(F)cc2)nc2c(Br)cccn12]

A 0.5 M NaOMe solution in MeOH (0.64 ml, 0.32 mmol) was added to a solution of intermediate 49 (90 mg, 0.265 mmol) in MeOH (2 ml). The r.m. was stirred at r.t for 30 min and then the solvents were removed in vacuo. The residue was partitioned between DCM and H₂O. The organic layer was filtered over diatomaceous earth and the filtrate was concentrated. The residue was triturated with DIPE and dried in vacuo. Yield: 60 mg of intermediate 50 (67%).

e) Preparation of Intermediate 51

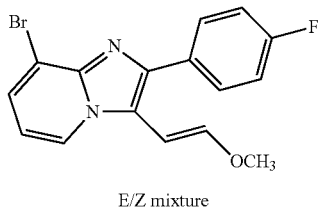 [SMILES: CO/C=C/c1c(-c2ccc(F)cc2)nc2c(Br)cccn12]

E/Z mixture

A solution of KOtBu (0.87 g, 7.74 mmol) in THF (7 ml) was added to a suspension of methoxymethylenetriphenylphosphonium chloride (1.53 g, 4.47 mmol) in THF (3 ml) at −15° C. The r.m. was stirred for 30 min. Subsequently, a solution of intermediate 47 (0.95 g, 3 mmol) in THF (3 ml) was added at 5° C. and the r.m. was stirred for 1 h at r.t. The r.m. was partitioned between DCM and H₂O. The organic layer was dried (MgSO₄), filtered and the solvent was evaporated in vacuo. The residue was purified by column chromatography over silicagel (eluent: DCM/MeOH 99/1). The product fractions were collected and the solvent was evaporated in vacuo. Yield: 700 mg of intermediate 51 (68%; E/Z mixture).

Example A23 a) Preparation of Intermediate 52

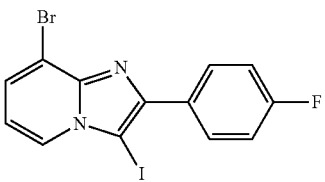 [SMILES: Fc1ccc(-c2nc3c(Br)cccn3c2I)cc1]

1-Iodo-2,5-pyrrolidinedione (2.32 g, 10.3 mmol) was added to intermediate 12 (2 g, 6.87 mmol) in DCM (25 ml). The r.m. was stirred at r.t. for 1 h and was then washed with H₂O. The organic layer was dried (MgSO₄), filtered and concentrated. The residue was triturated with DIPE, and dried in vacuo. Yield: 1.2 g of intermediate 52 (42%).

b) Preparation of Intermediate 53

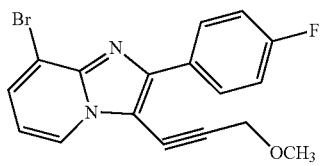

A mixture of intermediate 52 (600 mg, 1.44 mmol), 3-methoxy-propyne (111 mg, 1.58 mmol), PdCl₂(PPh₃)₂ (40 mg, 0.057 mmol), CuI (10 mg, 0.053 mmol) in Et₃N (6 ml) was stirred at 50° C. for 20 h under a N₂ atmosphere. The mixture was partitioned between DCM and H₂O. The organic layer was dried (MgSO₄), filtered, and concentrated in vacuo. The residue was purified by column chromatography over silicagel (eluent: DCM/MeOH 99/1). The product fractions were collected and the solvent was evaporated in vacuo. Yield: 170 mg of intermediate 53 (33%).

Example A24

Preparation of Intermediate 54

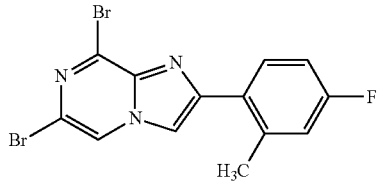 [SMILES: Cc1cc(F)ccc1-c1cn2cc(Br)nc(Br)c2n1]

A mixture of 3,5-dibromo-pyrazin-2-ylamine (5 g, 19.8 mmol) and 2-bromo-1-(4-fluoro-2-methyl-phenyl)-ethanone (13.7 g, 59.3 mmol) was heated at 100° C. for 76 h. The solvent was removed under reduced pressure, and the residue was purified via flash column chromatography over silicagel (eluent: n-heptane/EtOAc 90/10). The product fractions were collected and the solvent was evaporated in vacuo. The residue was suspended in DIPE and dried in vacuo. Yield: 3.1 g of intermediate 54 (41%).

Example A25

Preparation of Intermediate 55

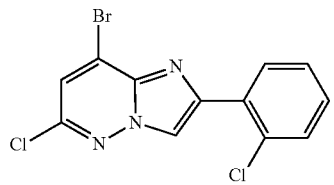 [SMILES: Clc1cc(Br)c2nc(-c3ccccc3Cl)cn2n1]

A mixture of 4-bromo-6-chloro-pyridazin-3-ylamine (5 g, 24 mmol) and 2-bromo-1-(2-chloro-phenyl)-ethanone (10 g, 43 mmol) in 2-propanol (20 ml) was heated at 100° C. overnight. The solvent was removed under reduced pressure, and the residue was triturated with DIPE. The solid was dissolved in DCM and washed with an aq. sat. NaHCO₃ sol. The organic layer was dried (MgSO₄), filtered and the solvent was evaporated in vacuo. The residue was purified via flash column chromatography over silicagel (eluent: DCM/MeOH 95/5). The product fractions were collected and the solvent was evaporated in vacuo. Yield: 3.1 g of intermediate 55 (38%).

Example A26 a) Preparation of Intermediate 56

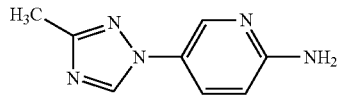

CuI (1.71 g, 8.9 mmol) and N,N'-dimethylethylenediamine (1.91 ml, 17.92 mmol) were added to a mixture of 2-amino-5-iodopyridine (5.03 g, 22.4 mmol), 3-methyl-1H-1,2,4-triazole (2.42 g, 29.1 mmol) and $Cs_2CO_3$ (14.60 g, 44.81 mmol) in DMF (40 ml). The r.m. was heated at 110° C. for 7 h., the r.m. was cooled, EtOAc was added and the mixture was washed with $H_2O$. The $H_2O$ layer was extracted 5 times with EtOAc. The combined organic layers were dried ($MgSO_4$), filtered and the solvent was evaporated in vacuo. The residue was purified by RP preparative HPLC [RP Shandon Hyperprep® C18 BDS (8 μm, 250 g, I.D. 5 cm); mobile phase: a gradient of (0.25% $NH_4HCO_3$ solution in $H_2O$)/MeOH/$CH_3CN$]. The product fractions were collected and the solvent was evaporated. Yield: 1.5 g of intermediate 56 (38%).

b) Preparation of Intermediate 57

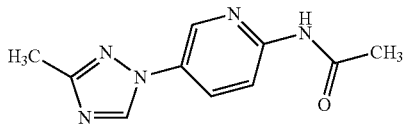 [SMILES: CC(=O)Nc1ccc(-n2cnc(C)n2)cn1]

Intermediate 56 (3.3 g, 18.8 mmol) was dissolved in THF (20 ml). $Et_3N$ (13.1 ml, 94.2 mmol) and $Ac_2O$ (17.8 ml, 188.4 mmol) were added. The r.m. was stirred at 65° C. for 18 h. The r.m. was cooled to r.t. and concentrated in vacuo. The residue was suspended in DIPE. The resulting solid was filtered off, washed with DIPE, and dried. Yield: 3.25 g of intermediate 57 (79%).

c) Preparation of Intermediate 58

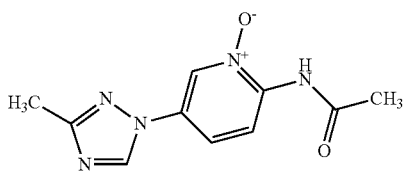 [SMILES: CC(=O)Nc1ccc(-n2cnc(C)n2)c[n+]1[O-]]

Intermediate 57 (10 g, 46.0 mmol) was dissolved in DCM (500 ml). mCPBA (14.75 g, 59.84 mmol) was added to the solution. The r.m. was stirred at r.t. for 18 h. DCM and a solution of 10% $NaHCO_3$ in $H_2O$ was added. The organic phase was separated, and washed 2 times with a solution of 10% $NaHCO_3$ in $H_2O$. The combined aq. layers were extracted 10× with DCM. The combined organic layers were dried ($MgSO_4$), filtered and the solvent was evaporated. Yield: 10.1 g of intermediate 58 (94%).

d) Preparation of Intermediate 59

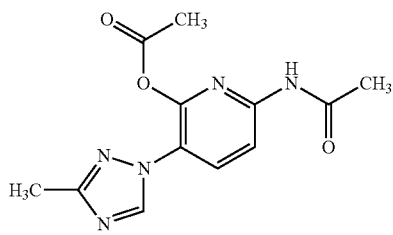 [SMILES: CC(=O)Nc1ccc(-n2cnc(C)n2)c(OC(C)=O)n1]

Intermediate 58 (10.1 g, 43.3 mmol) was dissolved in $Ac_2O$ (307 ml, 3.25 mol). The r.m. was stirred at 80° C. for 2 h. The r.m. was cooled to r.t. and concentrated in vacuo. The residue was suspended in DIPE. The resulting solid was filtered off. Yield: 10.5 g of crude intermediate 59, which was used as such in the next reaction step.

e) Preparation of Intermediate 60

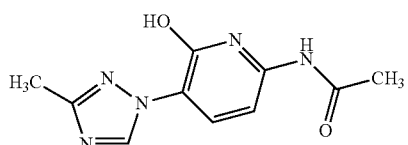

Intermediate 59 (2.5 g, 9.1 mmol) and $K_2CO_3$ (1.26 g, 9.1 mmol) were added to MeOH (30 ml). The r.m. was stirred at r.t. for 1 h. The residue was purified without evaporation of the solvent by flash column chromatography over silica gel (eluent: DCM/MeOH from 100/0 to 90/10). The product fractions were collected and the solvent was evaporated in vacuo. The residue was suspended in DIPE. The solid was filtered off, washed with DIPE, and dried. Yield: 1 g of intermediate 60 (47%).

f) Preparation of Intermediate 61

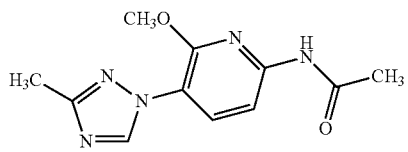

Intermediate 60 (1 g, 4.28 mmol), $CH_3I$ (0.4 ml, 6.43 mmol) and $Ag_2CO_3$ (1.18 g, 4.29 mmol) were stirred in DMF (50 ml) at 60° C. for 4 h. The r.m. was cooled to r.t. and filtered over diatomaceous earth. The filtrate was concentrated in vacuo. The residue was purified by flash column chromatography over silica gel (eluent: DCM/EtOAc from 100/0 to 0/100). The product fractions were collected and the solvent was evaporated. Yield: 450 mg of intermediate 61 (42%).

g) Preparation of Intermediate 62

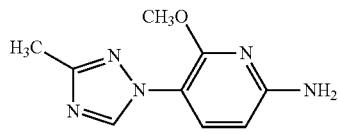

Intermediate 61 (1.1 g, 4.45 mmol) was dissolved in MeOH (120 ml) and a 10% NaOH in $H_2O$ (30 ml) was added. The r.m. was stirred at 80° C. for 3 h. The r.m. was cooled to r.t. and concentrated in vacuo. The residue was partitioned between DCM and $H_2O$. The organic layer was dried ($MgSO_4$), filtered and concentrated in vacuo. Yield: 870 mg of intermediate 62 (95%).

Example A27

Preparation of Intermediate 63

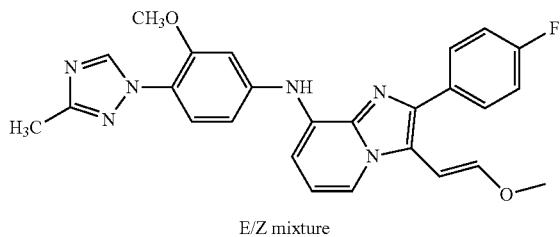

E/Z mixture

Intermediate 63 was prepared by reacting intermediates 11 and 51 in a manner identical to the procedure described for compound 181, Example B11.a.

B. Preparation of the Compounds

Example B1 a) Preparation of Compound 1

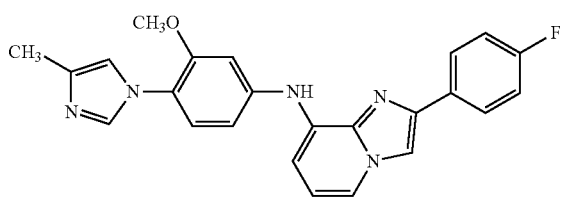

2-Methyl-2-propanol sodium salt (0.495 g, 5.15 mmol), BINAP (0.08 g, 0.13 mmol), palladium(II) diacetate (19 mg, 0.08 mmol) and intermediate 2 (0.454 g, 2.23 mmol) were added to a solution of 8-bromo-2-(4-fluorophenyl)-imidazo[1,2-a]pyridine (0.5 g, 1.72 mmol) in toluene (20 ml) and the mixture was purged with $N_2$ for 5 min. The r.m. was stirred and heated at 100° C. overnight under a $N_2$ atmosphere. EtOAc was added, and the mixture was washed with $H_2O$ and brine. The organic layer was dried ($MgSO_4$), filtered and concentrated in vacuo. The residue was purified by flash column chromatography over silicagel (eluent: DCM/MeOH from 100/0 to 98/2). The product fractions were collected and the solvent was evaporated in vacuo. The residue was crystallized form DIPE. The solid was collected and dried in vacuo. Yield: 0.49 g of compound 1 (69%).

a-1) Preparation of Compound 1 (Alternative Procedure)

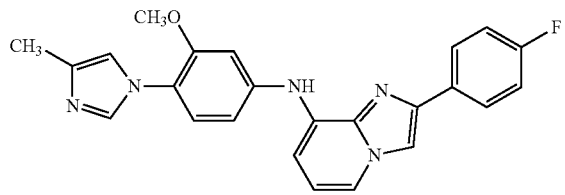

A solution of 8-bromo-2-(4-fluorophenyl)-imidazo[1,2-a]pyridine (3.2 g, 10.99 mmol) in toluene (100 ml) heated on an oil bath of 80° C., was purged with $N_2$ for 15 min. 2-Methyl-2-propanol, sodium salt (4.23 g, 43.97 mmol), BINAP (0.51 g, 0.82 mmol), palladium(II) diacetate (0.12 g, 0.55 mmol) and intermediate 2 (3.16 g, 13.19 mmol) were added and purging with $N_2$ was continued for 5 min. The oil bath was heated to 100° C. and the r.m. was stirred for 16 h at this temperature. $H_2O$ was added and further diluted with EtOAc (300 ml). The layers were separated. The aq. phase was extracted with EtOAc (3×200 ml). The combined organic layers were washed with brine, dried ($MgSO_4$), filtered and concentrated in vacuo. The residue was purified by flash column chromatography over silicagel (eluent: DCM/MeOH from 100/0 to 98/2). The product fractions were collected and the solvent was evaporated in vacuo to yield an off-white solid. This fraction was triturated under DIPE/$CH_3CN$ and stirred for 2 h. A white solid was collected and air dried. Yield: 3.74 g of compound 1 (82.3%).

b) Preparation of Compound 2

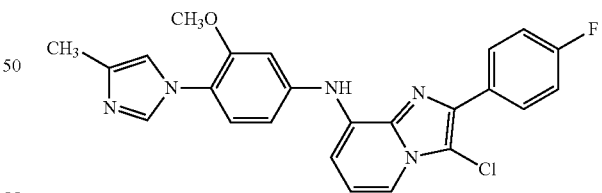

1-Chloro-2,5-pyrrolidinedione (72 mg, 0.54 mmol) was added to compound 1 (223 mg, 0.54 mmol) in DCM (25 ml) and the mixture was stirred overnight at r.t. The r.m. was quenched with an aq. NaOH solution (10 ml; 1 M solution) and the layers were separated. The organic layer was dried ($MgSO_4$), filtered, concentrated in vacuo and purified by RP preparative HPLC [RP Shandon Hyperprep® C18 BDS (8 μm, 250 g, I.D. 5 cm); mobile phase: a gradient of (0.25% $NH_4HCO_3$ solution in $H_2O$)/$CH_3CN$]. The product fractions were collected and worked up. Yield: 120 mg of Compound 2 (50%).

c) Preparation of Compound 57

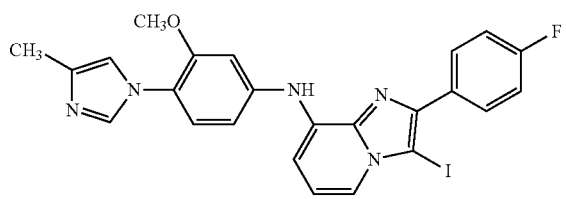

1-Iodo-2,5-pyrrolidinedione (3.282 g, 14.6 mmol) was added to compound 1 (5.02 g, 12.1 mmol) in a mixture of chloroform (500 ml) and acetic acid (20 ml). The r.m. was stirred at r.t. for 1 h, and then a 10% aq. Na$_2$SO$_3$ solution (50 ml) and chloroform (100 ml) were added. The layers were separated and the organic layer was washed successively with a 10% aq. Na$_2$SO$_3$ solution (25 ml) and a 1 N aq. NaOH solution. The organic layer was dried (MgSO$_4$), filtered, concentrated in vacuo. The residue was purified by flash column chromatography over silicagel (eluent: DCM/MeOH from 100/0 to 99/1). The product fractions were collected and the solvent was evaporated in vacuo. Yield: 5.76 g of Compound 57 (88%).

d) Preparation of Compound 58

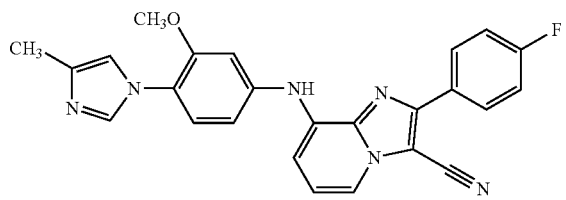

A mixture of compound 57 (500 mg, 0.927 mmol), Pd$_2$(dba)$_3$ (17 mg, 0.0185 mmol), 1,1'-bis(diphenylphosphino)ferrocene (20.5 mg, 0.037 mmol), zinc (7.3 mg, 0.11 mmol), Zn(CN)$_2$ in DMA (10 ml) was loaded in a microwave vial under a N$_2$ atmosphere. The mixture was stirred and heated at 150° C. using microwave irradiation for 1 h. The r.m. was poured into an aq. NH$_4$OH solution, and extracted with DCM. The organic layer was dried (MgSO$_4$), filtered, and concentrated in vacuo. The residue was purified by RP preparative HPLC [RP Shandon Hyperprep® C18 BDS (8 μm, 250 g, I.D. 5 cm); mobile phase: a gradient of (0.25% NH$_4$HCO$_3$ solution in H$_2$O)/MeOH/CH$_3$CN]. The product fractions were collected and worked up. Yield: 275 mg of compound 58 (68%).

e) Preparation of Compounds 122 and 100

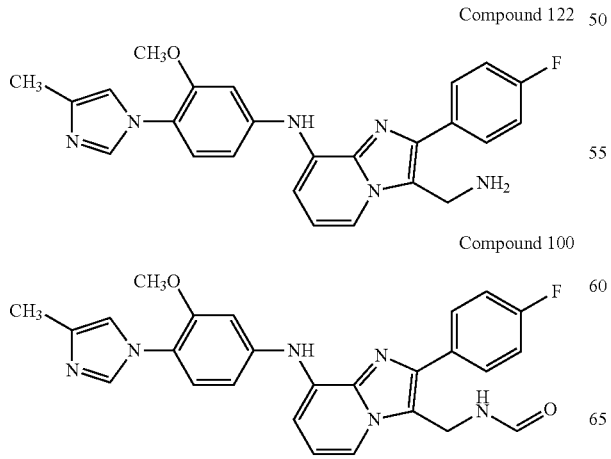

A mixture of compound 58 (150 mg, 0.34 mmol), Raney nickel (50 mg), in a 7N NH$_3$ solution in MeOH (40 ml) was stirred at 14° C. under H$_2$ (atmospheric pressure). After uptake of H$_2$ (2 eq), the catalyst was filtered off over diatomaceous earth and washed with DMF. The combined organic layers were evaporated. The residue was purified by RP preparative HPLC [RP Shandon Hyperprep® C18 BDS (10 μm, 250 g, I.D. 5 cm); mobile phase: a gradient of (0.05% TFA solution in H$_2$O and 5% CH$_3$CN)/CH$_3$CN]. The product fractions were collected and worked up. Yield: 41 mg of compound 122 (27%) and 11 mg of compound 100 (7%).

f) Preparation of Compound 101

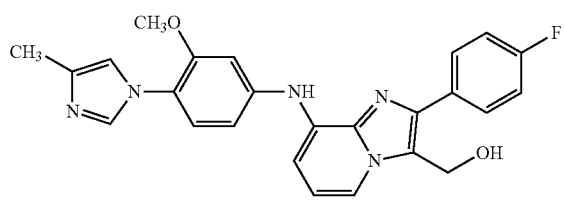

A mixture of compound 57 (1570 mg, 2.91 mmol), palladium(II) diacetate (13 mg, 0.058 mmol), 1,3-bis(diphenylphosphino)propane (48 mg, 0.116 mmol), KOAc (570 mg, 5.82 mmol) in a 1/1 mixture of THF/MeOH (20 ml) in a stainless steel autoclave was pressurized under a 30 bar CO atmosphere. The mixture was stirred and heated at 100° C. for 16 h. The r.m. was cooled and concentrated in vacuo. The residue was partitioned between DCM and H$_2$O, and the organic layer was dried (MgSO$_4$), filtered, and concentrated in vacuo. The residue was purified by flash column chromatography over silicagel (eluent: DCM/MeOH 99/1). The product fractions were collected and the solvent was evaporated in vacuo. The residue (400 mg, 0.85 mmol) was dissolved in THF (2 ml) and added to a suspension of LiAlH$_4$ (32 mg) in THF (14 ml). The mixture was stirred for 1 h at r.t. Subsequently, H$_2$O (1 ml) and a 1 N aq. NaOH (3 ml) solution were added. The resulting mixture was extracted with DCM and the organic layer was dried (MgSO$_4$), filtered, and concentrated in vacuo. The residue was purified by flash column chromatography over silicagel (eluent: DCM/MeOH 99/1). The product fractions were collected and the solvent was evaporated in vacuo. The residue was suspended in DIPE and dried in vacuo. Yield: 46 mg of compound 101 (12%).

Example B2

Preparation of Compound 3

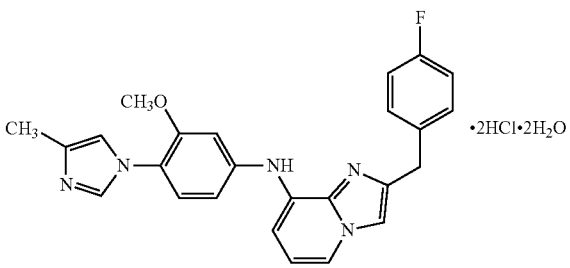

2-Methyl-2-propanol, sodium salt (384.42 mg, 4 mmol), BINAP (46.7 mg, 0.075 mmol), palladium(II) diacetate (11.33 mg, 0.05 mmol) and intermediate 2 (359.56 mg, 1.5 mmol) were added to a solution of intermediate 4 (305.15 mg, 1 mmol) in toluene (10 ml; previously deoxygenated) under a $N_2$ atmosphere. The r.m. was heated overnight at 100° C. Subsequently, $H_2O$ was added and the mixture was extracted with DCM. The organic phase was separated, dried ($MgSO_4$), filtered and the solvent was evaporated in vacuo. The residue was purified by flash column chromatography (eluent: DCM/MeOH($NH_3$) from 100/0 to 96/4). The product fractions were collected and the solvent was evaporated in vacuo. The residue was dissolved in $Et_2O$, and then 1 N HCl in $Et_2O$ was added. The precipitate (HCl salt) was filtered off and dried. Yield: 0.145 g of compound 3 (27.0%; .2HCl.2H$_2$O).

Example B3

Preparation of Compound 4

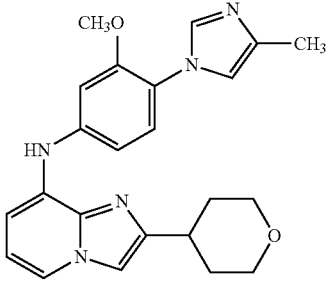

Intermediate 2 (0.106 g, 0.44 mmol), palladium(II) diacetate (0.004 g, 0.017 mmol), 2-methyl-2-propanol, sodium salt (0.131 g, 1.37 mmol) and BINAP (0.016 g, 0.026 mmol) were added to a solution of intermediate 7 (0.096 g, 0.34 mmol) in toluene (5 ml) under a $N_2$ atmosphere. $N_2$ gas was bubbled through the suspension and the suspension was heated overnight at 100° C. The r.m. was allowed to cool to r.t. and was then diluted with EtOAc and washed with $H_2O$ and brine. The organic layer was dried ($MgSO_4$), filtered and the solvent was evaporated. The product was purified by flash column chromatography over silicagel (eluent: DCM/MeOH from 100/1 to 20/1). The product fractions were collected and the solvent was evaporated in vacuo. The residue was recrystallized from DIPE. The product was dried in vacuo at r.t. Yield: 0.079 g of compound 4 (57%).

Example B4

Preparation of Compound 5

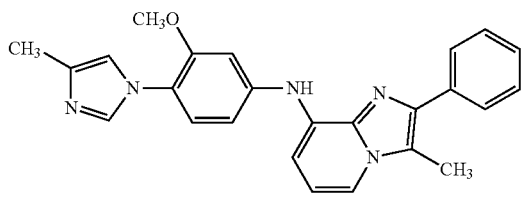

2-Methyl-2-propanol, sodium salt (256 mg, 2.66 mmol), BINAP (31.1 mg, 0.05 mmol), palladium(II) diacetate (7.54 mg, 0.033 mmol) and intermediate 2a (203 mg, 1 mmol) were added to a solution of intermediate 8 (191.21 mg, 0.67 mmol) in toluene (8 ml; previously deoxygenated) under a $N_2$ atmosphere. The r.m. was heated overnight at 100° C. Then, $H_2O$ was added and the mixture was extracted with DCM. The organic phase was separated, dried ($MgSO_4$), filtered and the solvent was evaporated in vacuo. The residue was purified by flash column chromatography over silicagel (Eluent: DCM/MeOH($NH_3$) from 100/0 to 96/4). The desired fractions were collected and the solvent was evaporated in vacuo. The residue was crystallized from DIPE/$CH_3CN$. The precipitate was filtered off and dried. Yield: 0.195 g of compound 5 (71.5%).

Example B5

Preparation of Compound 6

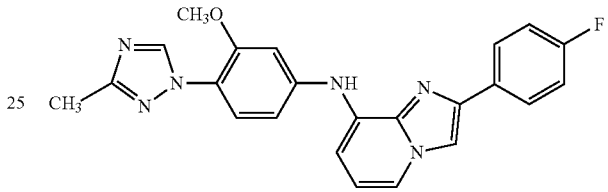

2-Methyl-2-propanol, sodium salt (276 mg, 2.78 mmol), BINAP (45 mg, 0.07 mmol), palladium(II) diacetate (10 mg, 0.046 mmol) and intermediate 11 (189 mg, 0.93 mmol) were added to a solution of intermediate 12 (270 mg, 0.93 mmol) in toluene (5 ml; previously degassed and put under $N_2$). The r.m. was degassed and put under a $N_2$ atmosphere. The r.m. was stirred overnight at 100° C. $H_2O$ (q.s.) was added and the mixture was extracted with DCM. The organic layer was dried ($MgSO_4$), filtered and the solvent was evaporated. The residue was purified by column chromatography over silicagel (eluent: DCM/MeOH 99/1). The product fractions were collected and evaporated. The residue was suspended in DIPE (q.s.) and a drop of $CH_3CN$. The product was filtered off and dried in vacuo at 50° C. Yield: 73 mg of compound 6.

Example B6

Preparation of Compound 7

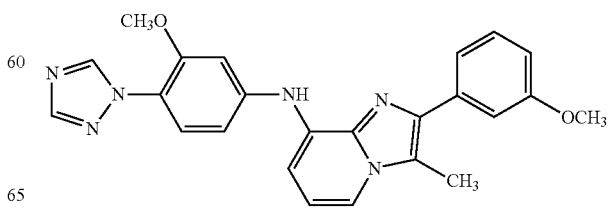

Intermediate 14 (190 mg, 1 mmol), Pd$_2$(dba)$_3$ (92 mg, 0.1 mmol), X-Phos (105 mg, 0.22 mmol) and Cs$_2$CO$_3$ (978 mg, 3 mmol) were added to a solution of intermediate 15 (317 mg, 1 mmol) in 2-methyl-2-propanol (5 ml) under a N$_2$ atmosphere. The r.m. was heated at 110° C. for 20 h. H$_2$O was added and the mixture was extracted with DCM. The organic layer was dried (MgSO$_4$), filtered and the solvent was evaporated. The residue was purified by flash chromatography over silicagel (eluent: DCM/MeOH(NH$_3$) 100/0 to 98/2). The first product fraction was collected and the solvent was evaporated: Yield: 0.038 g of compound 7 (8.9%). A second product fraction was collected and the solvent was evaporated, yielding 250 mg of crude compound 7. This crude fraction was further purified by RP preparative HPLC [RP Shandon Hyperprep® C18 BDS (8 μm, 250 g, I.D. 5 cm); mobile phase: a gradient of (0.25% NH$_4$HCO$_3$ solution in H$_2$O)/MeOH/CH$_3$CN]. The product fractions were collected and worked up. Yield: 181 mg of compound 7 (42.4%).

Example B7

Preparation of Compound 63

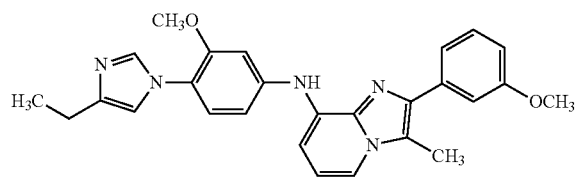

Intermediate 30 (220 mg, 0.466 mmol) was added to a mixture of NH$_4$(OAc) (0.179 g, 2.32 mmol) in acetic acid (3 ml). The r.m. was heated at reflux for 1 h. The r.m. was neutralized to pH 7 with an aq. 1 N NaOH solution, and then extracted with EtOAc. The organic layer was washed with brine, dried (MgSO$_4$), filtered and concentrated in vacuo. The product was purified by flash column chromatography over silicagel (eluent: DCM/MeOH(NH$_3$) from 100/0 to 96/4). The product fractions were collected and the solvent was evaporated. The residue was purified further by RP preparative HPLC [RP Shandon Hyperprep® C18 BDS (8 μm, 250 g, I.D. 5 cm); mobile phase: a gradient of (0.25% NH$_4$HCO$_3$ solution in H$_2$O)/MeOH/CH$_3$CN]. The product fractions were collected and worked up. Yield: 88 mg of compound 63 (41.7%).

Example B8 a) Preparation of Compound 107

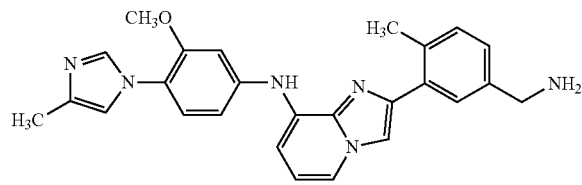

A mixture of compound 105 (prepared analogously to compound 7, Example B6) (432 mg, 0.99 mmol), Raney nickel (200 mg), in a 7 N NH$_3$ solution in MeOH (100 ml) was stirred at 14° C. under H$_2$ (atmospheric pressure). After uptake of H$_2$ (2 eq), the catalyst was filtered off over diatomaceous earth and washed with MeOH. The combined organic layers were concentrated in vacuo. The residue was partitioned between DCM and H$_2$O and the organic layer was dried (MgSO$_4$), filtered, and concentrated. The residue was purified by flash column chromatography over silicagel (eluent: DCM/MeOH(NH$_3$) 100/0 to 90/10). The product fractions were collected and the solvent was evaporated in vacuo. Yield: 350 mg of compound 107 (80%).

b) Preparation of Compound 111

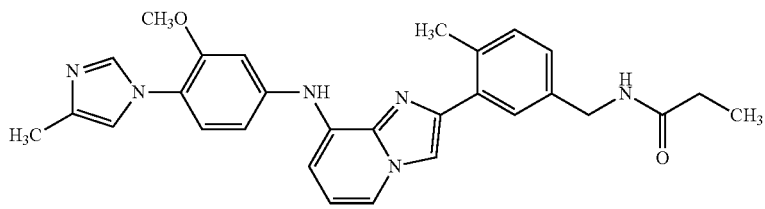

n-Propionylchloride (3.8 µl, 0.043 mmol) was added to an ice-cooled mixture of compound 107 (20 mg, 0.046 mmol) and Et₃N (13 µl, 0.091 mmol) in DCM (1 ml). The r.m. was stirred at r.t. for 24 h. The solvent was evaporated and the residue was partitioned between DCM and H₂O. The organic layer was dried (MgSO₄), filtered and concentrated in vacuo. The product was purified by flash column chromatography over silicagel (eluent: DCM/MeOH(NH₃) from 100/0 to 93/7). The product fractions were collected and the solvent was evaporated. Yield: 10 mg of compound III (44%).

c) Preparation of Compound 114

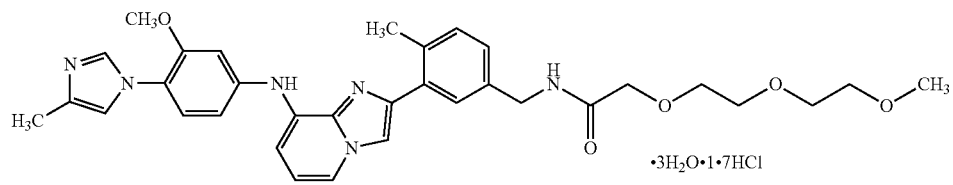

HBTU (107 mg, 0.28 mmol) was added to a solution of [2-(2-methoxy-ethoxy)-ethoxy]-acetic acid (40 µl, 0.26 mmol) and DIPEA (57 µL, 0.32 mmol) in DMF (1 ml). After stirring for 10 min at r.t., compound 107 (95 mg, 0.22 mmol) was added to the mixture and the r.m. was stirred at r.t. for 2 h. The solvent was evaporated and the residue was dissolved in DCM. The organic layer was washed with H₂O and with a sat. aq. Na₂CO₃ solution, was dried (MgSO₄), filtered and concentrated in vacuo. The product was purified by flash column chromatography over silicagel (eluent: DCM/MeOH (NH₃) from 100/0 to 98/2). The product fractions were collected and the solvent was evaporated. The resulting oil was dissolved in CH₃CN and converted into the HCl salt by adding a 6 N HCl solution in 2-propanol. The precipitate was filtered off and dried in vacuo. Yield: 36 mg of compound 114 (23%; .3H₂O.1.7HCl).

Example B9

Preparation of Compound 117

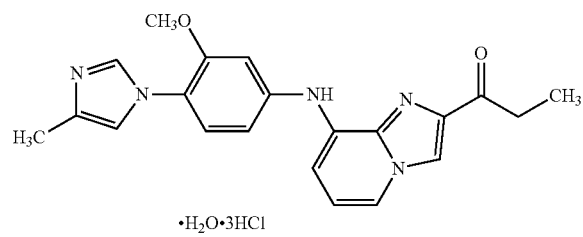

A 1 M solution of CH₃CH₂MgBr in THF (0.49 ml, 0.49 mmol) was added to an ice-cooled solution of intermediate 43 (50 mg, 0.12 mmol) in THF (1 ml) under N₂ atmosphere. The r.m. was warmed up to r.t. and stirred for 2 h, then cooled again to 0° C. and more CH₃CH₂MgBr (0.25 ml, 0.25 mmol) was added. The solution was warmed up to r.t., stirred for 2 h, cooled again to 0° C., and again CH₃CH₂MgBr (0.25 ml, 0.25 mmol) was added. The r.m. was warmed up to r.t. and stirred for 2 h. H₂O was added and the solution was acidified until pH 3 using an aq. 1 N HCl solution. The solution was stirred for 45 min and was basified using NaHCO₃. The volatiles were evaporated. The product was extracted 3× with DCM. The combined organic layers were dried (MgSO₄), filtered and evaporated under reduced pressure. The residue was purified by RP preparative HPLC [RP Vydac Denali C18 (10 µm, 250 g, I.D. 5 cm); mobile phase: a gradient of (0.25% NH₄HCO₃ solution in H₂O)/CH₃CN]. The product fractions were collected and worked up. The resulting oil was dissolved in CH₃CN and a 6 N HCl solution in 2-propanol was added. The precipitate was filtered off and dried in vacuo. Yield: 15 mg of compound 117 (32%; .H₂O.3HCl).

Example B10

Preparation of Compound 127

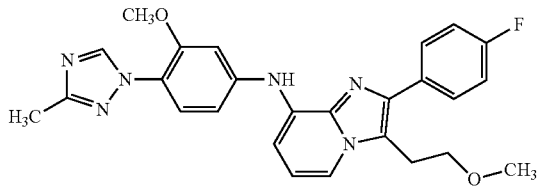

A mixture of intermediate 63 (350 mg, 0.74 mmol) and Raney nickel (50 mg), in THF (40 ml) was stirred at r.t. under H₂ (atmospheric pressure). After uptake of H₂ (1 eq), the catalyst was filtered off over diatomaceous earth. The solvent was evaporated and the residue was partitioned between DCM and H₂O. The organic layer was dried (MgSO₄), filtered and concentrated in vacuo. The product was purified by flash column chromatography over silicagel (eluent: DCM/ MeOH from 99/1). The product fractions were collected and the solvent was evaporated. The residue was triturated with DIPE and a drop of CH₃CN. The product was then dried in vacuo. Yield: 26 mg of compound 127 (7%).

Example B11 a) Preparation of Compound 181

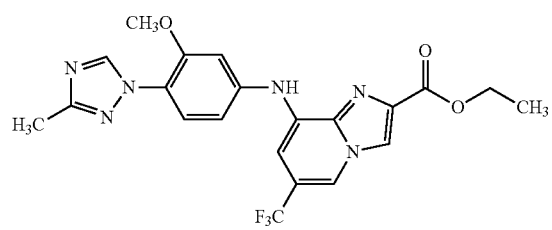

Intermediate 11 (408 mg, 2 mmol), Pd$_2$(dba)$_3$ (184 mg, 0.2 mmol), X-phos (0.21 g, 0.0.44 mmol) and Cs$_2$CO$_3$ (1.95 g, 6 mmol) were added to a solution of ethyl 8-iodo-6-(trifluoromethyl)imidazo[1,2-a]pyridine-2-carboxylate (0.768 g, 2 mmol) in 2-methyl-2-propanol (10 ml) under a N$_2$ atmosphere. The r.m. was heated at 100° C. for 2 h. Then, H$_2$O was added and the mixture was extracted with EtOAc. The organic layer was washed with brine, dried (MgSO$_4$), filtered and the solvent was evaporated. The residue was purified by flash chromatography over silicagel (eluent: DCM/MeOH from 100/0 to 97/3). The product fraction was collected and the solvent was evaporated: Yield: 0.509 g of compound 181 (55%).

b) Preparation of Compound 152

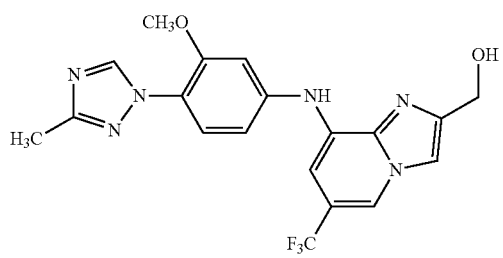

A solution of compound 181 (0.509 g, 1.1 mmol) in THF (3.3 ml) was added dropwise to a suspension of LiAlH$_4$ (84 mg, 2.2 mmol) in THF (10 ml). The r.m. was stirred at r.t for 1 h and was then diluted with EtOAc. The organic layer was washed with a 3 N aq. NaOH solution, dried (MgSO$_4$), filtered and evaporated under reduced pressure. The product was purified by flash column chromatography over silicagel (eluent: DCM/MeOH from 50/1 to 10/1). The product fractions were collected and the solvent was evaporated. Yield: 377 mg of compound 152 (82%).

c) Preparation of Compound 147

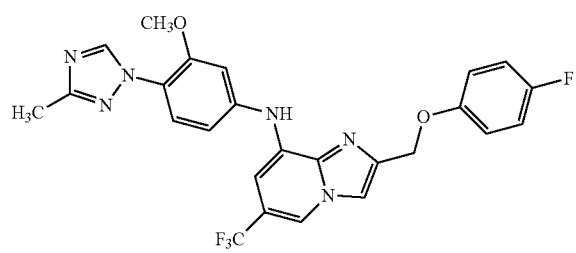

Diisopropyl azodicarboxylate (0.12 ml, 0.62 mmol) was added to a solution of PPh$_3$ (0.167 g, 0.64 mmol) in THF (40 ml) at 0° C. The mixture was stirred for 30 min. Subsequently, compound 152 (0.172 g, 0.41 mmol) and 4-fluorophenol (46 mg, 0.41 mmol) were added. The r.m. was stirred at r.t. for 2 h and was then partitioned between DCM and an aq. 1 N NaOH solution. The organic layer was dried (MgSO$_4$), filtered and evaporated under reduced pressure. The residue was purified by RP preparative HPLC [RP Luna C18, mobile phase: gradient of (25 mM aq. NH$_4$HCO$_3$ solution)/(1/1 CH$_3$CN/MeOH) from 47/53 to 18/82)]. The product fractions were collected and worked up. Yield: 46 mg of compound 147 (22%).

Example B12 a) Preparation of Compound 154

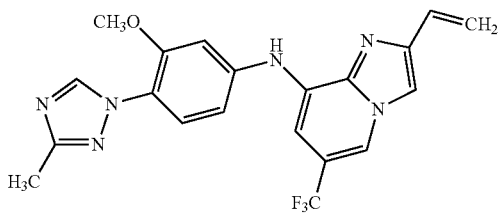

Intermediate 11 (38 mg, 0.15 mmol), Pd$_2$(dba)$_3$ (14 mg, 0.015 mmol), X-phos (14 mg, 0.015 mmol) and Cs$_2$CO$_3$ (145 mg, 0.44 mmol) were added to a solution of intermediate 45 (50 mg, 0.15 mmol) in 2-methyl-2-propanol (5 ml) under a N$_2$ atmosphere. The r.m. was heated at 100° C. for 18 h. Then, H$_2$O was added and the mixture was extracted with DCM. The organic layer was dried (MgSO$_4$), filtered and the solvent was evaporated. The residue was purified by flash chromatography over silicagel (eluent: Et$_2$O/heptane from 1/1 to 2/1). The product fraction was collected and the solvent was evaporated. Yield: 0.034 g of compound 154 (54%).

b) Preparation of Compound 153

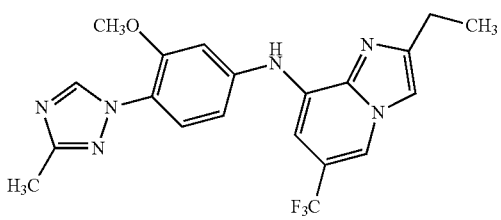

THF (40 ml) was added to Pd/C (10%, 30 mg) under a N$_2$ atmosphere. Subsequently, a 0.4% thiophene solution in DIPE (1 ml) and compound 154 (30 mg, 0.072 mmol) were added. The r.m. was stirred at 25° C. under a H$_2$ atmosphere until 1 eq of H$_2$ was absorbed. The catalyst was filtered off over diatomaceous earth. The filtrate was evaporated and the residue was purified by flash chromatography over silicagel (eluent: eluent: Et$_2$O/heptane from 1/1 to 1/0). The product fraction was collected and the solvent was evaporated. Yield: 0.027 g of compound 153 (88%).

Example B13

Preparation of Compound 159

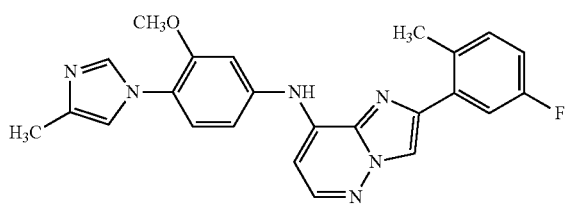

A 1/1 mixture of THF and MeOH (100 ml) was added to Pd/C (10%, 500 mg) under a N₂ atmosphere. Subsequently, a 0.4% thiophene solution in DIPE (1 ml), compound 157 (prepared according to example B6, 141 mg, 0.3 mmol), and KOAc (36 mg, 0.36 mmol) were added, and the r.m. was stirred at 25° C. under a H₂ atmosphere until 1 eq of H₂ was absorbed. The catalyst was filtered off over diatomaceous earth. The filtrate was evaporated and the residue was partitioned between DCM and a sat. aq. NaHCO₃ solution. The organic layer was dried (MgSO₄), filtered and the solvent was evaporated. Yield: 0.103 g of compound 159 (79%).

Example B14 a) Preparation of Compound 174

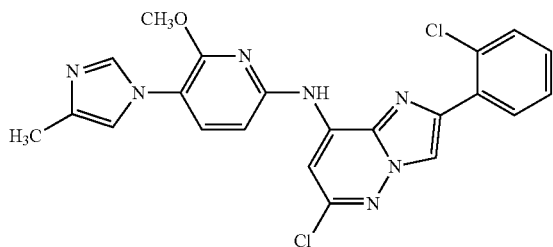

Intermediate 34 (1.22 g, 6 mmol), Pd₂(dba)₃ (640 mg, 0.0.7 mmol), X-phos (670 mg, 1.4 mmol) and Cs₂CO₃ (6.87 g, 21 mmol) were added to a solution of intermediate 55 (2.74 g, 6 mmol) in 2-methyl-2-propanol (50 ml) under a N₂ atmosphere. The r.m. was heated at 100° C. for 16 h. Then, H₂O was added and the mixture was extracted with DCM. The combined organic layers were dried (MgSO₄), filtered and the solvent was evaporated. The residue was purified by flash chromatography over silicagel (eluent: DCM/MeOH(NH₃) from 100/0 to 97/3). The product fraction was collected and the solvent was evaporated: Yield: 1.2 g of compound 174 (34%).

b) Preparation of Compound 171

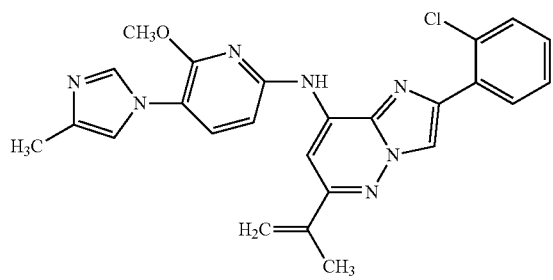

2-Isopropenyl-4,4,5,5-tetramethyl-[1,3,2]dioxaborolane (132 mg, 0.79 mmol) and Pd(PPh₃)₄ (38 mg, 0.033 mmol) were added to a mixture of compound 174 (306 mg, 0.66 mmol) in dioxane (10 ml) and an aq. sat. NaHCO₃ solution (5 ml). The r.m. was heated under microwave conditions at 160° C. for 10 min. The r.m. was cooled and filtered over diatomaceous earth, using EtOAc as eluent. The filtrate was evaporated and the residue was purified by flash chromatography over silicagel (eluent: DCM/MeOH(NH₃) from 100/0 to 97/3). Yield: 0.25 g of compound 171 (81%).

c) Preparation of Compound 163

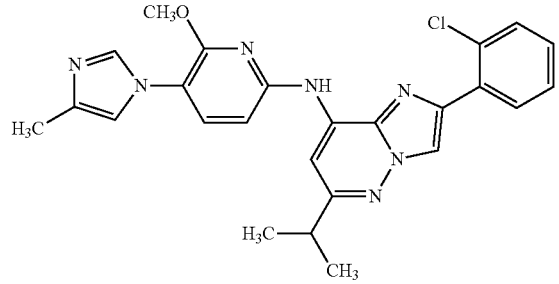

Compound 171 (120 mg, 0.25 mmol) was added to a mixture of MeOH (40 ml) and Pt/C (5%, 50 mg) under a N₂ atmosphere. The r.m. was stirred at 25° C. under a H₂ atmosphere until 1 eq of H₂ was absorbed. The mixture was filtered over diatomaceous earth. The filtrate was evaporated and the residue was purified by flash chromatography over silicagel (eluent: DCM/MeOH from 100/0 to 95/5). The product fraction was collected and the solvent was evaporated. Yield: 0.055 g of compound 163 (46%).

Example B15 a) Preparation of Compound 177

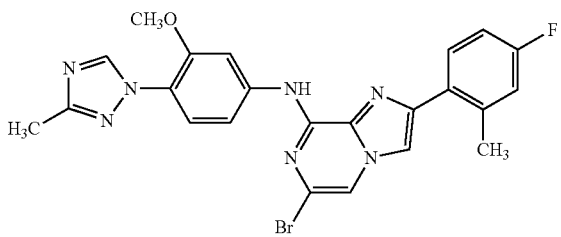

A solution of intermediate 11 (318 mg, 1.56 mmol), intermediate 54 (400 mg, 1.04 mmol) and DIPEA (269 mg, 2.08 mmol) in CH₃CN (5 ml) was heated under microwave conditions first for 3 h at 160° C., and then for 2 h at 170° C. The r.m. was cooled and the resulting precipitate was filtered off, washed with CH₃CN and DIPE, and dried. The precipitate was purified further by flash chromatography over silicagel (eluent: DCM/MeOH from 100/0 to 97/3). The product fraction was collected and the solvent was evaporated: Yield: 0.044 g of compound 177 (8%).

b) Preparation of Compound 176

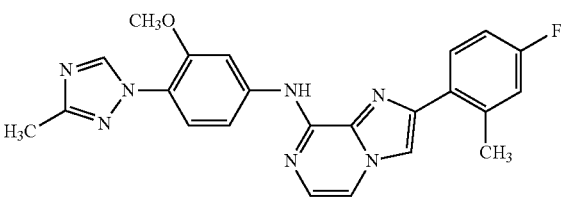

MeOH (40 ml) was added to Pd/C (10%, 50 mg) under a N₂ atmosphere. Subsequently, a 0.4% thiophene solution in DIPE (1 ml) was added and the mixture was stirred at 25° C. under a H₂ atmosphere for 30 min. Compound 177 (100 mg, 0.2 mmol) and KOAc (39 mg, 0.39 mmol) were added and the r.m. was stirred at 25° C. under a H₂ atmosphere until 1 eq of H₂ was absorbed. The catalyst was filtered off over diatomaceous earth. The filtrate was evaporated and the residue was purified by flash chromatography over silicagel (eluent: eluent: DCM/MeOH from 100/0 to 95/5). The product fraction was collected and the solvent was evaporated. The residue was triturated with DIPE and dried in vacuo. Yield: 0.065 g of compound 176 (77%).

Example B16

Preparation of Compound 145

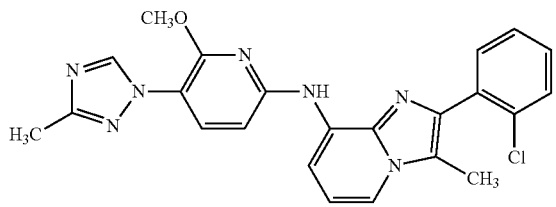

Intermediate 62 (160 mg, 0.78 mmol), Pd₂(dba)₃ (71 mg, 0.078 mmol), X-phos (74 mg, 0.156 mmol) and Cs₂CO₃ (762 mg, 2.34 mmol) were added to a solution of 8-bromo-2-(2-chloro-phenyl)-3-methyl-imidazo[1,2a]pyridine (prepared according to synthesis protocol described in example A9; 301 mg, 0.94 mmol) in 2-methyl-2-propanol (20 ml) under a N₂ atmosphere. The r.m. was heated at 100° C. for 16 h. Then, the r.m. was cooled to r.t., H₂O was added and the mixture was extracted with DCM. The combined organic layers were dried (MgSO₄), filtered and concentrated in vacuo. The residue was purified by flash column chromatography over silica gel (eluent: DCM/MeOH from 100/0 to 95/5). The product fractions were collected and concentrated in vacuo. The residue was triturated with DIPE. The solid was collected and dried in vacuo. Yield: 0.210 g of compound 145 (60%).

Example B17 a) Preparation of Compound 182

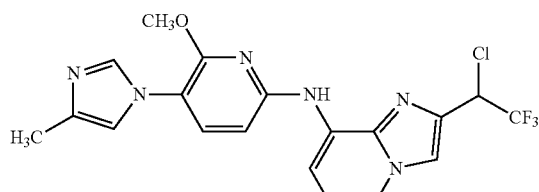

Intermediate 34 (195 mg, 0.96 mmol), Pd₂(dba)₃ (88 mg, 0.096 mmol), X-Phos (100 mg, 0.211 mmol) and Cs₂CO₃ (935 mg, 2.87 mmol) were added to a solution of intermediate 65 (300 mg, 0.96 mmol) in 2-methyl-2-propanol (23 ml) under a N₂ atmosphere. The r.m. was heated at 110° C. overnight. H₂O was added and the mixture was extracted with DCM. The organic layer was dried (MgSO₄), filtered and the solvent was evaporated. The residue was purified by flash chromatography over silicagel (eluent: DCM/MeOH(NH₃) 100/0 to 97/3). The product fractions were collected and the solvent was evaporated: Yield: 0.020 g of compound 182 (5%).

b) Preparation of Compound 179

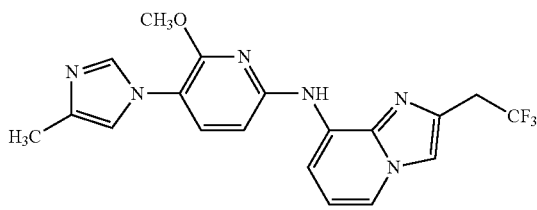

MeOH (30 ml) was added to Pd/C 10% (20 mg) under a N₂ atmosphere. Subsequently, a 0.4% thiophene solution in DIPE (0.1 ml) and compound 182 (20 mg, 0.046 mmol) were added. The r.m. was stirred at 25° C. under a H₂ atmosphere until 1 eq of H₂ was absorbed. The catalyst was filtered off over diatomaceous earth. The filtrate was evaporated and the residue was purified by flash column chromatography over silica gel (eluent: DCM/MeOH from 100/0 to 97/3). The product fractions were collected and concentrated in vacuo. The residue was triturated with DIPE. The solid was collected and dried in vacuo. Yield: 5 mg of compound 179 (27%).

Compounds 1 to 71, 73 to 84, 86 to 91, 94, 98 and 100 to 182 in tables 1, 2, 3, 4, 5, 6, 7, 8, 9 and 10 list the compounds that were prepared by analogy to one of the above Examples. In case no salt form is indicated, the compound was obtained as a free base. Compounds 72, 85, 92, 93, 95, 96, 97 and 99 in tables 2, 5 and 6 list the compounds that can be prepared by analogy to one of the above Examples. 'Pr.' refers to the Example number according to which protocol the compound was or can be synthesized. 'Co. No.' means compound number. The Example numbers indicated with an asterisk '*' were described in detail in the Examples section.

TABLE 1
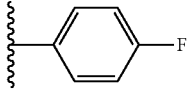
| Co. No. | Pr. | R⁰ | R¹ | R² | R³ | R⁴ | salt form |
|---|---|---|---|---|---|---|---|
| 8 | B1.a | H | CH₃ | CH₃O | H | 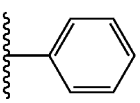 | |
| 9 | B1.a | H | CH₃ | CH₃O | C(CH₃)₃ | H | |
| 10 | B1.a | H | CH₃ | CH₃O | (CH₂)₂—CH₃ | CH₂—CH₃ | |
| 11 | B1.a | H | CH₃ | CH₃O | (CH₂)₃—CH₃ | (CH₂)₂—CH₃ | |
| 12 | B1.a | H | CH₃ | CH₃O | 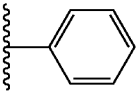 | H | |
| 5 | B4* | H | CH₃ | CH₃O | 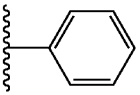 | CH₃ | |
| 13 | B1.a | H | CH₃ | CH₃O | 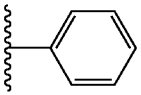 | 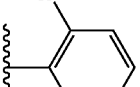 | |
| 14 | B1.a | H | CH₃ | CH₃O | 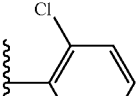 | H | |
| 15 | B1.a | H | CH₃ | CH₃O | 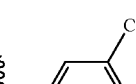 | CH₃ | |
| 16 | B1.a | H | CH₃ | CH₃O |  | H | |
| 17 | B1.a | H | CH₃ | CH₃O | 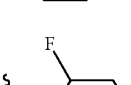 | H | |
| 88 | B1.a | H | CH₃ | CH₃O | 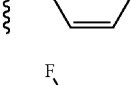 | H | |
| 18 | B1.a | H | CH₃ | CH₃O | 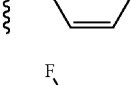 | CH₃ | |

TABLE 1-continued

| Co. No. | Pr. | R⁰ | R¹ | R² | R³ | R⁴ | salt form |
|---|---|---|---|---|---|---|---|
| 19 | B1.a | H | CH₃ | CH₃O | 3-F-phenyl | H | |
| 1 | B1.a* | H | CH₃ | CH₃O | 4-F-phenyl | H | |
| 20 | B1.a | CH₃ | CH₃ | CH₃O | 4-F-phenyl | H | |
| 21 | B1.a | CH₃ | H | CH₃O | 4-F-phenyl | H | |
| 22 | B1.b | H | CH₃ | CH₃O | 4-F-phenyl | Br | |
| 2 | B1.b* | H | CH₃ | CH₃O | 4-F-phenyl | Cl | |
| 23 | B1.a | H | CH₃ | CH₃O | 4-F-phenyl | CH₂—CH₃ | |
| 24 | B2 | H | CH₃ | CH₃O | 4-F-phenyl | (CH₂)₂—CH₃ | •2HCl |
| 25 | B1.a | H | CH₃ | CH₃O | 2,4-di-F-phenyl | H | |
| 26 | B1.a | H | CH₃ | CH₃O | 2,4-di-F-phenyl | CH₃ | |

TABLE 1-continued
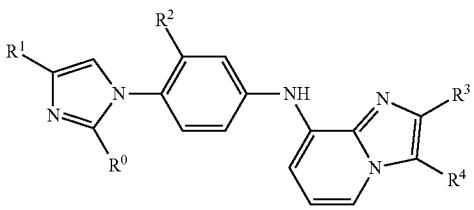
| Co. No. | Pr. | R⁰ | R¹ | R² | R³ | R⁴ | salt form |
|---|---|---|---|---|---|---|---|
| 27 | B1.a | H | CH₃ | CH₃O | 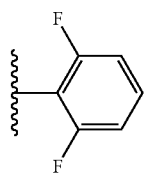 | CH₃ | |
| 3 | B2* | H | CH₃ | CH₃O | 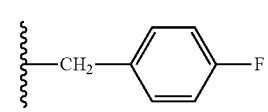 | H | •2HCl •2H₂O |
| 28 | B1.a | H | CH₃ | CH₃O | 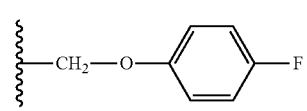 | H | |
| 29 | B2 | H | CH₃ | CH₃O | 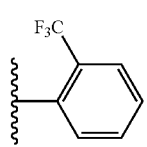 | CH₃ | •2HCl |
| 30 | B1.a | H | CH₃ | CH₃O | 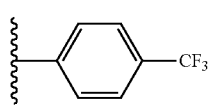 | H | |
| 31 | B1.a | H | CH₃ | CH₃O | 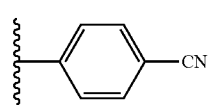 | H | |
| 32 | B1.a | H | CH₃ | CH₃O | 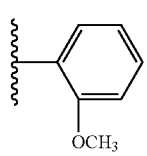 | H | |
| 33 | B1.a | H | CH₃ | CH₃O | 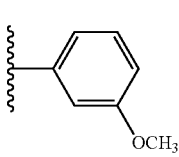 | H | |
| 34 | B1.a | H | CH₃ | CH₃O | 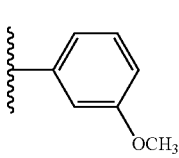 | CH₃ | |

TABLE 1-continued

| Co. No. | Pr. | R⁰ | R¹ | R² | R³ | R⁴ | salt form |
|---|---|---|---|---|---|---|---|
| 35 | B1.a | H | H | CH₃O | 3-methoxyphenyl | CH₃ | |
| 36 | B1.a | H | CH₃ | CH₃O | 4-methoxyphenyl | H | |
| 37 | B1.a | H | CH₃ | CH₃O | 2,4-dimethoxyphenyl | H | |
| 38 | B1.a | H | CH₃ | CH₃O | 4-isobutylphenyl | CH₃ | |
| 39 | B1.a | H | CH₃ | CH₃O | 4-(N,N-diethylamino)phenyl | H | |
| 40 | B1.a | H | CH₃ | CH₃O | 4-morpholinophenyl | H | |
| 41 | B1.a | H | CH₃ | CH₃O | pyridin-2-yl | H | |
| 42 | B1.a | H | CH₃ | CH₃O | pyridin-3-yl | H | |
| 43 | B1.a | H | CH₃ | CH₃O | pyridin-4-yl | H | |
| 4 | B3* | H | CH₃ | CH₃O | tetrahydropyran-4-yl | H | |

TABLE 1-continued
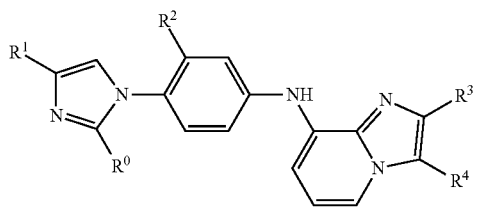
| Co. No. | Pr. | R⁰ | R¹ | R² | R³ | R⁴ | salt form |
|---|---|---|---|---|---|---|---|
| 44 | B1.a | H | $CH_3$ | $CH_3O$ | 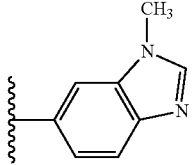 [SMILES: *c1ccc2ncn(C)c2c1] | H | |
| 47 | B1.a | H | $CH_3$ | $CH_3O$ | 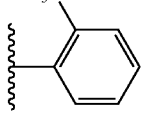 | H | |
| 48 | B1.a | H | $CH_3$ | $CH_3O$ | 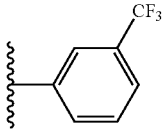 [SMILES: *c1cccc(C(F)(F)F)c1] | H | |
| 49 | B1.a | H | $CH_3$ | $CH_3O$ | H | H | |
| 50 | B1.a | H | $CH_3$ | $CH_3O$ | $CH_3$ | H | |
| 69 | B1.a | H | $CH_3$ | $CH_3O$ | $(CH_2)_3-CH_3$ | H | |
| 51 | B2 | H | $CH_3$ | $CH_3O$ | $(CH_2)_3-CH_3$ | H | •2HCl |
| 52 | B1.a | H | $CH_3$ | $CH_3O$ | 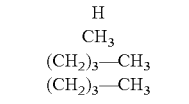 | H | |
| 53 | B1.a | H | $CH_3$ | $CH_3O$ | 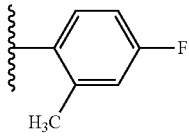 | Cl | |
| 54 | B1.a | H | $CH_3$ | $CH_3O$ | 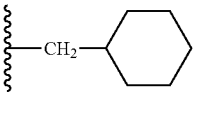 | H | •2HCl |
| 55 | B1.a | H | $CH_3$ | \$CH_3O$ | 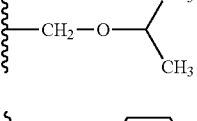 | H | |
| 56 | B1.a | H | $CH_3$ | $CH_3O$ | 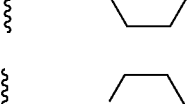 | H | |
| 57 | B1.c* | H | $CH_3$ | $CH_3O$ | 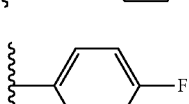 | I | |

TABLE 1-continued
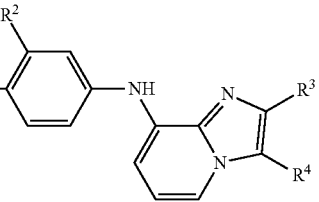
| Co. No. | Pr. | $R^0$ | $R^1$ | $R^2$ | $R^3$ | $R^4$ | salt form |
|---|---|---|---|---|---|---|---|
| 58 | B1.d* | H | $CH_3$ | $CH_3O$ | 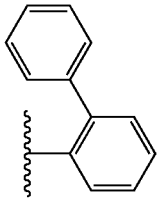 [SMILES: *c1ccccc1-c1ccccc1] | CN | |
| 59 | B1.a | H | $CH_3$ | $CH_3O$ | H | $(CH_2)_5$—$CH_3$ | |
| 60 | B1.a | H | $CH_3$ | $CH_3O$ | H | 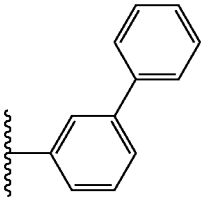 [SMILES: *c1cccc(-c2ccccc2)c1] | |
| 61 | B1.a | H | $CH_3$ | $CH_3O$ | H | 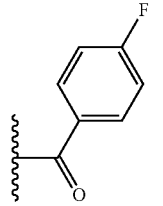 [SMILES: *C(=O)c1ccc(F)cc1] | |
| 62 | B1.a | H | $CH_3$ | $CH_3O$ | H | 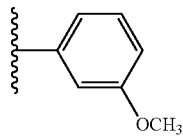 [SMILES: *c1cccc(OC)c1] | |
| 63 | B7* | H | $CH_2$—$CH_3$ | $CH_3O$ | 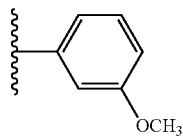 | $CH_3$ | |
| 64 | B6 | H | $CH_3$ | H | 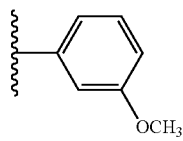 | $CH_3$ | |
| 65 | B6 | $CH_3$ | H | H | 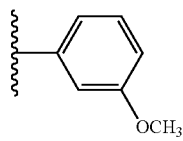 | $CH_3$ | |

TABLE 1-continued

| Co. No. | Pr. | R⁰ | R¹ | R² | R³ | R⁴ | salt form |
|---|---|---|---|---|---|---|---|
| 66 | B6 | H | CH₃ | F | 3-methoxyphenyl | CH₃ | |
| 100 | B1-e* | H | CH₃ | CH₃O | 3-fluorophenyl | CH₂—NH—CH=O | |
| 101 | B1-f* | H | CH₃ | CH₃O | 4-fluorophenyl | CH₂—OH | |
| 102 | B6 | H | CH₃ | F | 2-chlorophenyl | CH₂—N(CH₃)—C(=O)—CH₃ | |
| 103 | B6 | H | CH₃ | F | 2-chlorophenyl | CH₂—O—CH₃ | |
| 104 | B6 | H | CH₃ | F | phenyl | CH₂—O—CH₃ | |
| 105 | B6 | H | CH₃ | CH₃O | 4-methyl-3-cyanophenyl (2-methyl-5-cyano) | H | |
| 106 | B6 | H | CH₃ | CH₃O | C(=O)—O—C(CH₃)₃ | H | •1.5 HCl |
| 107 | B8-a* | H | CH₃ | CH₃O | 2-methyl-5-(aminomethyl)phenyl | H | |
| 108 | B6 | H | CH₃ | CH₃O | C(=O)—O—C(CH₃)₂ | H | |
| 109 | B6 | H | CH₃ | CH₃O | CH₂—CF₃ | H | |
| 110 | B6 | H | CH₃ | CH₃O | CHOH—CF₃ | H | |

TABLE 1-continued

| Co. No. | Pr. | R⁰ | R¹ | R² | R³ | R⁴ | salt form |
|---|---|---|---|---|---|---|---|
| 111 | B8-b* | H | CH₃ | CH₃O | 4-methyl-3-(propanamidomethyl)phenyl | H | |
| 112 | B6 | H | CH₃ | F | 4-fluorophenyl | O—CH₃ | |
| 113 | B6 | H | CH₃ | CH₃O | C(=O)—O—CH₂—CH₃ | H | |
| 114 | B8-c* | H | CH₃ | CH₃O | 4-methyl-3-(2-(2-(2-methoxyethoxy)ethoxy)acetamidomethyl)phenyl | H | •3H₂O •1.7HCl |
| 115 | B6 | H | CH₃ | F | (tetrahydro-2H-pyran-4-yl)methyl | H | •0.25H₂O •1.7HCl |
| 116 | B6 | H | CH₃ | CH₃O | cyclopropyl | H | |
| 117 | B9* | H | CH₃ | CH₃O | C(=O)—CH₂—CH₃ | H | •H₂O •3HCl |
| 118 | B6 | H | CH₃ | F | tetrahydro-2H-pyran-4-yl | H | •0.4H₂O •1HCl |
| 119 | B6 | H | CH₃ | F | CH₃ | H | |
| 120 | B6 | H | CH₃ | F | cyclopropyl | H | |
| 121 | B6 | H | CH₃ | CH₃O | C(OH)(CH₃)₂ | H | |
| 122 | B1-e* | H | CH₃ | CH₃O | 4-fluorophenyl | CH₂—NH₂ | |
| 123 | B6 | H | CH₃ | CH₃O | C(=O)—N(CH₃)₂ | H | |

TABLE 2
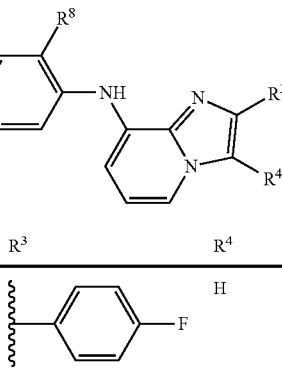
| Co. no. | Pr. | R⁰ | R¹ | R² | R⁸ | R³ | R⁴ | salt form |
|---|---|---|---|---|---|---|---|---|
| 6 | B5* | H | CH₃ | CH₃O | H | 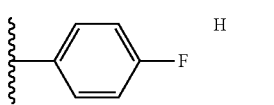 4-F-C₆H₄ | H | |
| 45 | B5 | CH₃ | H | CH₃O | H | 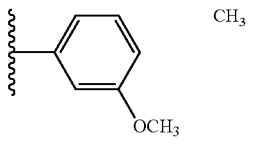 4-F-C₆H₄ | H | |
| 7 | B6* | H | H | CH₃O | H | 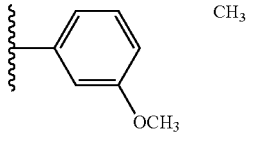 3-OCH₃-C₆H₄ | CH₃ | |
| 67 | B6 | H | CH₃ | CH₃O | H | 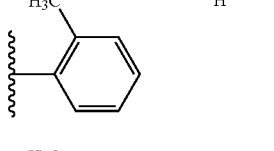 3-OCH₃-C₆H₄ | CH₃ | |
| 70 | B6 | H | CH₃ | CH₃O | H | 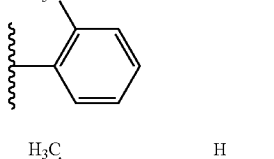 2-CH₃-C₆H₄ | H | |
| 71 | B6 | H | CH₃ | H | H | 2-CH₃-C₆H₄ | H | |
| 72 | B6 | H | CH₃ | CH₃O | H | 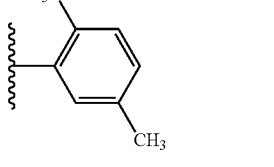 2,5-(CH₃)₂-C₆H₃ | H | |
| 73 | B6 | H | CH₃ | H | H | 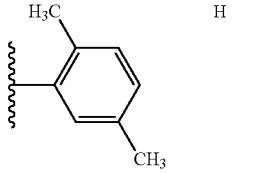 2,5-(CH₃)₂-C₆H₃ | H | |
| 74 | B6 | H | CH₃ | F | H | 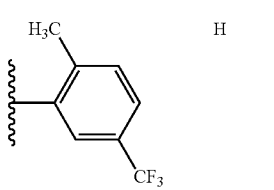 2-CH₃-5-CF₃-C₆H₃ | H | |

TABLE 2-continued

| Co. no. | Pr. | R⁰ | R¹ | R² | R⁸ | R³ | R⁴ | salt form |
|---|---|---|---|---|---|---|---|---|
| 75 | B6 | CH₃ | H | H | H | 2-methyl-5-trifluoromethyl-phenyl | H | |
| 76 | B6 | H | CH₃ | H | H | (CH₂)₃—CH₃ | H | •2HCl |
| 77 | B6 | H | CH₃ | CH₃O | H | CH₃ | H | |
| 78 | B6 | H | CH₃ | H | H | CH₃ | H | |
| 79 | B6 | H | CH₃ | H | H | CH₃ | CH₃ | |
| 80 | B6 | H | H | CH₃O | H | CH₃ | H | |
| 89 | B6 | H | CH₃ | CH₃O | H | 2-methyl-5-fluoro-phenyl | H | |
| 90 | B6 | H | CH₃ | H | H | 2-methyl-5-fluoro-phenyl | H | |
| 91 | B6 | H | CH₃ | F | H | 2-methyl-5-fluoro-phenyl | H | |
| 92 | B6 | H | CH₃ | CH₃O | H | 2-methyl-5-methoxy-phenyl | H | |
| 93 | B6 | H | CH₃ | H | H | 2-methyl-5-methoxy-phenyl | H | |
| 94 | B6 | H | CH₃ | F | H | 2-methyl-5-methoxy-phenyl | H | |

TABLE 2-continued

| Co. no. | Pr. | R⁰ | R¹ | R² | R⁸ | R³ | R⁴ | salt form |
|---|---|---|---|---|---|---|---|---|
| 124 | B6 | H | CH₃ | CH₃O | H | 2-Cl-phenyl | CH₃ | |
| 125 | B6 | H | CH₃ | CH₃O | H | 4-F-phenyl | CH₂—O—CH₃ | |
| 126 | B6 | H | CH₃ | CH₃O | H | 2-Cl-phenyl | CH₂—N(CH₃)₂ | |
| 127 | B10* | H | CH₃ | CH₃O | H | 4-F-phenyl | (CH₂)₂—O—CH₃ | |
| 128 | B6 | H | CH₃ | CH₃O | H | phenyl | CH₂—N(CH₃)₂ | |
| 129 | B10 | H | CH₃ | CH₃O | H | 4-F-phenyl | (CH₂)₃—O—CH₃ | •1HCl |
| 130 | B6 | CH₃ | H | F | H | 2-CH₃-5-CF₃-phenyl | H | |
| 131 | B6 | CH₃ | H | F | H | 2-CH₃-4-F-phenyl | H | |
| 132 | B6 | H | CH₃ | CH₃O | H | 4-F-phenyl | CH₃O | |

TABLE 2-continued
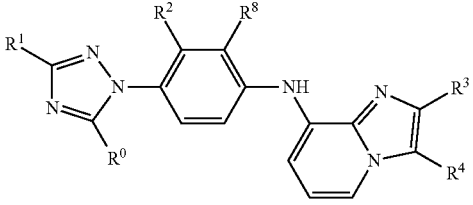
| Co. no. | Pr. | R⁰ | R¹ | R² | R⁸ | R³ | R⁴ | salt form |
|---|---|---|---|---|---|---|---|---|
| 133 | B6 | H | CH₃ | H | F | 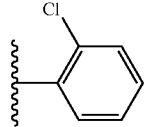 [SMILES: *c1ccccc1Cl] | CH₃ | |
| 134 | B6 | H | CH₃ | CH₃O | H | 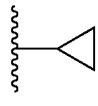 [SMILES: *C1CC1] | H | |
| 135 | B6 | H | CH₃ | CH₃O | H | 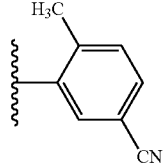 [SMILES: *c1cc(C#N)ccc1C] | H | |
| 136 | B6 | H | CH₃ | CH₃O | H | 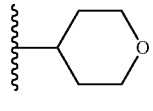 | H | •1.5H₂O •1.8HCl |
| 137 | B6 | H | CH₃ | CH₃O | H | 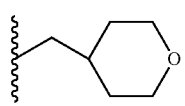 | H | •2.1H₂O •1.8HCl |

TABLE 3

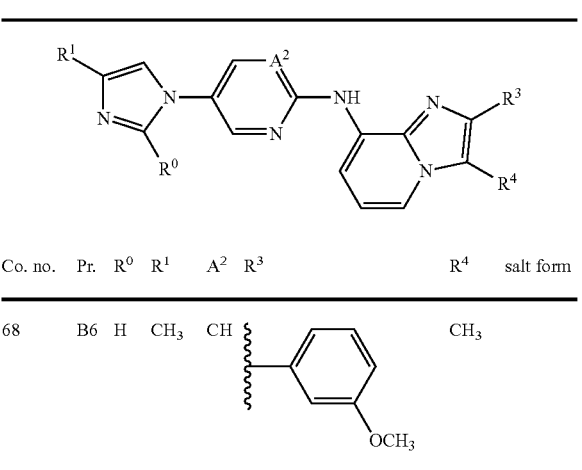

| Co. no. | Pr. | R⁰ | R¹ | A² | R³ | R⁴ | salt form |
|---|---|---|---|---|---|---|---|
| 68 | B6 | H | CH₃ | CH | 3-OCH₃-phenyl | CH₃ | |

TABLE 4

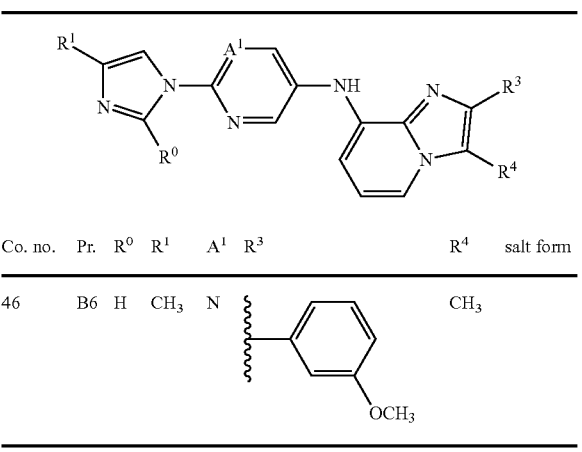

| Co. no. | Pr. | R⁰ | R¹ | A¹ | R³ | R⁴ | salt form |
|---|---|---|---|---|---|---|---|
| 46 | B6 | H | CH₃ | N | 3-OCH₃-phenyl | CH₃ | |

TABLE 5

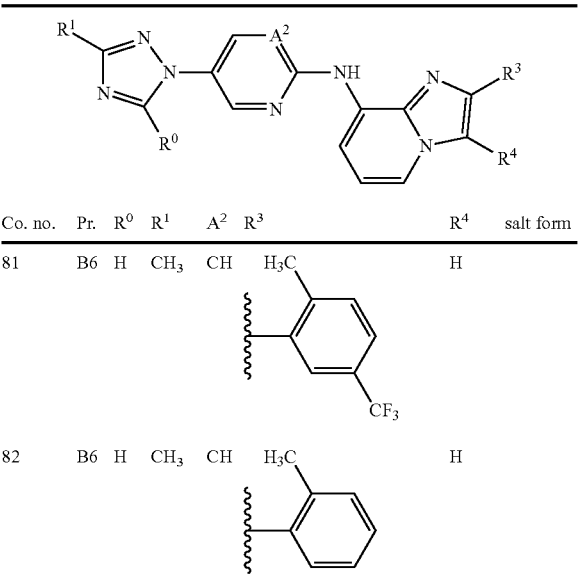

| Co. no. | Pr. | R⁰ | R¹ | A² | R³ | R⁴ | salt form |
|---|---|---|---|---|---|---|---|
| 81 | B6 | H | CH₃ | CH | H₃C- (2-methyl-4-CF₃-phenyl) | H | |
| 82 | B6 | H | CH₃ | CH | H₃C- (2-methylphenyl) | H | |

TABLE 5-continued

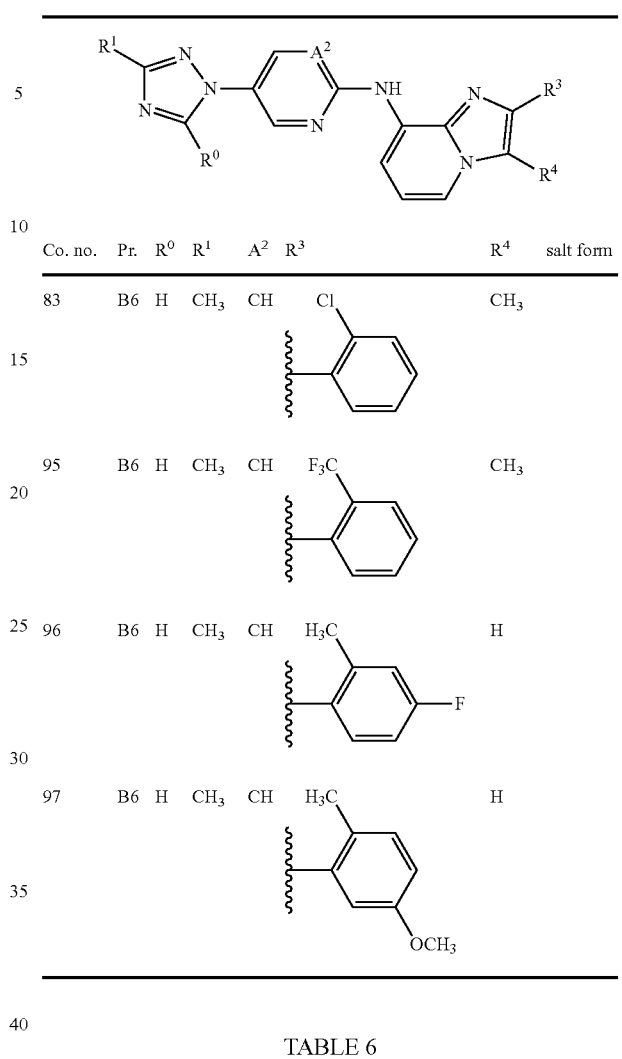

| Co. no. | Pr. | R⁰ | R¹ | A² | R³ | R⁴ | salt form |
|---|---|---|---|---|---|---|---|
| 83 | B6 | H | CH₃ | CH | Cl- (2-chlorophenyl) | CH₃ | |
| 95 | B6 | H | CH₃ | CH | F₃C- (2-CF₃-phenyl) | CH₃ | |
| 96 | B6 | H | CH₃ | CH | H₃C- (2-methyl-4-F-phenyl) | H | |
| 97 | B6 | H | CH₃ | CH | H₃C- (2-methyl-4-OCH₃-phenyl) | H | |

TABLE 6

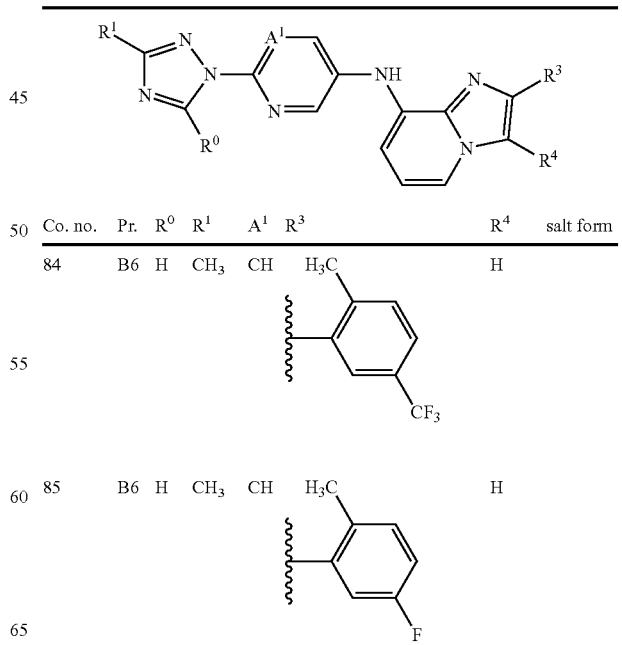

| Co. no. | Pr. | R⁰ | R¹ | A¹ | R³ | R⁴ | salt form |
|---|---|---|---|---|---|---|---|
| 84 | B6 | H | CH₃ | CH | H₃C- (2-methyl-4-CF₃-phenyl) | H | |
| 85 | B6 | H | CH₃ | CH | H₃C- (2-methyl-4-F-phenyl) | H | |

TABLE 6-continued

Structure: R¹-triazole(R⁰)-A¹-pyridine-NH-imidazopyridine(R³,R⁴)

| Co. no. | Pr. | R⁰ | R¹ | A¹ | R³ | R⁴ | salt form |
|---|---|---|---|---|---|---|---|
| 86 | B6 | H | CH₃ | CH | 2-methylphenyl (H₃C-) | H | |
| 87 | B6 | H | CH₃ | CH | 2-chlorophenyl (Cl-) | CH₃ | |
| 98 | B6 | H | CH₃ | CH | 2-methyl-4-fluorophenyl | H | |
| 99 | B6 | H | CH₃ | CH | 2-methyl-5-methoxyphenyl | H | |

TABLE 7

Structure: CH₃-triazole(X)-pyridine(OCH₃)-NH-imidazopyridine(R⁹,R³,R⁴)

| Co. No. | Pr. | X | R⁹ | R³ | R⁴ | salt form |
|---|---|---|---|---|---|---|
| 179 | B17.b* | CH | H | CH₂—CF₃ | H | |
| 182 | B17.a* | CH | H | CHCl—CF₃ | H | |
| 138 | B16 | CH | H | 2-(trifluoromethyl)phenyl | CH₃ | |

TABLE 7-continued

| Co. No. | Pr. | X | R⁹ | R³ | R⁴ | salt form |
|---|---|---|---|---|---|---|
| 139 | B16 | CH | H | 2-chlorophenyl | CH₃ | |
| 140 | B16 | CH | H | 2-chlorophenyl | CH₂—O—CH₃ | |
| 141 | B16 | CH | H | 4-fluorophenyl | O—CH₃ | |
| 142 | B16 | CH | F | CH₂—CH(CH₃)₂ | H | |
| 143 | B16 | CH | H | tetrahydropyran-4-yl | H | |
| 144 | B16 | CH | H | CH₃ | H | |
| 180 | B17 | N | H | CH₂—CF₃ | H | |
| 145 | B16* | N | H | 2-chlorophenyl | CH₃ | |

TABLE 8

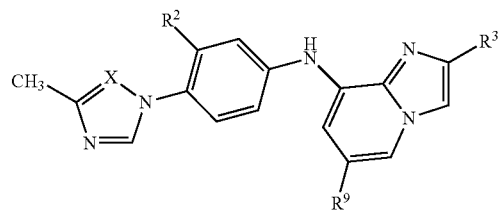

| Co. No. | Pr | X | R² | R⁹ | R³ | salt form |
|---|---|---|---|---|---|---|
| 146 | B6 | N | CH₃O | CF₃ | 4-fluorobenzyl | |
| 147 | B11.c* | N | CH₃O | CF₃ | (4-fluorophenoxy)methyl | |
| 148 | B6 | CH | F | F | 2-methyl-4-fluorophenyl | |
| 149 | B6 | CH | F | F | tetrahydropyran-4-yl | •0.9H₂O•1.8HCl |
| 150 | B6 | CH | F | Cl | tetrahydropyran-4-yl | |
| 151 | B9 | CH | CH₃O | CF₃ | C(OH)(CH₃)₂ | |
| 152 | B11.b* | N | CH₃O | CF₃ | CH₂—OH | |
| 153 | B12.b* | N | CH₃O | CF₃ | CH₂—CH₃ | |
| 154 | B12.a* | N | CH₃O | CF₃ | CH=CH₂ | |
| 155 | B6 | CH | CH₃O | CF₃ | C(O)—O—CH₂CH₃ | •1 HCl |
| 181 | B11.a* | N | CH₃O | CF₃ | C(O)—O—CH₂CH₃ | |
| 156 | B6 | CH | CH₃O | CF₃ | COOH | |

TABLE 9

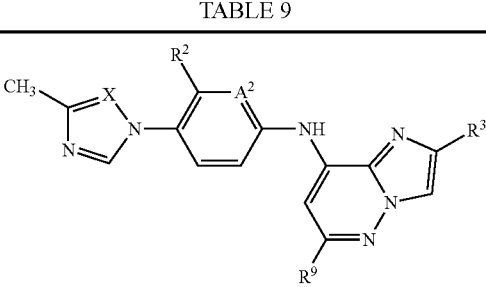

| Co. No. | Pr. | X | R² | A² | R⁹ | R³ | salt form |
|---|---|---|---|---|---|---|---|
| 157 | B6 | CH | CH₃O | CH | Cl |  | |

TABLE 9-continued
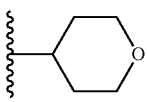
| Co. No. | Pr. | X | R² | A² | R⁹ | R³ | salt form |
|---|---|---|---|---|---|---|---|
| 158 | B6 | CH | CH₃O | CH | CF₃ | 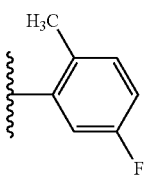 | |
| 159 | B13* | CH | CH₃O | CH | H | 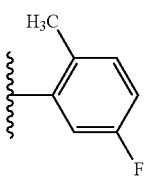 [SMILES: *c1cc(F)ccc1C] | |
| 160 | B14.c | CH | CH₃O | CH | CH(CH₃)₂ | CH₃ | |
| 161 | B14.b | CH | CH₃O | CH | 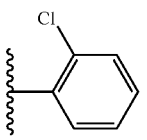 [SMILES: *c1ccccc1Cl] | CH₃ | |
| 162 | B6 | N | CH₃O | CH | Cl | 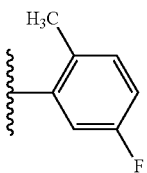 | |
| 163 | B14.c* | CH | CH₃O | N | CH(CH₃)₂ | 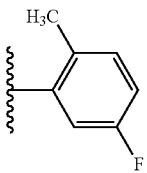 | |
| 164 | B6 | CH | CH₃O | CH | CF₃ | CH₃ | |
| 165 | B6 | CH | CH₃O | CH | Cl | CH₃ | |
| 166 | B13 | CH | F | CH | H | 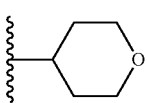 | |
| 167 | B13 | N | CH₃O | CH | H | 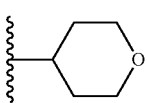 | |
| 168 | B6 | CH | F | CH | CF₃ | 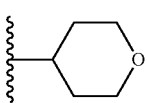 | |

TABLE 9-continued
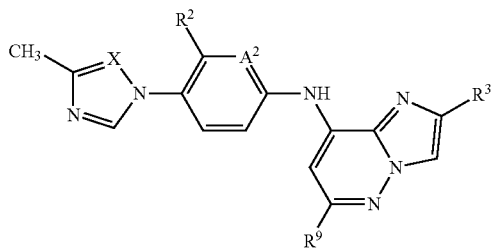
| Co. No. | Pr. | X | R² | A² | R⁹ | R³ | salt form |
|---|---|---|---|---|---|---|---|
| 169 | B6 | CH | F | CH | Cl | 2-methyl-4-fluorophenyl | |
| 170 | B14.c | CH | CH₃O | CH | tetrahydropyran-4-yl | CH₃ | |
| 171 | B14.b* | CH | CH₃O | N | isopropenyl (CH₂=C(CH₃)–) | 2-chlorophenyl | |
| 172 | B13 | CH | CH₃O | CH | H | CH₃ | |
| 173 | B6 | CH | F | CH | CF₃ | CH₃ | |
| 174 | B14.a* | CH | CH₃O | N | Cl | 2-chlorophenyl | |
TABLE 10
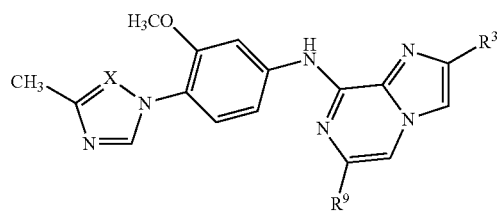
| Co. No. | Pr. | X | R⁹ | R³ | salt form |
|---|---|---|---|---|---|
| 175 | B6 | CH | H | 4-fluorophenyl | |
| 176 | B15.b* | N | H | 2-methyl-4-fluorophenyl | |
| 177 | B15.a* | N | Br | 2-methyl-4-fluorophenyl | |
| 178 | B6 | N | H | 4-fluorophenyl | |

Analytical Part
LCMS
General Procedure A

The LC measurement was performed using an Acquity UPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

General Procedure B

The HPLC measurement was performed using an Agilent 1100 series liquid chromatography system comprising a binary pump with degasser, an autosampler, a column oven, a UV detector and a column as specified in the respective methods below. Flow from the column was split to a MS spectrometer. The MS detector was configured with an electrospray ionization source. The capillary voltage was 3 kV, the quadrupole temperature was maintained at 100° C. and the desolvation temperature was 300° C. Nitrogen was used as the nebulizer gas. Data acquisition was performed with an Agilent Chemstation data system.

General Procedure C

The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

General Procedure D

The HPLC measurement was performed using a HP 1100 from Agilent Technologies comprising a pump (quaternary or binary) with degasser, an autosampler, a column oven, a diode-array detector (DAD) and a column as specified in the respective methods below. Flow from the column was split to a MS spectrometer. The MS detector was configured with an electrospray ionization source. Nitrogen was used as the nebulizer gas. The source temperature was maintained at 140° C. Data acquisition was performed with MassLynx-Openlynx software.

LCMS Method 1

In addition to general procedure A: Reversed phase UPLC (Ultra Performance Liquid Chromatography) was carried out on a bridged ethylsiloxane/silica hybrid (BEH) C18 column (1.7 µm, 2.1×50 mm; Waters Acquity) with a flow rate of 0.8 ml/min. Two mobile phases (25 mM ammoniumacetate ($NH_4OAc$) in $H_2O/CH_3CN$ 95/5; mobile phase B: $CH_3CN$) were used to run a gradient condition from 95% A and 5% B to 5% A and 95% B in 1.3 minutes (min) and hold for 0.3 min. An injection volume of 0.5 µl was used. Cone voltage was 10 V for positive ionization mode and 20 V for negative ionization mode.

LCMS Method 2

In addition to general procedure A: Reversed phase (RP) UPLC was carried out on a BEH C18 column (1.7 µm, 2.1×50 mm; Waters Acquity) with a flow rate of 0.8 ml/min. 2 Mobile phases (mobile phase A: 0.1% formic acid in $H_2O/MeOH$ 95/5; mobile phase B: MeOH) were used to run a gradient condition from 95% A and 5% B to 5% A and 95% B in 1.3 min and hold for 0.2 min. An injection volume of 0.5 µl was used. Cone voltage was 10 V for positive ionization mode and 20 V for negative ionization mode.

LCMS Method 3

In addition to general procedure B: RP HPLC was carried out on a YMC-Pack ODS-AQ C18 column (4.6×50 mm) with a flow rate of 2.6 ml/min. A gradient run was used from 95% water and 5% $CH_3CN$ to 95% $CH_3CN$ in 4.80 min and was hold for 1.20 min. Mass spectra were acquired by scanning from 100 to 1400. Injection volume was 10 µl. Column temperature was 35° C.

LCMS Method 4

In addition to general procedure C: Column heater was set at 60° C. RP HPLC was carried out on an Xterra MS C18 column (3.5 µm, 4.6×100 mm) with a flow rate of 1.6 ml/min. 3 Mobile phases (mobile phase A: 95% 25 mM $NH_4OAc$+5% $CH_3CN$; mobile phase B: $CH_3CN$; mobile phase C: MeOH) were employed to run a gradient condition from 100% A to 50% B and 50% C in 6.5 min, to 100% B in 0.5 min and hold these conditions for 1 min and reequilibrate with 100% A for 1.5 min. An injection volume of 10 µl was used. Cone voltage was 10 V for positive ionization mode and 20 V for negative ionization mode.

LCMS Method 5

In addition to general procedure C: Column heater was set at 45° C. RP HPLC was carried out on an Atlantis C18 column (3.5 µm, 4.6×100 mm) with a flow rate of 1.6 ml/min. 2 Mobile phases (mobile phase A: 70% MeOH+30% $H_2O$; mobile phase B: 0.1% formic acid in $H_2O/MeOH$ 95/5) were employed to run a gradient condition from 100% B to 5% B+95% A in 9 min and hold these conditions for 3 min. An injection volume of 10 µl was used. Cone voltage was 10 V for positive ionization mode and 20 V for negative ionization mode.

LCMS Method 6

In addition to general procedure C: RP HPLC was carried out on an Xterra MS C18 column (3.5 µm, 4.6×100 mm) with a flow rate of 1.6 ml/min. 3 Mobile phases (mobile phase A: 95% 25 mM $NH_4OAc$+5% $CH_3CN$; mobile phase B: $CH_3CN$; mobile phase C: MeOH) were employed to run a gradient condition from 100% A to 1% A, 49% B and 50% C in 6.5 min, to 1% A and 99% B in 1 min and hold these conditions for 1 min and reequilibrate with 100% A for 1.5 min. An injection volume of 10 µl was used. Cone voltage was 10 V for positive ionization mode and 20 V for negative ionization mode.

LCMS Method 7

In addition to general procedure D: RP HPLC was carried out on an XDB-C18 cartridge (1.8 µm, 2.1×30 mm) from Agilent, at 60° C. with a flow rate of 1 ml/min, at 60° C. The gradient conditions used are: 90% A (0.5 g/l $NH_4OAc$ solution), 5% B ($CH_3CN$), 5% C (MeOH) to 50% B and 50% C in 6.5 min, to 100% B at 7 min and equilibrated to initial conditions at 7.5 min until 9.0 min. Injection volume 2 µl. High-resolution mass spectra (Time of Flight, TOF) were acquired only in positive ionization mode by scanning from 100 to 750 in 0.5 seconds (sec) using a dwell time of 0.1 sec. The capillary needle voltage was 2.5 kV and the cone voltage was 20 V. Leucine-Enkephaline was the standard substance used for the lock mass calibration.

LCMS Method 8

In addition to general procedure A: RP HPLC was carried out on a BEH C18 column (1.7 μm, 2.1×50 mm; Waters Acquity) with a flow rate of 0.8 ml/min. 2 Mobile phases (25 mM NH₄OAc in H₂O/CH₃CN 95/5; mobile phase B: CH₃CN) were used to run a gradient condition from 95% A and 5% B to 5% A and 95% B in 1.3 min and hold for 0.3 min. An injection volume of 0.5 μl was used. Cone voltage was 30 V for positive ionization mode and 30 V for negative ionization mode.

Melting Points

For a number of compounds (indicated with 'DSC'), melting points (m.p.) were determined with a DSC823e (Mettler-Toledo). Melting points were measured with a temperature gradient of 30° C./minute. Maximum temperature was 400° C. Values are peak values.

For a number of compounds (indicated with 'M'), melting points were determined in open capillary tubes on a Mettler FP62 apparatus. Melting points were measured with a temperature gradient of 3 or 10° C./minute. Maximum temperature was 300° C. The melting point was read from a digital display.

The results of the analytical measurements are shown in table 11.

TABLE 11

Retention time ($R_t$) in min., $[M + H]^+$ peak (protonated molecule), LCMS method and m.p. (melting point in ° C.). (n.d. means not determined; dec. means decomposition)

| Co. No. | $R_t$ | $[M + H]^+$ | LCMS Method | m.p. (° C.) |
|---|---|---|---|---|
| 1 | 1.09 | 414 | 1 | 209.2 DSC |
| 2 | 6.96 | 448 | 6 | 168.9 DSC |
| 3 | 1.05 | 428 | 1 | n.d. |
| 4 | 1.3 | 404 | 3 | n.d. |
| 5 | 5.45 | 410 | 5 | 177.8 DSC |
| 6 | 1.06 | 415 | 1 | n.d. |
| 7 | 1.06 | 427 | 1 | n.d. |
| 8 | 4.79 | 414 | 7 | dec. M |
| 9 | 1.453 | 376 | 3 | n.d. |
| 10 | 1.14 | 390 | 1 | n.d. |
| 11 | 5.71 | 418 | 5 | n.d. |
| 12 | 1.91 | 396 | 3 | n.d. |
| 13 | 2.65 | 472 | 3 | n.d. |
| 14 | 2.32 | 430 | 3 | n.d. |
| 15 | 1.14 | 444 | 1 | 204.0 DSC |
| 16 | 2.465 | 430 | 3 | n.d. |
| 17 | 2.40 | 430 | 3 | n.d. |
| 18 | 5.93 | 428 | 5 | n.d. |
| 19 | 2.27 | 414 | 3 | n.d. |
| 20 | 6.44 | 428 | 5 | n.d. |
| 21 | 1.02 | 414 | 1 | n.d. |
| 22 | 1.26 | 492 | 1 | n.d. |
| 23 | 1.01 | 442 | 2 | n.d. |
| 24 | 1.24 | 456 | 1 | n.d. |
| 25 | 2.48 | 432 | 3 | n.d. |
| 26 | 6.28 | 446 | 5 | n.d. |
| 27 | 0.97 | 446 | 2 | 198.2 DSC |
| 28 | 2.06 | 444 | 3 | n.d. |
| 29 | 1.15 | 478 | 1 | n.d. |
| 30 | 2.60 | 464 | 3 | n.d. |
| 31 | 6.50 | 421 | 5 | 193.4 DSC |
| 32 | 1.09 | 426 | 1 | n.d. |
| 33 | 2.02 | 426 | 3 | n.d. |
| 34 | 1.11 | 440 | 1 | n.d. |
| 35 | 1.08 | 426 | 1 | 124.2 DSC |
| 36 | 1.86 | 426 | 3 | n.d. |
| 37 | 6.05 | 456 | 4 | n.d. |
| 38 | 1.35 | 466 | 1 | 224.6 DSC |
| 39 | 1.22 | 467 | 1 | n.d. |
| 40 | 1.81 | 481 | 3 | n.d. |
| 41 | 1.62 | 397 | 3 | n.d. |
| 42 | 1.61 | 397 | 3 | n.d. |
| 43 | 1.48 | 397 | 3 | n.d. |
| 44 | 1.55 | 450 | 3 | n.d. |
| 45 | 1.00 | 415 | 1 | n.d. |
| 46 | 1.04 | 412 | 1 | n.d. |
| 47 | 2.38 | 464 | 3 | n.d. |
| 48 | 2.69 | 464 | 3 | n.d. |
| 49 | 1.03 | 320 | 3 | n.d. |
| 50 | 1.12 | 334 | 3 | n.d. |
| 51 | 1.52 | 376 | 3 | n.d. |
| 52 | 2.01 | 428 | 3 | n.d. |
| 53 | 3.43 | 450 | 3 | n.d. |
| 54 | 1.44 | 392 | 3 | n.d. |
| 55 | 1.39 | 417 | 3 | n.d. |
| 56 | 1.29 | 419 | 3 | n.d. |
| 57 | 7.93 | 540 | 5 | n.d. |
| 58 | 7.32 | 439 | 5 | n.d. |
| 59 | 1.96 | 404 | 3 | n.d. |
| 60 | 2.49 | 472 | 3 | n.d. |
| 61 | 2.57 | 472 | 3 | n.d. |
| 62 | 2.60 | 442 | 3 | n.d. |
| 63 | 1.17 | 454 | 1 | 159.9 DSC |
| 64 | 0.89 | 410 | 2 | n.d. |
| 65 | 0.89 | 410 | 2 | n.d. |
| 66 | 1.13 | 428 | 1 | n.d. |
| 67 | 1.08 | 441 | 1 | n.d. |
| 68 | 1.08 | 411 | 1 | 183.2 DSC |
| 69 | 1.50 | 376 | 3 | n.d. |
| 70 | 7.20 | 411 | 5 | n.d. |
| 71 | 7.05 | 381 | 5 | n.d. |
| 73 | 9.06 | 449 | 5 | n.d. |
| 74 | 9.10 | 467 | 5 | n.d. |
| 75 | 8.71 | 449 | 5 | n.d. |
| 76 | 1.05 | 347 | 1 | n.d. |
| 77 | 0.84 | 335 | 1 | n.d. |
| 78 | 0.81 | 305 | 1 | 213.1 DSC |
| 79 | 0.87 | 319 | 1 | 230.6 DSC |
| 80 | 0.80 | 321 | 1 | 147.5 DSC |
| 81 | 1.46 | 450 | 2 | n.d. |
| 82 | 1.07 | 382 | 1 | n.d. |
| 83 | 1.11 | 416 | 1 | 209.7 DSC |
| 84 | 9.17 | 450 | 5 | n.d. |
| 86 | 1.07 | 382 | 1 | 165.7 DSC |
| 87 | 1.30 | 416 | 2 | 232.0 DSC |
| 88 | 2.32 | 414 | 3 | n.d. |
| 89 | 6.26 | 429 | 4 | n.d. |
| 90 | 1.11 | 399 | 1 | n.d. |
| 91 | 7.82 | 417 | 5 | n.d. |
| 94 | 1.12 | 429 | 1 | n.d. |
| 98 | 7.78 | 400 | 5 | n.d. |
| 101 | 0.91 | 444 | 2 | n.d. |
| 102 | 5.85 | 503 | 6 | n.d. |
| 103 | 1.30 | 462 | 2 | n.d. |
| 104 | 1.21 | 428 | 2 | n.d. |
| 105 | 1.10 | 435 | 8 | 127.5 DSC |
| 106 | n.d. | n.d. | n.d. | 203.4 DSC |

TABLE 11-continued

Retention time ($R_t$) in min., [M + H]⁺ peak (protonated molecule), LCMS method and m.p. (melting point in ° C.). (n.d. means not determined; dec. means decomposition)

| Co. No. | $R_t$ | [M + H]⁺ | LCMS Method | m.p. (° C.) |
|---|---|---|---|---|
| 107 | 0.80 | 439 | 8 | n.d. |
| 108 | 0.96 | 406 | 8 | 235.3 DSC |
| 109 | 0.97 | 402 | 8 | n.d. |
| 110 | 5.38 | 418 | 6 | n.d. |
| 111 | 0.97 | 495 | 8 | n.d. |
| 112 | 1.16 | 432 | 8 | 163.3 DSC |
| 113 | 0.89 | 392 | 8 | 203.5 DSC |
| 114 | 0.98 | 599 | 8 | n.d. |
| 115 | 5.72 | 406 | 6 | n.d. |
| 116 | 0.97 | 360 | 8 | n.d. |
| 117 | 0.88 | 376 | 8 | n.d. |
| 118 | 5.60 | 392 | 6 | n.d. |
| 119 | 0.87 | 322 | 8 | n.d. |
| 120 | 0.58 | 348 | 2 | n.d. |
| 121 | 0.80 | 378 | 8 | 180.4 DSC |
| 123 | n.d. | n.d. | n.d. | 196.2 DSC |
| 124 | 1.13 | 445 | 8 | n.d. |
| 125 | 1.07 | 459 | 8 | 173.0 DSC |
| 126 | 1.08 | 488 | 2 | n.d. |
| 127 | 1.11 | 473 | 8 | 149.5 DSC |
| 128 | 1.12 | 454 | 8 | n.d. |
| 129 | 1.15 | 487 | 8 | n.d. |
| 130 | 8.77 | 467 | 5 | 210.0 DSC |
| 131 | 7.22 | 417 | 5 | n.d. |
| 132 | n.d. | n.d. | n.d. | 165.1 DSC |
| 133 | 1.16 | 433 | 8 | n.d. |
| 134 | 0.84 | 360 | 2 | n.d. |
| 135 | 3.07 | 436 | 3 | n.d. |
| 137 | 0.87 | 419 | 8 | n.d. |
| 138 | 1.20 | 479 | 8 | 151.5 DSC |
| 139 | 1.29 | 445 | 8 | n.d. |
| 140 | 1.36 | 475 | 2 | 163.5 DSC |
| 141 | 1.20 | 445 | 8 | n.d. |
| 142 | 1.19 | 395 | 8 | 187.9 DSC |
| 144 | 0.90 | 335 | 8 | n.d. |
| 145 | 6.65 | 446 | 6 | 250.3 DSC |
| 146 | 3.69 | 497 | 3 | n.d. |
| 147 | 3.82 | 513 | 3 | n.d. |
| 149 | 0.94 | 410 | 8 | n.d. |
| 150 | 1.01 | 426 | 8 | 169.9 DSC |
| 151 | 5.78 | 446 | 6 | 215.7 DSC |
| 152 | 2.49 | 419 | 3 | n.d. |
| 153 | 1.09 | 417 | 8 | n.d. |
| 154 | 1.33 | 415 | 2 | n.d. |
| 155 | 6.92 | 460 | 5 | n.d. |
| 156 | 6.34 | 432 | 5 | n.d. |
| 157 | 1.27 | 464 | 8 | n.d. |
| 158 | n.d. | n.d. | n.d. | 159.8 DSC |
| 159 | 1.14 | 429 | 8 | n.d. |
| 160 | 1.03 | 377 | 8 | n.d. |
| 161 | 1.05 | 441 | 8 | 82.9 DSC |
| 162 | 1.26 | 465 | 8 | n.d. |
| 163 | 1.43 | 474 | 8 | 179.3 DSC |
| 164 | 1.04 | 403 | 8 | 236.8 DSC |
| 165 | 0.97 | 369 | 8 | 225.9 DSC |
| 166 | 1.14 | 417 | 8 | n.d. |
| 167 | 1.11 | 430 | 8 | 242.6 DSC |
| 168 | 1.06 | 461 | 8 | n.d. |
| 169 | 1.27 | 452 | 8 | n.d. |
| 170 | 0.89 | 419 | 8 | n.d. |
| 171 | 1.47 | 472 | 8 | n.d. |
| 172 | 0.82 | 335 | 8 | n.d. |
| 173 | 1.04 | 391 | 8 | 221.0 DSC |
| 174 | 1.37 | 467 | 8 | 226.6 DSC |
| 175 | 1.19 | 415 | 2 | 177.7 DSC |
| 176 | 1.37 | 430 | 2 | n.d. |
| 177 | 1.48 | 509 | 2 | n.d. |
| 178 | 1.03 | 416 | 8 | 224.1 DSC |
| 179 | 1.00 | 403 | 8 | n.d. |
| 180 | 1.19 | 404 | 2 | n.d. |
| 182 | 1.17 | 437 | 8 | n.d. |

For Co. No. 100 the [M − H]⁻ peak was detected: Rt 6.04; [M − H]⁻ 469; LCMS Method 5.
For Co. No. 122 the [M − H]⁻ peak was detected: Rt 5.03; [M − H]⁻ 441; LCMS Method 5.

NMR

For a number of compounds, ¹H NMR spectra were recorded on a Bruker DPX-360, on a Bruker DPX-400, on a Bruker Avance 500 spectrometer or on a Bruker Avance 600 spectrometer with standard pulse sequences, operating at 360, 400, 500 and 600 MHz respectively, using CHLOROFORM-d (deuterated chloroform, $CDCl_3$) or DMSO-$d_6$ (deuterated DMSO, dimethyl-d6 sulfoxide) as solvents. Chemical shifts (δ) are reported in parts per million (ppm) relative to tetramethylsilane (TMS), which was used as internal standard.

Compound 1: ¹H NMR (500 MHz, $CDCl_3$) δ ppm 2.31 (s, 3 H), 3.85 (s, 3 H), 6.71 (t, J=7.1 Hz, 1 H), 6.90 (s, 1 H), 6.93 (d, J=7.5 Hz, 1 H), 6.95 (d, J=2.3 Hz, 1 H), 7.00 (dd, J=8.4, 2.3 Hz, 1 H), 7.15 (t, J=8.6 Hz, 2 H), 7.22 (d, J=8.4 Hz, 1 H), 7.33 (s, 1 H), 7.65 (d, J=1.3 Hz, 1 H), 7.70 (d, J=6.6 Hz, 1 H), 7.80 (s, 1 H), 7.94 (dd, J=8.5, 5.5 Hz, 2 H).

Compound 2: ¹H NMR (360 MHz, DMSO-$d_6$) δ ppm 2.16 (s, 3 H), 3.81 (s, 3 H), 7.02 (t, J=7.2 Hz, 1 H), 7.05-7.09 (m, 2 H), 7.15 (d, J=7.6 Hz, 1 H), 7.26 (d, J=2.2 Hz, 1 H), 7.29 (d, J=8.5 Hz, 1 H), 7.39 (t, J=8.8 Hz, 2 H), 7.69 (d, J=1.3 Hz, 1 H), 7.92 (d, J=6.6 Hz, 1 H), 8.18 (dd, J=8.7, 5.6 Hz, 2 H), 8.66 (s, 1 H).

Compound 3: ¹H NMR (360 MHz, DMSO-$d_6$) δ ppm 2.35 (s, 3 H), 3.83 (s, 3 H), 4.24 (s, 2 H), 7.02 (dd, J=8.6, 2.2 Hz, 1 H), 7.17 (d, J=2.2 Hz, 1 H), 7.20 (t, J=8.8 Hz, 2 H), 7.31 (t, J=7.3 Hz, 1 H), 7.50 (dd, J=8.4, 5.5 Hz, 2 H), 7.53 (d, J=8.6 Hz, 1 H), 7.64 (d, J=8.0 Hz, 1 H), 7.67 (s, 1 H), 8.09 (s, 1 H), 8.41 (d, J=6.5 Hz, 1 H), 9.32 (d, J=1.6 Hz, 1 H), 9.66 (br. s., 1 H), 15.14 (br. s., 1 H).

Compound 5: ¹H NMR (360 MHz, DMSO-$d_6$) δ ppm 2.15 (s, 3 H), 2.65 (s, 3 H), 3.80 (s, 3 H), 6.87 (t, J=7.1 Hz, 1 H), 7.00-7.08 (m, 3 H), 7.23-7.28 (m, 2 H), 7.36 (t, J=7.3 Hz, 1 H), 7.50 (t, J=7.6 Hz, 2 H), 7.67 (d, J=1.3 Hz, 1 H), 7.83-7.91 (m, 3 H), 8.46 (s, 1 H).

Compound 7: ¹H NMR (360 MHz, $CDCl_3$) δ ppm 2.65 (s, 3 H), 3.90 (s, 3 H), 3.91 (s, 3 H), 6.81 (t, J=7.1 Hz, 1 H), 6.93

(ddd, J=7.9, 2.7, 1.3 Hz, 1 H), 6.97 (d, J=2.3 Hz, 1 H), 6.99 (d, J=7.5 Hz, 1 H), 7.08 (dd, J=8.6, 2.3 Hz, 1 H), 7.36 (dt, J=7.5, 1.4 Hz, 1 H), 7.38-7.43 (m, 2 H), 7.50 (s, 1 H), 7.52 (d, J=6.7 Hz, 1 H), 7.67 (d, J=8.6 Hz, 1 H), 8.08 (s, 1 H), 8.65 (s, 1 H).

Compound 8: $^1$H NMR (500 MHz, CDCl$_3$) δ ppm 2.31 (s, 3 H), 3.85 (s, 3 H), 6.77 (t, J=7.2 Hz, 1 H), 6.89 (s, 1 H), 6.94 (d, J=2.3 Hz, 1 H), 6.98 (d, J=7.2 Hz, 1 H), 6.99 (dd, J=8.3, 2.5 Hz, 1 H), 7.20-7.26 (m, 3 H), 7.33 (s, 1 H), 7.56 (dd, J=8.4, 5.3 Hz, 2 H), 7.59 (s, 1 H), 7.65 (s, 1 H), 7.81 (d, J=6.8 Hz, 1 H).

Compound 10: $^1$H NMR (360 MHz, CDCl$_3$) δ ppm 1.01 (t, J=7.3 Hz, 3 H), 1.25 (t, J=7.5 Hz, 3 H), 1.72-1.84 (m, J=7.5, 7.5, 7.5, 7.5, 7.5 Hz, 2 H), 2.30 (s, 3 H), 2.69-2.76 (m, J=8.1, 7.3 Hz, 2 H), 2.90 (q, J=7.5 Hz, 2 H), 3.83 (s, 3 H), 6.70 (t, J=7.1 Hz, 1 H), 6.88 (s, 1 H), 6.89-6.93 (m, 2 H), 6.96 (dd, J=8.4, 2.2 Hz, 1 H), 7.19 (d, J=8.4 Hz, 1 H), 7.24 (s, 1 H), 7.48 (d, J=6.7 Hz, 1 H), 7.64 (s, 1 H).

Compound 11: $^1$H NMR (360 MHz, DMSO-d$_6$) δ ppm 0.92 (t, J=7.4 Hz, 3 H), 0.92 (t, J=7.3 Hz, 3 H), 1.30-1.42 (m, J=7.4, 7.4, 7.4, 7.4, 7.4 Hz, 2 H), 1.52-1.63 (m, J=7.4, 7.4, 7.4, 7.4, 7.4 Hz, 2 H), 1.63-1.72 (m, J=7.5, 7.5, 7.5, 7.5 Hz, 2 H), 2.15 (s, 3 H), 2.68 (t, J=7.6 Hz, 2 H), 2.86 (t, J=7.4 Hz, 2 H), 3.78 (s, 3 H), 6.75 (t, J=7.1 Hz, 1 H), 6.95 (d, J=7.4 Hz, 1 H), 6.99-7.05 (m, 2 H), 7.21-7.26 (m, 2 H), 7.66 (s, 1 H), 7.81 (d, J=6.7 Hz, 1 H), 8.33 (s, 1 H).

Compound 15: $^1$H NMR (360 MHz, DMSO-d$_6$) δ ppm 2.14 (s, 3 H), 2.38 (s, 3 H), 3.77 (s, 3 H), 6.90 (t, J=7.1 Hz, 1 H), 7.03-7.08 (m, 3 H), 7.22-7.27 (m, 2 H), 7.41-7.50 (m, 2 H), 7.54-7.63 (m, 2 H), 7.66 (s, 1 H), 7.86 (d, J=6.7 Hz, 1 H), 8.53 (s, 1 H).

Compound 18: $^1$H NMR (360 MHz, CDCl$_3$) δ ppm 2.27 (s, 3 H), 2.46 (d, J=2.3 Hz, 3 H), 3.79 (s, 3 H), 6.77 (t, J=7.1 Hz, 1 H), 6.85 (s, 1 H), 6.89 (d, J=2.3 Hz, 1 H), 6.92-6.97 (m, 2 H), 7.13-7.20 (m, 2 H), 7.25 (t, J=7.1 Hz, 1 H), 7.31 (s, 1 H), 7.32-7.39 (m, 1 H), 7.48 (d, J=6.7 Hz, 1 H), 7.60 (s, 1 H), 7.69 (td, J=7.5, 1.9 Hz, 1 H).

Compound 21: $^1$H NMR (360 MHz, DMSO-d$_6$) δ ppm 2.11 (s, 3 H), 3.77 (s, 3 H), 6.82 (t, J=7.1 Hz, 1 H), 6.86 (d, J=1.3 Hz, 1 H), 7.06 (dd, J=8.5, 2.2 Hz, 1 H), 7.06 (d, J=1.2 Hz, 1 H), 7.08 (s, 1 H), 7.20 (d, J=8.4 Hz, 1 H), 7.25 (d, J=2.3 Hz, 1 H), 7.30 (t, J=8.8 Hz, 2 H), 8.03-8.10 (m, 3 H), 8.40 (s, 1 H), 8.52 (s, 1 H).

Compound 22: $^1$H NMR (360 MHz, CDCl$_3$) δ ppm 2.31 (s, 3 H), 3.86 (s, 3 H), 6.88 (t, J=7.1 Hz, 1 H), 6.90 (s, 1 H), 6.94 (d, J=2.3 Hz, 1 H), 6.98-7.03 (m, 2 H), 7.20 (d, J=8.7 Hz, 2 H), 7.24 (d, J=8.4 Hz, 1 H), 7.29 (s, 1 H), 7.66 (d, J=1.3 Hz, 1 H), 7.75 (dd, J=6.8, 1.0 Hz, 1 H), 8.12 (dd, J=8.8, 5.4 Hz, 2 H).

Compound 23: $^1$H NMR (360 MHz, DMSO-d$_6$) δ ppm 1.28 (t, J=7.4 Hz, 3 H), 2.15 (s, 3 H), 3.10 (q, J=7.4 Hz, 2 H), 3.80 (s, 3 H), 6.86 (t, J=7.1 Hz, 1 H), 7.02-7.07 (m, 3 H), 7.24-7.28 (m, 2 H), 7.34 (t, J=8.8 Hz, 2 H), 7.67 (d, J=1.3 Hz, 1 H), 7.85 (dd, J=8.6, 5.6 Hz, 2 H), 7.94 (d, J=6.8 Hz, 1 H), 8.47 (s, 1 H).

Compound 24: $^1$H NMR (360 MHz, DMSO-d$_6$) δ ppm 0.97 (t, J=7.3 Hz, 3 H), 1.64-1.75 (m, J=7.5, 7.5, 7.5, 7.5, 7.5 Hz, 2 H), 2.36 (s, 3 H), 3.11 (t, J=7.8 Hz, 2 H), 3.86 (s, 3 H), 7.12 (dd, J=8.6, 2.2 Hz, 1 H), 7.24 (t, J=6.7 Hz, 1 H), 7.28 (d, J=2.2 Hz, 1 H), 7.45 (t, J=8.7 Hz, 2 H), 7.49-7.57 (m, 1 H), 7.54 (d, J=8.6 Hz, 1 H), 7.69 (s, 1 H), 7.91 (dd, J=8.6, 5.4 Hz, 2 H), 8.32 (d, J=6.7 Hz, 1 H), 9.33 (d, J=1.6 Hz, 1 H), 9.64 (br. s., 1 H), 15.12 (br. s., 1 H).

Compound 26: $^1$H NMR (360 MHz, DMSO-d$_6$) δ ppm 2.15 (s, 3 H), 2.44 (d, J=2.1 Hz, 3 H), 3.79 (s, 3 H), 6.90 (t, J=7.1 Hz, 1 H), 7.02-7.09 (m, 3 H), 7.22-7.28 (m, 3 H), 7.41 (td, J=10.0, 2.6 Hz, 1 H), 7.67 (s, 1 H), 7.74 (td, J=8.6, 6.7 Hz, 1 H), 7.87 (d, J=6.8 Hz, 1 H), 8.53 (s, 1 H).

Compound 27: $^1$H NMR (360 MHz, DMSO-d$_6$) δ ppm 2.15 (s, 3 H), 2.38 (s, 3 H), 3.78 (s, 3 H), 6.91 (t, J=7.1 Hz, 1 H), 7.01-7.10 (m, 3 H), 7.21-7.30 (m, 4 H), 7.57 (tt, J=8.4, 6.6 Hz, 1 H), 7.67 (s, 1 H), 7.88 (d, J=6.8 Hz, 1 H), 8.52 (s, 1 H).

Compound 29: $^1$H NMR (360 MHz, DMSO-d$_6$) δ ppm 2.36 (s, 3 H), 2.39 (s, 3 H), 3.84 (s, 3 H), 7.06 (dd, J=8.6, 2.2 Hz, 1 H), 7.22 (d, J=2.2 Hz, 1 H), 7.44 (t, J=7.6 Hz, 1 H), 7.54 (d, J=8.6 Hz, 1 H), 7.68 (s, 1 H), 7.69-7.75 (m, 2 H), 7.83-7.95 (m, 2 H), 8.02 (d, J=7.6 Hz, 1 H), 8.35 (d, J=6.6 Hz, 1 H), 9.34 (d, J=1.6 Hz, 1 H), 9.79 (br. s., 1 H), 15.15 (br. s., 1 H).

Compound 31: $^1$H NMR (360 MHz, DMSO-d$_6$) δ ppm 2.15 (s, 3 H), 3.81 (s, 3 H), 6.84 (t, J=7.1 Hz, 1 H), 7.03-7.08 (m, 3 H), 7.22-7.28 (m, 2 H), 7.68 (d, J=0.5 Hz, 1 H), 7.93 (d, J=8.3 Hz, 2 H), 8.08 (d, J=6.6 Hz, 1 H), 8.23 (d, J=8.3 Hz, 2 H), 8.52 (s, 1 H), 8.60 (s, 1 H).

Compound 32: $^1$H NMR (360 MHz, DMSO-d$_6$) δ ppm 2.15 (s, 3 H), 3.81 (s, 3 H), 3.99 (s, 3 H), 6.77 (t, J=7.1 Hz, 1 H), 7.01 (d, J=7.5 Hz, 1 H), 7.04-7.11 (m, 3 H), 7.15 (d, J=8.3 Hz, 1 H), 7.23-7.29 (m, 2 H), 7.29-7.36 (m, 1 H), 7.68 (d, J=1.3 Hz, 1 H), 8.11 (d, J=6.6 Hz, 1 H), 8.39 (s, 1 H), 8.43 (s, 1 H), 8.46 (dd, J=7.7, 1.8 Hz, 1 H).

Compound 34: $^1$H NMR (400 MHz, CDCl$_3$) δ ppm 2.31 (s, 3 H), 2.65 (s, 3 H), 3.84 (s, 3 H), 3.90 (s, 3 H), 6.79 (t, J=7.1 Hz, 1 H), 6.89 (s, 1 H), 6.91-6.97 (m, 3 H), 6.99 (dd, J=8.4, 2.3 Hz, 1 H), 7.21 (d, J=8.4 Hz, 1 H), 7.35-7.42 (m, 4 H), 7.50 (d, J=6.7 Hz, 1 H), 7.64 (d, J=1.3 Hz, 1 H).

Compound 35: $^1$H NMR (400 MHz, CDCl$_3$) δ ppm 2.65 (s, 3 H), 3.84 (s, 3 H), 3.90 (s, 3 H), 6.79 (t, J=7.1 Hz, 1 H), 6.93 (ddd, J=7.8, 2.7, 1.4 Hz, 1 H), 6.97 (d, J=7.2 Hz, 1 H), 6.96 (d, J=2.1 Hz, 1 H), 7.01 (dd, J=8.4, 2.3 Hz, 1 H), 7.16-7.18 (m, 2 H), 7.24 (d, J=8.4 Hz, 1 H), 7.35-7.43 (m, 4 H), 7.51 (d, J=6.7 Hz, 1 H), 7.75 (s, 1 H).

Compound 37: $^1$H NMR (360 MHz, DMSO-d$_6$) δ ppm 2.15 (s, 3 H), 3.80 (s, 3 H), 3.83 (s, 3 H), 3.97 (s, 3 H), 6.65-6.71 (m, 2 H), 6.75 (t, J=7.1 Hz, 1 H), 6.99 (d, J=7.5 Hz, 1 H), 7.03-7.08 (m, 2 H), 7.22-7.28 (m, 2 H), 7.68 (d, J=1.3 Hz, 1 H), 8.09 (d, J=6.6 Hz, 1 H), 8.26 (s, 1 H), 8.34 (d, J=8.2 Hz, 1 H), 8.39 (s, 1 H).

Compound 39: $^1$H NMR (360 MHz, DMSO-d$_6$) δ ppm 1.12 (t, J=7.0 Hz, 6 H), 2.15 (s, 3 H), 3.38 (q, J=7.3 Hz, 4 H), 3.80 (s, 3 H), 6.68-6.77 (m, 3 H), 6.98 (d, J=7.5 Hz, 1 H), 7.01-7.06 (m, 2 H), 7.22-7.28 (m, 2 H), 7.67 (d, J=1.3 Hz, 1 H), 7.80 (d, J=8.6 Hz, 2 H), 8.01 (d, J=6.6 Hz, 1 H), 8.15 (s, 1 H), 8.38 (s, 1 H).

Compound 45: $^1$H NMR (400 MHz, DMSO-d$_6$) δ ppm 2.24 (s, 3 H) 3.78 (s, 3 H) 6.84 (t, J=6.86 Hz, 1 H) 7.08 (dd, J=8.88, 2.02 Hz, 1 H) 7.11 (d, J=7.27 Hz, 1 H) 7.25 (d, J=2.02 Hz, 1 H) 7.27 (d, J=8.88 Hz, 1 H) 7.29 (t, J=8.88 Hz, 2 H) 7.95 (s, 1 H) 8.06 (dd, J=8.88, 5.25 Hz, 2 H) 8.10 (dd, J=6.46, 0.81 Hz, 1 H) 8.40 (s, 1 H) 8.58 (s, 1 H).

Compound 46: $^1$H NMR (360 MHz, CDCl$_3$) δ ppm 2.31 (s, 3 H) 2.66 (s, 3 H) 3.88 (s, 3 H) 6.75-6.84 (m, 2 H) 6.93 (ddd, J=7.96, 2.65, 1.10 Hz, 1 H) 7.32-7.38 (m, 3 H) 7.40 (t, J=7.87 Hz, 1 H) 7.52-7.61 (m, 2 H) 8.46 (s, 1 H) 8.68 (s, 2 H).

Compound 57: $^1$H NMR (360 MHz, DMSO-d$_6$) δ ppm 2.15 (s, 3 H) 3.80 (s, 3 H) 6.99 (t, J=7.32 Hz, 1 H) 7.03-7.08 (m, 2 H) 7.15 (d, J=7.32 Hz, 1 H) 7.25 (d, J=2.20 Hz, 1 H) 7.28 (d, J=8.42 Hz, 1 H) 7.38 (t, J=8.78 Hz, 2 H) 7.68 (s, 1 H) 7.95 (d, J=6.95 Hz, 1 H) 8.13 (dd, J=8.60, 5.67 Hz, 2 H) 8.62 (s, 1 H).

Compound 58: $^1$H NMR (360 MHz, CDCl$_3$) δ ppm 2.31 (s, 3 H) 3.87 (s, 3 H) 6.91 (s, 1 H) 6.93-7.03 (m, 3 H) 7.13 (d, J=7.68 Hz, 1 H) 7.21 (t, J=8.60 Hz, 2 H) 7.26 (d, J=8.42 Hz, 1 H) 7.34 (s, 1 H) 7.67 (d, J=0.73 Hz, 1 H) 7.88 (d, J=6.59 Hz, 1 H) 8.20 (dd, J=8.60, 5.31 Hz, 2 H).

Compound 63: $^1$H NMR (360 MHz, DMSO-d$_6$) δ ppm 1.19 (t, J=7.50 Hz, 3 H) 2.53-2.57 (m, 2 H) 2.65 (s, 3 H) 3.80 (s, 3 H) 3.83 (s, 3 H) 6.87 (t, J=7.14 Hz, 1 H) 6.90-6.98 (m, 1

H) 7.02-7.08 (m, 3 H) 7.25 (d, J=2.20 Hz, 1 H) 7.28 (d, J=8.42 Hz, 1 H) 7.37-7.46 (m, 3 H) 7.69 (s, 1 H) 7.89 (d, J=6.59 Hz, 1 H) 8.47 (s, 1 H).

Compound 64: ¹H NMR (600 MHz, CDCl₃) δ ppm 2.32 (s, 3 H) 2.68 (s, 3 H) 3.93 (s, 3 H) 6.87-6.96 (m, 1 H) 6.97-7.01 (m, 2 H) 7.05-7.12 (m, 1 H) 7.35 (d, J=8.80 Hz, 2 H) 7.36-7.39 (m, 1 H) 7.42 (t, J=7.78 Hz, 1 H) 7.45-7.49 (m, 3 H) 7.54 (d, J=6.75 Hz, 1 H) 7.75 (s, 1 H).

Compound 65: ¹H NMR (360 MHz, CDCl₃) δ ppm 2.19 (s, 3 H) 2.66 (s, 3 H) 3.91 (s, 3 H) 6.80 (t, J=7.14 Hz, 1 H) 6.91 (s, 1 H) 6.91-6.96 (m, 1 H) 6.99 (d, J=7.32 Hz, 1 H) 7.23-7.29 (m, 1 H) 7.33-7.45 (m, 6 H) 7.52 (d, J=6.59 Hz, 1 H) 7.57 (s, 1 H).

Compound 66: ¹H NMR (360 MHz, CDCl₃) δ ppm 2.31 (s, 3 H) 2.66 (s, 3 H) 3.91 (s, 3 H) 6.81 (t, J=7.14 Hz, 1 H) 6.91-6.96 (m, 2 H) 6.99 (d, J=7.32 Hz, 1 H) 7.12 (dd, J=8.96, 2.56 Hz, 1 H) 7.28-7.46 (m, 6 H) 7.54 (d, J=6.59 Hz, 1 H) 7.68 (s, 1 H).

Compound 67: ¹H NMR (360 MHz, DMSO-d₆) δ ppm 2.34 (s, 3 H) 2.65 (s, 3 H) 3.77-3.88 (m, 6 H) 6.88 (t, J=7.14 Hz, 1 H) 6.93-7.00 (m, 1 H) 7.02-7.13 (m, 2 H) 7.27 (d, J=2.20 Hz, 1 H) 7.39-7.43 (m, 3 H) 7.47 (d, J=8.78 Hz, 1 H) 7.91 (d, J=6.59 Hz, 1 H) 8.55 (s, 1 H) 8.67 (s, 1 H).

Compound 70: ¹H NMR (360 MHz, DMSO-d₆) δ ppm 2.34 (s, 3 H) 2.56 (s, 3 H) 3.84 (s, 3 H) 6.82 (t, J=7.14 Hz, 1 H) 7.06 (d, J=7.32 Hz, 1 H) 7.10 (dd, J=8.78, 2.20 Hz, 1 H) 7.21-7.35 (m, 4 H) 7.48 (d, J=8.78 Hz, 1 H) 8.02 (d, J=7.68 Hz, 1 H) 8.11 (d, J=6.59 Hz, 1 H) 8.21 (s, 1 H) 8.54 (s, 1 H) 8.67 (s, 1 H).

Compound 71: ¹H NMR (360 MHz, DMSO-d₆) δ ppm 2.36 (s, 3 H) 2.55 (s, 3 H) 6.80 (dd, J=7.32, 6.59 Hz, 1 H) 6.95 (dd, J=7.68, 0.73 Hz, 1 H) 7.20-7.35 (m, 3 H) 7.51 (m, J=8.78 Hz, 2 H) 7.73 (m, J=9.15 Hz, 2 H) 7.97-8.04 (m, 1 H) 8.09 (dd, J=6.59, 0.73 Hz, 1 H) 8.19 (s, 1 H) 8.49 (s, 1 H) 9.04 (s, 1 H).

Compound 73: ¹H NMR (360 MHz, DMSO-d₆) δ ppm 2.36 (s, 3 H) 2.66 (s, 3 H) 6.83 (dd, J=7.32, 6.95 Hz, 1 H) 6.96 (d, J=7.68 Hz, 1 H) 7.52 (m, 2 H) 7.56 (d, J=8.42 Hz, 1 H) 7.61 (dd, J=8.05, 1.83 Hz, 1 H) 7.74 (m, 2 H) 8.10 (dd, J=6.59, 1.10 Hz, 1 H) 8.36 (s, 1 H) 8.44 (d, J=1.46 Hz, 1 H) 8.59 (s, 1 H) 9.05 (s, 1 H).

Compound 74: ¹H NMR (360 MHz, DMSO-d₆) δ ppm 2.36 (s, 3 H) 2.65 (s, 3 H) 6.88 (t, J=7.14 Hz, 1 H) 7.11 (d, J=7.32 Hz, 1 H) 7.33 (dd, J=8.78, 2.20 Hz, 1 H) 7.40 (dd, J=13.17, 2.20 Hz, 1 H) 7.51-7.67 (m, 3 H) 8.19 (d, J=6.59 Hz, 1 H) 8.39 (s, 1 H) 8.42 (s, 1 H) 8.76 (d, J=1.83 Hz, 1 H) 8.90 (s, 1 H).

Compound 75: ¹H NMR (360 MHz, DMSO-d₆) δ ppm 2.47 (s, 3 H) 2.66 (s, 3 H) 6.85 (t, J=7.14 Hz, 1 H) 7.05 (d, J=7.32 Hz, 1 H) 7.44-7.65 (m, 6 H) 8.00 (s, 1 H) 8.14 (d, J=6.59 Hz, 1 H) 8.38 (s, 1 H) 8.44 (d, J=1.46 Hz, 1 H) 8.70 (s, 1 H). Compound 76: ¹H NMR (360 MHz, DMSO-d₆) δ ppm 0.94 (t, J=7.32 Hz, 3 H) 1.38 (sxt, J=7.39 Hz, 2 H) 1.79 (quin, J=7.50 Hz, 2 H) 2.39 (s, 3 H) 2.86 (t, J=7.50 Hz, 2 H) 7.31 (dd, J=8.05, 6.59 Hz, 1 H) 7.47 (m, 2 H) 7.53 (d, J=7.68 Hz, 1 H) 7.82 (m, 2 H) 8.15 (s, 1 H) 8.34 (d, J=5.85 Hz, 1 H) 9.26 (s, 1 H) 9.66 (s, 1 H) 15.14 (br. s., 1 H).

Compound 77: 1H NMR (360 MHz, DMSO-d₆) δ ppm 2.33 (s, 3 H) 2.37 (s, 3 H) 3.82 (s, 3 H) 6.73 (dd, J=7.32, 6.95 Hz, 1 H) 6.99 (d, J=7.32 Hz, 1 H) 7.04 (dd, J=8.78, 2.20 Hz, 1 H) 7.23 (d, J=2.56 Hz, 1 H) 7.44 (d, J=8.78 Hz, 1 H) 7.68 (d, J=0.73 Hz, 1 H) 7.99 (dd, J=6.59, 0.73 Hz, 1 H) 8.51 (s, 1 H) 8.65 (s, 1 H).

Compound 78: ¹H NMR (360 MHz, DMSO-d₆) δ ppm 2.36 (s, 3 H) 2.36 (d, J=0.73 Hz, 3 H) 6.71 (dd, J=7.50, 6.77 Hz, 1 H) 6.88 (dd, J=7.68, 0.73 Hz, 1 H) 7.46 (d, J=8.78 Hz, 1 H) 7.67 (d, J=1.10 Hz, 1 H) 7.69 (m, 2 H) 7.97 (dd, J=6.59, 0.73 Hz, 1 H) 8.50 (s, 1 H) 9.02 (s, 1 H).

Compound 80: ¹H NMR (360 MHz, DMSO-d₆) δ ppm 2.37 (s, 3 H) 3.83 (s, 3 H) 6.73 (dd, J=7.50, 6.77 Hz, 1 H) 7.01 (dd, J=7.68, 0.73 Hz, 1 H) 7.07 (dd, J=8.78, 2.20 Hz, 1 H) 7.25 (d, J=2.20 Hz, 1 H) 7.46 (d, J=8.42 Hz, 1 H) 7.68 (d, J=0.73 Hz, 1 H) 8.00 (dd, J=6.59, 1.10 Hz, 1 H) 8.15 (s, 1 H) 8.55 (s, 1 H) 8.81 (s, 1 H).

Compound 81: ¹H NMR (360 MHz, CDCl₃) δ ppm 2.51 (s, 3 H) 2.63 (s, 3 H) 6.87 (t, J=6.95 Hz, 1 H) 7.10 (d, J=8.78 Hz, 1 H) 7.42 (d, J=8.05 Hz, 1 H) 7.52 (dd, J=7.87, 1.65 Hz, 1 H) 7.75 (s, 1 H) 7.81 (dd, J=6.95, 0.73 Hz, 1 H) 7.87 (dd, J=8.96, 2.74 Hz, 1 H) 8.22 (s, 1 H) 8.24 (d, J=1.10 Hz, 1 H) 8.33 (d, J=6.95 Hz, 1 H) 8.37 (s, 1 H) 8.60 (d, J=2.56 Hz, 1 H).

Compound 82: ¹H NMR (360 MHz, CDCl₃) δ ppm 2.51 (s, 3 H) 2.57 (s, 3 H) 6.83 (t, J=7.14 Hz, 1 H) 7.05 (d, J=9.15 Hz, 1 H) 7.28-7.36 (m, 3 H) 7.69 (s, 1 H) 7.80 (d, J=6.59 Hz, 1 H) 7.84 (dd, J=8.78, 2.93 Hz, 1 H) 7.87-7.91 (m, 1 H) 8.26 (s, 1 H) 8.29 (d, J=7.68 Hz, 1 H) 8.37 (s, 1 H) 8.59 (d, J=2.56 Hz, 1 H).

Compound 83: ¹H NMR (360 MHz, CDCl₃) δ ppm 2.44 (s, 3 H) 2.51 (s, 3 H) 6.93 (t, J=7.32 Hz, 1 H) 7.01 (dd, J=8.78, 0.73 Hz, 1 H) 7.32-7.43 (m, 2 H) 7.48-7.63 (m, 3 H) 7.82 (dd, J=8.78, 2.56 Hz, 1 H) 8.20 (s, 1 H) 8.30-8.39 (m, 2 H) 8.58 (d, J=2.56 Hz, 1 H).

Compound 84: ¹H NMR (360 MHz, DMSO-d₆) δ ppm 2.39 (s, 3 H) 2.65 (s, 3 H) 6.85 (t, J=6.95 Hz, 1 H) 6.97 (d, J=7.32 Hz, 1 H) 7.56 (d, J=8.42 Hz, 1 H) 7.60 (dd, J=8.05, 1.83 Hz, 1 H) 7.75 (d, J=8.78 Hz, 1 H) 7.99 (dd, J=8.78, 2.56 Hz, 1 H) 8.15 (dd, J=6.59, 0.73 Hz, 1 H) 8.38 (s, 1 H) 8.42 (d, J=1.46 Hz, 1 H) 8.54 (d, J=2.56 Hz, 1 H) 8.83 (s, 1 H) 9.14 (s, 1 H).

Compound 86: ¹H NMR (360 MHz, DMSO-d₆) δ ppm 2.39 (s, 3 H) 2.55 (s, 3 H) 6.81 (t, J=7.14 Hz, 1 H) 6.95 (d, J=6.95 Hz, 1 H) 7.21-7.33 (m, 3 H) 7.74 (d, J=8.78 Hz, 1 H) 7.91-8.02 (m, 2 H) 8.14 (dd, J=6.59, 0.73 Hz, 1 H) 8.21 (s, 1 H) 8.53 (d, J=2.56 Hz, 1 H) 8.77 (s, 1 H) 9.13 (s, 1 H).

Compound 87: ¹H NMR (360 MHz, CDCl₃) δ ppm 2.44 (s, 3 H) 2.51 (s, 3 H) 6.84 (t, J=7.32, 6.59 Hz, 1 H) 6.89 (dd, J=7.68, 0.73 Hz, 1 H) 7.32 (s, 1 H) 7.33-7.42 (m, 2 H) 7.47-7.60 (m, 3 H) 7.81 (d, J=1.83 Hz, 2 H) 8.42 (t, J=1.83 Hz, 1 H) 8.97 (s, 1 H).

Compound 89: ¹H NMR (360 MHz, DMSO-d₆) δ ppm 2.34 (s, 3 H) 2.56 (s, 3 H) 3.84 (s, 3 H) 6.83 (t, J=6.95 Hz, 1 H) 7.04-7.21 (m, 4 H) 7.27 (d, J=2.20 Hz, 1 H) 7.48 (d, J=8.42 Hz, 1 H) 8.03 (dd, J=8.42, 6.22 Hz, 1 H) 8.11 (dd, J=6.59, 0.73 Hz, 1 H) 8.19 (s, 1 H) 8.54 (s, 1 H) 8.67 (s, 1 H).

Compound 90: ¹H NMR (360 MHz, CDCl₃) δ ppm 2.51 (s, 3 H) 2.55 (s, 3 H) 6.74 (t, J=6.95 Hz, 1 H) 6.92 (d, J=7.32 Hz, 1 H) 6.95-7.05 (m, 2 H) 7.33 (s, 1 H) 7.41 (m, 2 H) 7.62 (m, 2 H) 7.64 (s, 1 H) 7.72 (dd, J=6.59, 0.73 Hz, 1 H) 7.83 (dd, J=9.15, 6.22 Hz, 1 H) 8.39 (s, 1 H).

Compound 91: ¹H NMR (400 MHz, DMSO-d₆) δ ppm 2.36 (s, 3 H) 2.55 (s, 3 H) 6.85 (dd, J=6.86 Hz, 1 H) 7.09 (dd, J=7.67, 0.81 Hz, 1 H) 7.10-7.20 (m, 2 H) 7.31 (dd, J=8.88, 2.02 Hz, 1 H) 7.37 (dd, J=13.32, 2.42 Hz, 1 H) 7.60 (t, J=8.88 Hz, 1 H) 7.99 (dd, J=8.68, 6.26 Hz, 1 H) 8.17 (dd, J=6.46, 0.81 Hz, 1 H) 8.20 (s, 1 H) 8.74 (d, J=2.02 Hz, 1 H) 8.81 (s, 1 H).
Compound 94: ¹H NMR (360 MHz, CDCl₃) δ ppm 2.49 (s, 3 H) 2.51 (s, 3 H) 3.87 (s, 3 H) 6.76 (t, J=6.95 Hz, 1 H) 6.85 (dd, J=8.23, 2.74 Hz, 1 H) 6.98 (d, J=7.32 Hz, 1 H) 7.17-7.24 (m, 3 H) 7.45 (s, 1 H) 7.49 (d, J=2.93 Hz, 1 H) 7.71 (s, 1 H) 7.72-7.80 (m, 2 H) 8.46 (d, J=2.56 Hz, 1 H).

Compound 98: ¹H NMR (360 MHz, DMSO-d₆) δ ppm 2.39 (s, 3 H) 2.55 (s, 3 H) 6.83 (t, J=6.95 Hz, 1 H) 6.96 (d, J=7.68, 0.73 Hz, 1 H) 7.09-7.21 (m, 2 H) 7.74 (d, J=8.78 Hz, 1 H) 7.93-8.03 (m, 2 H) 8.13 (dd, J=6.59, 0.73 Hz, 1 H) 8.20 (s, 1 H) 8.52 (d, J=2.56 Hz, 1 H) 8.78 (s, 1 H) 9.13 (s, 1 H).

Compound 107: ¹H NMR (360 MHz, DMSO-d₆) δ ppm 2.15 (s, 3 H) 2.52 (s, 3 H) 3.76 (s, 2 H) 3.80 (s, 3 H) 6.80 (t, J=7.14 Hz, 1 H) 7.02 (d, J=7.68 Hz, 1 H) 7.03-7.08 (m, 2 H) 7.22-7.29 (m, 4 H) 7.68 (d, J=1.46 Hz, 1 H) 7.95 (s, 1 H) 8.09 (d, J=6.59 Hz, 1 H) 8.18 (s, 1 H) 8.46 (s, 1 H).

Compound 109: ¹H NMR (600 MHz, CDCl₃) δ ppm 2.31 (s, 3 H), 3.65 (q, J=10.7 Hz, 2 H), 3.84 (s, 3 H), 6.72 (t, J=7.1 Hz, 1 H), 6.89 (s, 1 H), 6.91-6.94 (m, 2 H), 6.97 (dd, J=8.4, 2.3 Hz, 1 H), 7.16 (s, 1 H), 7.21 (d, J=8.4 Hz, 1 H), 7.56 (s, 1 H), 7.65 (d, J=1.3 Hz, 1 H), 7.66 (d, J=6.6 Hz, 1 H).

Compound 111: ¹H NMR (360 MHz, CDCl₃) δ ppm 1.19 (t, J=7.68 Hz, 3 H) 2.26 (q, J=7.68 Hz, 2 H) 2.31 (s, 3 H) 2.55 (s, 3 H) 3.86 (s, 3 H) 4.50 (d, J=5.49 Hz, 2 H) 5.72 (br. s., 1 H) 6.75 (dd, J=7.32, 6.95 Hz, 1 H) 6.90 (t, J=1.10 Hz, 1 H) 6.93-6.98 (m, 2 H) 7.00 (dd, J=8.42, 2.20 Hz, 1 H) 7.19-7.24 (m, 2 H) 7.28 (d, J=8.05 Hz, 1 H) 7.37 (br. s., 1 H) 7.66 (d, J=1.46 Hz, 1 H) 7.70 (s, 1 H) 7.73 (dd, J=6.59, 0.73 Hz, 1 H) 7.87 (d, J=1.83 Hz, 1 H).

Compound 112: ¹H NMR (360 MHz, DMSO-d₆) δ ppm 2.17 (s, 3 H) 3.99 (s, 3 H) 6.87 (t, J=7.14 Hz, 1 H) 7.02 (d, J=7.68 Hz, 1 H) 7.18 (s, 1 H) 7.26-7.42 (m, 4 H) 7.48 (t, J=8.78 Hz, 1 H) 7.81 (s, 1 H) 7.88 (d, J=6.59 Hz, 1 H) 8.10 (dd, J=8.60, 5.67 Hz, 2 H) 8.74 (s, 1 H).

Compound 114: ¹H NMR (360 MHz, CDCl₃) δ ppm 2.50 (s, 3 H) 2.57 (s, 3 H) 3.30 (s, 3 H) 3.44-3.51 (m, 2 H) 3.56-3.63 (m, 2 H) 3.64-3.69 (m, 2 H) 3.69-3.75 (m, 2 H) 3.90 (s, 3 H) 4.09 (s, 2 H) 4.55 (d, J=6.22 Hz, 2 H) 7.03 (s, 1 H) 7.07 (t, J=7.14 Hz, 1 H) 7.13 (dd, J=8.60, 2.01 Hz, 1 H) 7.18 (d, J=2.20 Hz, 1 H) 7.28-7.38 (m, 3 H) 7.63 (t, J=5.85 Hz, 1 H) 7.82 (s, 1 H) 7.87 (s, 1 H) 7.92 (d, J=6.59 Hz, 1 H) 8.39 (d, J=1.10 Hz, 1 H) 9.55 (br. s., 1 H).

Compound 117: ¹H NMR (360 MHz, DMSO-d₆) δ ppm 1.13 (t, J=7.32 Hz, 3 H) 2.15 (s, 3 H) 3.13 (q, J=7.32 Hz, 2 H) 3.80 (s, 3 H) 6.88 (t, J=7.14 Hz, 1 H) 7.00-7.09 (m, 3 H) 7.20-7.32 (m, 2 H) 7.68 (d, J=1.10 Hz, 1 H) 8.08 (d, J=6.59 Hz, 1 H) 8.51-8.62 (m, 2 H).

Compound 124: ¹H NMR (360 MHz, CDCl₃) δ ppm 2.43 (s, 3 H) 2.49 (s, 3 H) 3.88 (s, 3 H) 6.83 (t, J=7.14 Hz, 1 H) 6.93 (d, J=2.20 Hz, 1 H) 7.00 (d, J=7.68 Hz, 1 H) 7.05 (dd, J=8.42, 2.20 Hz, 1 H) 7.32-7.42 (m, 3 H) 7.48-7.54 (m, 2 H) 7.54-7.59 (m, 1 H) 7.63 (d, J=8.42 Hz, 1 H) 8.50 (s, 1 H).

Compound 132: ¹H NMR (400 MHz, DMSO-d₆) δ ppm 2.34 (s, 3 H) 3.85 (s, 3 H) 4.00 (s, 3 H) 6.87 (t, J=7.27 Hz, 1 H) 7.03 (dd, J=7.67, 0.81 Hz, 1 H) 7.10 (dd, J=8.68, 2.22 Hz, 1 H) 7.28 (d, J=2.42 Hz, 1 H) 7.34 (t, J=8.88 Hz, 2 H) 7.49 (d, J=8.88 Hz, 1 H) 7.84 (dd, J=6.86, 0.81 Hz, 1 H) 8.12 (dd, J=8.88, 5.65 Hz, 2 H) 8.50 (s, 1 H) 8.67 (s, 1 H).

Compound 136: ¹H NMR (360 MHz, DMSO-d₆) δ ppm 1.70-1.95 (m, J=12.30, 12.30, 12.17, 4.21 Hz, 2 H) 2.04 (dd, J=12.62, 2.01 Hz, 2 H) 2.34 (s, 3 H) 3.13-3.26 (m, J=11.62, 11.62, 3.66, 3.48 Hz, 1 H) 3.51 (td, J=11.62, 1.65 Hz, 2 H) 3.85 (s, 3 H) 3.98 (dd, J=11.71, 2.20 Hz, 2 H) 7.00 (dd, J=8.78, 2.20 Hz, 1 H) 7.13 (d, J=2.20 Hz, 1 H) 7.32 (t, J=7.32 Hz, 1 H) 7.56 (d, J=8.42 Hz, 1 H) 7.63 (d, J=8.05 Hz, 1 H) 8.18 (s, 1 H) 8.35 (d, J=6.59 Hz, 1 H) 8.72 (s, 1 H) 9.56 (br. s., 1 H) 14.97 (br. s., 1 H).

Compound 138: ¹H NMR (360 MHz, CDCl₃) δ ppm 2.31 (s, 3 H) 2.35 (s, 3 H) 4.08 (s, 3 H) 6.56 (d, J=8.42 Hz, 1 H) 6.88 (s, 1 H) 6.91 (t, J=7.32 Hz, 1 H) 7.43 (d, J=8.42 Hz, 1 H) 7.50 (d, J=7.32 Hz, 1 H) 7.53-7.60 (m, 2 H) 7.61-7.69 (m, 2 H) 7.83 (d, J=7.68 Hz, 1 H) 8.10 (br. s., 1 H) 8.19 (d, J=7.68 Hz, 1 H).

Compound 140: ¹H NMR (360 MHz, CDCl₃) δ ppm 2.30 (s, 3 H) 3.29 (s, 3 H) 4.08 (s, 3 H) 4.70 (s, 2 H) 6.56 (d, J=8.42 Hz, 1 H) 6.86-6.93 (m, 2 H) 7.38-7.42 (m, 2 H) 7.44 (d, J=8.05 Hz, 1 H) 7.51-7.59 (m, 2 H) 7.65 (d, J=8.42 Hz, 1 H) 7.88 (d, J=6.59 Hz, 1 H) 8.07 (s, 1 H) 8.23 (d, J=7.68 Hz, 1 H).

Compound 141: ¹H NMR (360 MHz, DMSO-d₆) δ ppm 2.15 (s, 3 H) 4.00 (s, 6 H) 6.95 (t, J=7.14 Hz, 1 H) 7.06-7.13 (m, 2 H) 7.35 (t, J=8.78 Hz, 2 H) 7.70 (d, J=8.05 Hz, 1 H) 7.74 (s, 1 H) 7.90 (d, J=6.59 Hz, 1 H) 8.10-8.22 (m, 3 H) 9.17 (s, 1 H).

Compound 143: ¹H NMR (360 MHz, DMSO-d₆) δ ppm 1.63-1.80 (m, 2 H) 1.98 (dd, J=12.99, 2.01 Hz, 2 H) 2.15 (s, 3 H) 2.98 (tt, J=11.48, 3.70 Hz, 1 H) 3.48 (td, J=11.53, 1.83 Hz, 2 H) 3.91-4.00 (m, 5 H) 6.83 (t, J=7.32 Hz, 1 H) 7.06 (d, J=8.42 Hz, 1 H) 7.09 (s, 1 H) 7.66 (d, J=8.42 Hz, 1 H) 7.72 (s, 1 H) 7.73 (d, J=1.10 Hz, 1 H) 8.05 (dd, J=6.59, 0.73 Hz, 1 H) 8.13 (d, J=7.68 Hz, 1 H) 9.10 (s, 1 H).

Compound 144: ¹H NMR (360 MHz, DMSO-d₆) δ ppm 2.15 (s, 3 H) 2.38 (s, 3 H) 3.97 (s, 3 H) 6.80 (t, J=7.14 Hz, 1 H) 7.05-7.10 (m, 2 H) 7.65 (d, J=8.42 Hz, 1 H) 7.68 (s, 1 H) 7.72 (d, J=1.10 Hz, 1 H) 8.03 (d, J=6.59 Hz, 1 H) 8.15 (d, J=7.68 Hz, 1 H) 9.27 (s, 1 H).

Compound 145: ¹H NMR (360 MHz, DMSO-d₆) δ ppm 2.34 (s, 3 H) 2.38 (s, 3 H) 4.04 (s, 3 H) 7.01 (t, J=7.14 Hz, 1 H) 7.09 (d, J=8.42 Hz, 1 H) 7.41-7.53 (m, 2 H) 7.54-7.67 (m, 2 H) 7.82 (d, J=8.42 Hz, 1 H) 7.95 (d, J=6.22 Hz, 1 H) 8.26 (d, J=7.32 Hz, 1 H) 8.71 (s, 1 H) 9.41 (s, 1 H).

Compound 148: ¹H NMR (360 MHz, DMSO-d₆) δ ppm 2.18 (s, 3 H) 2.54 (s, 3 H) 6.97 (dd, J=11.16, 2.01 Hz, 1 H) 7.08-7.24 (m, 3 H) 7.39 (dd, J=8.60, 2.01 Hz, 1 H) 7.44-7.59 (m, 2 H) 7.86 (s, 1 H) 7.97 (dd, J=8.42, 6.22 Hz, 1 H) 8.17 (s, 1 H) 8.29 (dd, J=4.03, 2.20 Hz, 1 H) 9.06 (s, 1 H).

Compound 157: ¹H NMR (400 MHz, CDCl₃) δ ppm 2.32 (s, 3 H) 2.52 (s, 3 H) 3.88 (s, 3 H) 6.61 (s, 1 H) 6.93 (s, 1 H) 6.95-7.01 (m, 2 H) 7.03 (dd, J=8.28, 2.22 Hz, 1 H) 7.22-7.26 (m, 1 H) 7.33 (d, J=8.07 Hz, 1 H) 7.67 (dd, J=10.09, 2.83 Hz, 1 H) 7.70 (d, J=1.21 Hz, 1 H) 7.90 (br. s., 1 H) 7.99 (s, 1 H).

Compound 158: ¹H NMR (360 MHz, DMSO-d₆) δ ppm 1.68-1.87 (m, 2 H) 1.88-2.05 (m, 2 H) 2.16 (s, 3 H) 2.96-3.09 (m, 1 H) 3.49 (t, J=10.79 Hz, 2 H) 3.81 (s, 3 H) 3.89-4.04 (m, 2 H) 6.76 (s, 1 H) 7.08-7.15 (m, 2 H) 7.35 (d, J=1.83 Hz, 1 H) 7.43 (d, J=8.42 Hz, 1 H) 7.77 (s, 1 H) 8.20 (s, 1 H) 10.07 (s, 1 H).

Compound 159: ¹H NMR (360 MHz, DMSO-d₆) δ ppm 2.16 (s, 3 H) 2.56 (s, 3 H) 3.84 (s, 3 H) 6.74 (d, J=5.49 Hz, 1 H) 7.08-7.15 (m, 2 H) 7.17 (dd, J=8.42, 2.20 Hz, 1 H) 7.33-7.38 (m, 2 H) 7.40 (d, J=8.42 Hz, 1 H) 7.75 (d, J=1.10 Hz, 1 H) 7.88 (dd, J=10.61, 2.93 Hz, 1 H) 8.17 (d, J=5.49 Hz, 1 H) 8.46 (s, 1 H) 9.53 (s, 1 H).

Compound 160: ¹H NMR (360 MHz, DMSO-d₆) δ ppm 1.24 (d, J=6.95 Hz, 6 H) 2.16 (s, 3 H) 2.38 (s, 3 H) 2.96 (sxt, J=6.95 Hz, 1 H) 3.81 (s, 3 H) 6.65 (s, 1 H) 7.04-7.15 (m, 2 H) 7.32 (d, J=2.20 Hz, 1 H) 7.36 (d, J=8.42 Hz, 1 H) 7.73 (br. s., 1 H) 7.81 (s, 1 H) 9.41 (s, 1 H).

Compound 161: ¹H NMR (360 MHz, DMSO-d₆) δ ppm 2.15 (s, 3 H) 2.43 (s, 3 H) 3.81 (s, 6 H) 6.97 (s, 1 H) 7.05 (t, J=7.50 Hz, 1 H) 7.09 (s, 1 H) 7.11-7.20 (m, 2 H) 7.33 (d, J=1.83 Hz, 1 H) 7.38 (d, J=8.42 Hz, 1 H) 7.45 (td, J=8.42, 1.46 Hz, 1 H) 7.54 (dd, J=7.32, 1.46 Hz, 1 H) 7.72 (s, 1 H) 7.93 (s, 1 H) 9.53 (s, 1 H).

Compound 163: ¹H NMR (360 MHz, DMSO-d₆) δ ppm 1.32 (d, J=6.95 Hz, 6 H) 2.16 (s, 3 H) 3.09 (spt, J=6.95 Hz, 1 H) 4.09 (s, 3 H) 7.16 (s, 1 H) 7.28 (d, J=8.05 Hz, 1 H) 7.41 (td, J=7.68, 1.83 Hz, 1 H) 7.50 (td, J=7.68, 1.46 Hz, 1 H) 7.58 (dd, J=8.05, 1.46 Hz, 1 H) 7.80 (d, J=1.46 Hz, 1 H) 7.82 (d, J=8.05 Hz, 1 H) 8.17 (s, 1 H) 8.33 (dd, J=7.68, 1.83 Hz, 1 H) 8.57 (s, 1 H) 10.05 (s, 1 H).

Compound 170: ¹H NMR (360 MHz, DMSO-d₆) δ ppm 1.61-1.84 (m, 4 H) 2.16 (s, 3 H) 2.38 (s, 3 H) 2.84-2.99 (m, 1 H) 3.41 (td, J=11.25, 2.74 Hz, 2 H) 3.81 (s, 3 H) 3.88-3.99 (m, 2 H) 6.65 (s, 1 H) 7.09 (s, 1 H) 7.12 (dd, J=8.42, 2.20 Hz, 1 H)

7.31 (d, J=2.20 Hz, 1 H) 7.36 (d, J=8.42 Hz, 1 H) 7.73 (d, J=1.10 Hz, 1 H) 7.82 (s, 1 H) 9.42 (s, 1 H).

Compound 174: $^1$H NMR (360 MHz, DMSO-d$_6$) δ ppm 2.16 (s, 3 H) 4.04 (s, 3 H) 7.16 (s, 1 H) 7.31 (d, J=8.42 Hz, 1 H) 7.42 (t, J=7.32 Hz, 1 H) 7.51 (t, J=7.32 Hz, 1 H) 7.59 (d, J=7.68 Hz, 1 H) 7.82 (s, 1 H) 7.85 (d, J=8.42 Hz, 1 H) 8.23-8.40 (m, 2 H) 8.66 (s, 1 H) 10.47 (s, 1 H).

Compound 175: $^1$H NMR (400 MHz, DMSO-d$_6$) δ ppm 2.16 (s, 3 H) 3.84 (s, 3 H) 7.08 (s, 1 H) 7.28-7.38 (m, 3 H) 7.47 (d, J=4.84 Hz, 1 H) 7.70 (s, 1 H) 7.94 (dd, J=8.68, 2.22 Hz, 1 H) 7.99 (d, J=2.02 Hz, 1 H) 8.03 (d, J=4.44 Hz, 1 H) 8.11 (dd, J=8.88, 5.65 Hz, 2 H) 8.45 (s, 1 H) 9.58 (s, 1 H).

Compound 176: $^1$H NMR (600 MHz, CDCl$_3$) δ ppm 2.49 (s, 3 H), 2.54 (s, 3 H), 3.98 (s, 3 H), 6.99-7.04 (m, 2 H), 7.40 (dd, J=8.6, 2.3 Hz, 1 H), 7.51 (d, J=4.6 Hz, 1 H), 7.62 (d, J=4.6 Hz, 1 H), 7.64 (s, 1 H), 7.68 (d, J=8.6 Hz, 1 H), 7.78 (dd, J=8.2, 6.0 Hz, 1 H), 8.02 (d, J=2.2 Hz, 1 H), 8.19 (s, 1 H), 8.54 (s, 1 H).

Compound 177: $^1$H NMR (600 MHz, CDCl$_3$) δ ppm 2.50 (s, 3 H), 2.53 (s, 3 H), 4.01 (s, 3 H), 6.99-7.04 (m, 2 H), 7.21 (dd, J=8.6, 2.3 Hz, 1 H), 7.61 (s, 1 H), 7.71 (d, J=8.6 Hz, 1 H), 7.75-7.78 (m, 1 H), 7.79 (s, 1 H), 8.25 (d, J=2.3 Hz, 1 H), 8.31 (br. s., 1 H), 8.59 (s, 1 H).

Compound 171: $^1$H NMR (360 MHz, DMSO-d$_6$) δ ppm 2.16 (s, 3 H) 2.21 (s, 3 H) 4.06 (s, 3 H) 5.51 (s, 1 H) 5.83 (s, 1 H) 7.15 (s, 1 H) 7.29 (d, J=8.42 Hz, 1 H) 7.42 (td, J=7.68, 1.83 Hz, 1 H) 7.51 (td, J=7.59, 1.28 Hz, 1 H) 7.59 (dd, J=8.05, 1.10 Hz, 1 H) 7.80 (d, J=1.10 Hz, 1 H) 7.83 (d, J=8.42 Hz, 1 H) 8.36 (dd, J=7.68, 1.83 Hz, 1 H) 8.53 (s, 1 H) 8.63 (s, 1 H) 10.06 (s, 1 H).

Compound 178: $^1$H NMR (360 MHz, DMSO-d$_6$) δ ppm 2.35 (s, 3 H) 3.89 (s, 3 H) 7.34 (t, J=8.78 Hz, 2 H) 7.49 (d, J=4.39 Hz, 1 H) 7.53 (d, J=8.78 Hz, 1 H) 7.97-8.07 (m, 3 H) 8.12 (dd, J=8.42, 5.49 Hz, 2 H) 8.47 (s, 1 H) 8.71 (s, 1 H) 9.66 (s, 1 H).

Compound 179: $^1$H NMR (360 MHz, CDCl$_3$) δ ppm 2.33 (s, 3 H) 3.57-3.72 (m, 2 H) 4.08 (s, 3 H) 6.60 (d, J=8.42 Hz, 1 H) 6.81 (dd, J=7.68, 6.95 Hz, 1 H) 6.89 (t, J=1.10 Hz, 1 H) 7.47 (d, J=8.42 Hz, 1 H) 7.57 (s, 1 H) 7.67-7.76 (m, 2 H) 8.00 (s, 1 H) 8.14 (dd, J=7.68, 1.10 Hz, 1 H).

Pharmacology

A) Screening of the Compounds of the Invention for γ-secretase-modulating Activity A1) Method 1

Screening was carried out using SKNBE2 cells carrying the APP 695—wild type, grown in Dulbecco's Modified Eagle's Medium/Nutrient mixture F-12 (DMEM/NUT-mix F-12) (HAM) provided by Gibco (cat no. 31330-38) containing 5% Serum/Fe supplemented with 1% non-essential amino acids. Cells were grown to near confluency.

The screening was performed using the assay as described in Citron et al (1997) Nature Medicine 3: 67. Briefly, cells were plated in a 96-well plate at about $10^5$ cells/ml one day prior to addition of compounds. Compounds were added to the cells in Ultraculture (Lonza, BE12-725F) supplemented with 1% glutamine (Invitrogen, 25030-024) for 18 hours. The media were assayed by two sandwich ELISAs, for Aβ42 and Aβtotal. Toxicity of the compounds was assayed by WST-1 cell proliferation reagent (Roche, 1 644 807) according to the manufacturer's protocol.

To quantify the amount of Aβ42 in the cell supernatant, commercially available Enzyme-Linked-Immunosorbent-Assay (ELISA) kits were used (Innotest® β-Amyloid$_{(1-42)}$, Innogenetics N.V., Ghent, Belgium). The Aβ42 ELISA was performed essentially according to the manufacturer's protocol. Briefly, the standards (dilutions of synthetic Aβ1-42) were prepared in polypropylene Eppendorf with final concentrations of 8000 down to 3.9 pg/ml (1/2 dilution step).

Samples, standards and blanks (100 μl) were added to the anti-Aβ42-coated plate supplied with the kit (the capture antibody selectively recognizes the C-terminal end of the antigen). The plate was allowed to incubate 3 h at 25° C. in order to allow formation of the antibody-amyloid complex. Following this incubation and subsequent wash steps a selective anti-Aβ-antibody conjugate (biotinylated 3D6) was added and incubated for a minimum of 1 hour in order to allow formation of the antibody-Amyloid-antibody-complex. After incubation and appropriate wash steps, a Streptavidine-Peroxidase-Conjugate was added, followed 30 minutes later by an addition of 3,3',5,5'-tetramethylbenzidine (TMB)/peroxide mixture, resulting in the conversion of the substrate into a coloured product. This reaction was stopped by the addition of sulfuric acid (0.9 N) and the colour intensity was measured by means of photometry with an ELISA-reader with a 450 nm filter.

To quantify the amount of Aβtotal in the cell supernatant, samples and standards were added to a 6E10-coated plate. The plate was allowed to incubate overnight at 4° C. in order to allow formation of the antibody-amyloid complex. Following this incubation and subsequent wash steps a selective anti-Aβ-antibody conjugate (biotinylated 4G8) was added and incubated for a minimum of 1 hour in order to allow formation of the antibody-Amyloid-antibody-complex. After incubation and appropriate wash steps, a Streptavidine-Peroxidase-Conjugate was added, followed 30 minutes later by an addition of Quanta Blu fluorogenic peroxidase substrate according to the manufacturer's instructions (Pierce Corp., Rockford, Ill.).

To obtain the values reported in Table 12a, the sigmoidal dose response curves were analysed by computerised curve-fitting, with percent of inhibition plotted against compound concentration. A 4-parameter equation (model 205) in XLfit was used to determine the $IC_{50}$. The top and the bottom of the curve were fixed to 100 and 0, respectively, and the hill slope was fixed to 1. The $IC_{50}$ represents the concentration of a compound that is required for inhibiting a biological effect by 50% (Here, it is the concentration where Aβ peptide level is reduced by 50%).

The $IC_{50}$ values are shown in Table 12a:

| Co. No. | $IC_{50}$ Aβ42 (μM) | $IC_{50}$ Aβtotal (μM) |
| --- | --- | --- |
| 1 | 0.101 | >5 |
| 2 | 0.065 | >3 |
| 3 | 0.030 | >1 |
| 4 | 0.053 | >3 |
| 5 | 0.014 | >1 |
| 6 | 0.239 | >10 |
| 7 | 0.037 | >1 |
| 8 | 0.541 | >20 |
| 9 | 0.384 | >10 |
| 10 | 0.054 | >3 |
| 11 | 0.039 | >3 |
| 12 | 0.064 | >3 |
| 13 | 0.089 | >3 |
| 14 | 0.057 | >3 |
| 15 | 0.012 | >3 |
| 16 | 0.058 | >3 |
| 17 | 0.080 | >3 |
| 18 | 0.025 | >10 |
| 19 | 0.059 | >3 |
| 21 | 0.263 | >5 |
| 22 | 0.113 | >3 |
| 23 | 0.025 | >3 |

-continued

| Co. No. | IC$_{50}$ Aβ42 (μM) | IC$_{50}$ Aβtotal (μM) |
|---|---|---|
| 24 | 0.024 | >1 |
| 25 | 0.251 | >10 |
| 26 | 0.011 | >3 |
| 27 | 0.025 | >3 |
| 28 | 0.020 | >1 |
| 29 | 0.010 | >1 |
| 30 | 0.057 | >3 |
| 31 | 0.595 | >5 |
| 32 | 0.114 | >5 |
| 33 | 0.031 | >3 |
| 34 | 0.009 | >3 |
| 35 | 0.019 | >1 |
| 36 | 0.064 | >3 |
| 37 | 0.190 | >10 |
| 38 | 0.054 | >3 |
| 39 | 0.075 | >3 |
| 40 | 0.062 | >3 |
| 41 | 0.344 | 8.54 |
| 42 | 0.430 | >10 |
| 45 | 0.232 | >5 |
| 46 | 0.052 | >3 |
| 47 | 0.031 | >3 |
| 48 | 0.060 | >3 |
| 49 | 0.305 | 10 |
| 50 | 0.253 | >3 |
| 51 | 0.039 | >3 |
| 52 | 0.010 | >3 |
| 54 | 0.070 | >3 |
| 56 | 0.601 | >10 |
| 57 | 0.058 | >1 |
| 59 | 0.123 | >3 |
| 61 | 0.423 | >10 |
| 62 | 0.477 | >10 |
| 63 | 0.029 | >3 |
| 64 | 0.013 | >3 |
| 65 | 0.782 | 27.2 |
| 67 | 0.051 | >3 |
| 68 | 0.018 | >1 |
| 71 | 0.288 | >3 |
| 77 | 2.691 | >10 |
| 78 | 6.442 | >10 |
| 88 | 0.184 | >3 |

To obtain the values reported in Table 12b, the data are calculated as percentage of the maximum amount of amyloid Beta 42 measured in the absence of the test compound. The sigmoidal dose response curves were analyzed using non-linear regression analysis with percentage of the control plotted against the log concentration of the compound. A 4-parameter equation was used to determine the IC$_{50}$. The values reported in Table 12b are averaged IC$_{50}$ values.

The IC$_{50}$ values are shown in Table 12b:

| Co. No. | IC$_{50}$ Aβ42 (μM) | IC$_{50}$ Aβtotal (μM) |
|---|---|---|
| 1 | 0.098 | >5.012 |
| 2 | 0.055 | >3.020 |
| 3 | 0.148 | 12.589 |
| 4 | 0.085 | >3.020 |
| 5 | 0.012 | >3.020 |
| 6 | 0.263 | >10 |
| 7 | 0.036 | >3.020 |
| 8 | 0.562 | >19.953 |
| 9 | 0.282 | >10 |
| 10 | 0.051 | >3.020 |
| 11 | 0.035 | >3.020 |
| 12 | 0.055 | >3.020 |
| 13 | 0.087 | >3.020 |
| 14 | 0.041 | >3.020 |
| 15 | 0.011 | >3.020 |
| 16 | 0.049 | >3.020 |
| 17 | 0.071 | >3.020 |
| 18 | 0.025 | >10 |
| 19 | 0.056 | >3.020 |
| 20 | 0.871 | 5.754 |
| 21 | 0.204 | >5.012 |
| 22 | 0.112 | >3.020 |
| 23 | 0.022 | >3.020 |
| 24 | 0.020 | >10 |
| 25 | 0.240 | >10 |
| 26 | 0.011 | >3.020 |
| 27 | 0.025 | >3.020 |
| 28 | 0.018 | >3.020 |
| 29 | 0.008 | >10 |
| 30 | 0.045 | >3.020 |
| 31 | 0.589 | >30.200 |
| 32 | 0.105 | >5.012 |
| 33 | 0.027 | >3.020 |
| 34 | 0.009 | >3.020 |
| 35 | 0.019 | >3.020 |
| 36 | 0.060 | >3.020 |
| 37 | 0.174 | >10 |
| 38 | 0.051 | >3.020 |
| 39 | 0.068 | >3.020 |
| 40 | 0.056 | >3.020 |
| 41 | 0.363 | 7.413 |
| 42 | 0.427 | >10 |
| 43 | >3.02 | >3.020 |
| 44 | 0.617 | >3.020 |
| 45 | 0.200 | >5.012 |
| 46 | 0.050 | >3.020 |
| 47 | 0.031 | >3.020 |
| 48 | 0.052 | >3.020 |
| 49 | 0.407 | >10 |
| 50 | 0.251 | >5.012 |
| 51 | 0.038 | >3.020 |
| 52 | 0.010 | >3.020 |
| 53 | 0.027 | >3.020 |
| 54 | 0.068 | >3.020 |
| 55 | 1.288 | >3.020 |
| 56 | 0.204 | >10 |
| 57 | 0.051 | >3.020 |
| 58 | <0.11 | >3.020 |
| 59 | 0.145 | >3.020 |
| 60 | <0.11 | >3.020 |
| 61 | 0.437 | >10 |
| 62 | 0.417 | >3.020 |
| 63 | 0.029 | >3.020 |
| 64 | 0.017 | >3.020 |
| 65 | 0.661 | 17.783 |
| 66 | 0.076 | n.d. |
| 67 | 0.040 | >3.020 |
| 68 | 0.018 | >3.020 |
| 74 | 0.123 | >3.020 |
| 75 | 0.126 | >3.020 |
| 76 | 1.950 | >10 |
| 77 | 4.365 | >10 |
| 78 | 9.550 | >10 |
| 79 | 7.413 | >10 |
| 80 | 3.802 | >10 |
| 81 | 0.380 | >10 |
| 82 | 0.562 | >3.020 |
| 83 | 0.355 | >10 |
| 84 | 0.115 | >3.020 |
| 86 | 0.117 | >10 |
| 87 | 0.025 | >10 |
| 88 | 0.174 | >10 |
| 89 | 0.085 | >3.020 |
| 90 | 0.398 | >3.020 |
| 91 | 0.072 | 18.621 |
| 94 | 0.115 | >3.020 |
| 98 | 0.032 | >3.020 |
| 100 | 0.011 | >3.020 |
| 101 | 0.013 | >1 |

-continued

| Co. No. | IC$_{50}$ Aβ42 (μM) | IC$_{50}$ Aβtotal (μM) |
|---|---|---|
| 102 | 0.010 | >3.020 |
| 103 | 0.013 | >3.020 |
| 105 | 0.089 | >3.020 |
| 109 | 0.015 | >3.020 |
| 113 | 0.038 | >3.020 |
| 116 | 0.295 | >3.020 |
| 118 | 0.331 | >3.020 |
| 119 | 1.660 | >3.020 |
| 120 | 0.589 | >30.200 |
| 124 | 0.011 | >3.020 |
| 125 | 0.030 | >3.020 |
| 127 | 0.089 | >10 |
| 129 | 0.046 | >10 |
| 130 | 0.178 | >3.020 |
| 131 | 0.245 | >10 |
| 133 | 0.468 | >3.020 |
| 134 | 0.575 | >3.020 |
| 135 | 0.631 | >10 |
| 136 | 0.676 | >30.200 |
| 137 | 1.380 | >3.020 |
| 138 | 0.009 | >3.020 |
| 144 | 0.100 | >3.020 |
| 146 | 0.032 | >3.020 |
| 147 | 0.042 | >3.020 |
| 149 | 0.389 | >10 |
| 151 | 0.513 | >3.020 |
| 152 | 1.778 | >3.020 |
| 153 | 1.905 | >3.020 |
| 154 | >3.02 | >3.020 |
| 155 | 0.024 | >3.020 |
| 156 | >3.02 | >3.020 |
| 157 | 0.102 | >3.020 |
| 164 | 0.178 | >10 |
| 168 | 3.020 | >3.020 |
| 173 | >3.02 | >3.020 |
| 175 | 0.041 | >3.020 |
| 176 | 0.324 | >10 |
| 177 | 0.234 | >3.020 |

A2) Method 2

Screening was carried out using SKNBE2 cells carrying the APP 695—wild type, grown in Dulbecco's Modified Eagle's Medium/Nutrient mixture F-12 (DMEM/NUT-mix F-12) (HAM) provided by Invitrogen (cat no. 10371-029) containing 5% Serum/Fe supplemented with 1% non-essential amino acids, 1-glutamine 2 mM, Hepes 15 mM, penicillin 50 U/ml (units/ml) en streptomycin 50 μg/ml. Cells were grown to near confluency.

The screening was performed using a modification of the assay as described in Citron et al (1997) Nature Medicine 3: 67. Briefly, cells were plated in a 384-well plate at 10$^4$ cells/well in Ultraculture (Lonza, BE12-725F) supplemented with 1% glutamine (Invitrogen, 25030-024), 1% non-essential amino acid (NEAA), penicillin 50 U/ml en streptomycin 50 μg/ml in the presence of test compound at different test concentrations. The cell/compound mixture was incubated overnight at 37° C., 5% CO$_2$. The next day the media were assayed by two sandwich immuno-assays, for Aβ42 and Aβtotal.

Aβtotal and Aβ42 concentrations were quantified in the cell supernatant using the Aphalisa technology (Perkin Elmer). Alphalisa is a sandwich assay using biotinylated antibody attached to streptavidin coated donorbeads and antibody conjugated to acceptor beads. In the presence of antigen, the beads come into close proximity. The excitation of the donor beads provokes the release of singlet oxygen molecules that trigger a cascade of energy transfer in the acceptor beads, resulting in light emission. To quantify the amount of Aβ42 in the cell supernatant, monoclonal antibody specific to the C-terminus of Aβ42 (JRF/cAβ42/26) was coupled to the receptor beads and biotinylated antibody specific to the N-terminus of Aβ (JRF/AβN/25) was used to react with the donor beads. To quantify the amount of Aβtotal in the cell supernatant, monoclonal antibody specific to the N-terminus of Aβ (JRF/AβN/25) was coupled to the receptor beads and biotinylated antibody specific to the mid region of Aβ (biotinylated 4G8) was used to react with the donor beads.

To obtain the values reported in Table 12c, the data are calculated as percentage of the maximum amount of amyloid Beta 42 measured in the absence of the test compound. The sigmoidal dose response curves were analyzed using non-linear regression analysis with percentage of the control plotted against the log concentration of the compound. A 4-parameter equation was used to determine the IC$_{50}$.

The IC$_{50}$ values are shown in Table 12c:

| Co. No. | IC$_{50}$ Aβ42 (μM) | IC$_{50}$ Aβtotal (μM) |
|---|---|---|
| 1 | 0.155 | 7.413 |
| 4 | 0.166 | >10 |
| 15 | 0.038 | 5.495 |
| 29 | 0.013 | 7.079 |
| 33 | 0.071 | 5.754 |
| 50 | 0.309 | >10 |
| 69 | 0.046 | >10 |
| 70 | 0.068 | >3.020 |
| 71 | 0.407 | >3.020 |
| 73 | 0.166 | >3.020 |
| 102 | 0.014 | >10 |
| 103 | 0.019 | >10 |
| 104 | 0.029 | 7.244 |
| 105 | 0.032 | 6.607 |
| 106 | 0.034 | 4.571 |
| 107 | 0.048 | 2.042 |
| 108 | 0.054 | >10 |
| 109 | 0.060 | >10 |
| 110 | 0.129 | >10 |
| 111 | 0.065 | 5.495 |
| 112 | 0.107 | >10 |
| 113 | 0.145 | >10 |
| 114 | 0.151 | 3.631 |
| 115 | 0.257 | 8.318 |
| 117 | 0.331 | >10 |
| 118 | 0.372 | >10 |
| 119 | 0.603 | 6.166 |
| 120 | 0.363 | >10 |
| 121 | 1.318 | >10 |
| 123 | 5.370 | >10 |
| 124 | 0.018 | 9.120 |
| 125 | 0.051 | 7.943 |
| 126 | 0.052 | >10 |
| 127 | 0.056 | >10 |
| 128 | 0.062 | >10 |
| 129 | 0.074 | >10 |
| 132 | 0.251 | 6.918 |
| 134 | 0.437 | 1.738 |
| 135 | 0.102 | >10 |
| 136 | 0.813 | >10 |
| 137 | 0.871 | >10 |
| 138 | 0.005 | 5.888 |
| 139 | 0.005 | 4.266 |
| 140 | 0.006 | 4.074 |
| 141 | 0.013 | >10 |
| 142 | 0.031 | 6.607 |
| 143 | 0.060 | 3.388 |
| 144 | 0.120 | >10 |
| 145 | 0.007 | >10 |
| 148 | 0.043 | >10 |
| 149 | 0.174 | >10 |
| 150 | 0.200 | >10 |
| 151 | 0.219 | >10 |
| 155 | 0.028 | >10 |
| 157 | 0.050 | 7.413 |
| 158 | 0.071 | 8.913 |

-continued

| Co. No. | IC$_{50}$ Aβ42 (μM) | IC$_{50}$ Aβtotal (μM) |
|---|---|---|
| 159 | 0.055 | 4.786 |
| 160 | 0.087 | >10 |
| 161 | 0.132 | >10 |
| 162 | 0.138 | >10 |
| 163 | 0.166 | 8.318 |
| 165 | 0.178 | >10 |
| 166 | 0.251 | >10 |
| 167 | 0.288 | >10 |
| 168 | 0.380 | 10 |
| 169 | 0.417 | 7.943 |
| 170 | 0.447 | >10 |
| 171 | 0.537 | 8.318 |
| 172 | 0.646 | >10 |
| 173 | >10 | >10 |
| 175 | 0.072 | 5.248 |
| 176 | 0.107 | 8.318 |
| 178 | 0.380 | >10 |
| 179 | 0.078 | >10 |
| 180 | 0.562 | 6.25 |

B) Demonstration of in vivo Efficacy

Aβ42 lowering agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ42 lowering agents can be administered in any standard form using any standard method. For example, but not limited to, Aβ42 lowering agents can be in the form of liquid, tablets or capsules that are taken orally or by injection. Aβ42 lowering agents can be administered at any dose that is sufficient to significantly reduce levels of Aβ42 in the blood, blood plasma, serum, cerebrospinal fluid (CSF), or brain.

To determine whether acute administration of an Aβ42 lowering agent would reduce Aβ42 levels in vivo, non-transgenic rodents, e.g. mice or rats were used. Alternatively, two to three month old Tg2576 mice expressing APP695 containing the "Swedish" variant can be used or a transgenic mouse model developed by Dr. Fred Van Leuven (K. U. Leuven, Belgium) and co-workers, with neuron-specific expression of a clinical mutant of the human amyloid precursor protein [V717I] (Moechars et al., 1999 J. Biol. Chem. 274, 6483). Young transgenic mice have high levels of Aβ in the brain but no detectable Aβ deposition. At approximately 6-8 months of age, the transgenic mice start to display spontaneous, progressive accumulation of β-amyloid (Aβ) in the brain, eventually resulting in amyloid plaques within the subiculum, hippocampus and cortex. Animals treated with the Aβ42 lowering agent were examined and compared to those untreated or treated with vehicle and brain levels of soluble Aβ42 and total Aβ would be quantitated by standard techniques, for example, using ELISA. Treatment periods varied from hours to days and were adjusted based on the results of the Aβ42 lowering once a time course of onset of effect could be established.

A typical protocol for measuring Aβ42 lowering in vivo is shown but it is only one of many variations that could be used to optimize the levels of detectable Aβ. For example, Aβ42 lowering compounds were formulated in 20% of Captisol® (a sulfobutyl ether of β-cyclodextrin) in water or 20% hydroxypropyl β cyclodextrin. The Aβ42 lowering agents were administered as a single oral dose or by any acceptable route of administration to overnight fasted animals. After four hours, the animals were sacrificed and Aβ42 levels were analysed.

Blood was collected by decapitation and exsanguinations in EDTA-treated collection tubes. Blood was centrifuged at 1900 g for 10 minutes at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains were resuspended in 10 volumes of 0.4% DEA (diethylamine)/50 mM NaCl pH 10 (for non-transgenic animals) or 0.1% 3-[3-cholamidopropyl)-dimethyl-ammonio]-1-propanesulfonate (CHAPS) in tris buffered saline (TBS) (for transgenic animals) containing protease inhibitors (Roche-11873580001 or 04693159001) per gram of tissue, e.g. for 0.158 g brain, add 1.58 ml of 0.4% DEA. All samples were sonicated for 30 seconds on ice at 20% power output (pulse mode). Homogenates were centrifuged at 221.300×g for 50 min. The resulting high speed supernatants were then transferred to fresh tubes and were optionally further purified before the next step. A portion of the supernatant was neutralized with 10% 0.5 M Tris-HCl and this was used to quantify Aβtotal.

The obtained supernatants were purified with Water Oasis HLB reverse phase columns (Waters Corp., Milford, Mass.) to remove non-specific immunoreactive material from the brain lysates prior subsequent Aβ detection. Using a vacuum manifold, all solutions were passed through the columns at a rate of approximately 1 ml per minute, so the vacuum pressure was adjusted accordingly throughout the procedure. Columns were preconditioned with 1 ml of 100% MeOH, before equilibration with 1 ml of H$_2$O. Non-neutralized brain lysates were loaded onto the columns. The loaded samples were then washed twice with the first wash performed with 1 ml of 5% MeOH, and the second wash with 1 ml of 30% MeOH. Finally, the Aβ was eluted from the columns and into 100×30 mm glass tubes, with a solution of 90% MeOH with 2% NH$_4$OH. The eluate was then transferred into 1.5 ml tubes and concentrated in a speed-vac concentrator on high heat for about 1.5-2 hours at 70° C. The concentrated Aβ was then resuspended in UltraCULTURE General Purpose Serum-Free Medium (Cambrex Corp., Walkersville, Md.) plus Protease Inhibitors added according to the manufacturers recommendation.

To quantify the amount of Aβ42 in the soluble fraction of the brain homogenates, commercially available Enzyme-Linked-Immunosorbent-Assay (ELISA) kits were used (e.g. Innotest® β-Amyloid$_{(1-42)}$, Innogenetics N.V., Ghent, Belgium).

The Aβ42 ELISA was performed using the plate provided with the kit only. Briefly, the standards (a dilution of synthetic Aβ-42) were prepared in 1.5 ml Eppendorf tube in Ultraculture, with final concentrations ranging from 25000 to 1.5 pg/ml. Samples, standards and blanks (60 μl) were added to the anti-Aβ42-coated plate (the capture antibody selectively recognizes the C-terminal end of the antigen). The plate was allowed to incubate overnight at 4° C. in order to allow formation of the antibody-amyloid complex. Following this incubation and subsequent wash steps a selective anti-Aβ-antibody conjugate (biotinylated detection antibody, e.g., biotinylated 4G8 (Covance Research Products, Dedham, Mass.) was added and incubated for a minimum of 1 hour in order to allow formation of the antibody-Amyloid-antibody-complex. After incubation and appropriate wash steps, a Streptavidine-Peroxidase-Conjugate was added, followed 50 minutes later by an addition of Quanta Blu fluorogenic peroxidase substrate according to the manufacturer's instructions (Pierce Corp., Rockford, Ill.). A kinetic reading was performed every 5 minutes for 30 minutes (excitation 320/emission 420). To quantify the amount of Aβtotal in the soluble fraction of the brain homogenates, samples and standards were added to JRF/rAβ/2-coated plate. The plate was allowed to incubate overnight at 4° C. in order to allow formation of the antibody-amyloid complex. The ELISA was then performed as for Aβ42 detection.

In this model at least 20% Aβ42 lowering compared to untreated animals would be advantageous.

The results are shown in table 13:

| Co. No. | Aβ42 (% Ctrl)_Mean | Aβtotal (% Ctrl)_Mean |
|---|---|---|
| 1 | 65 | 103 |
| 2 | 100 | 106 |
| 3 | 56 | 95 |
| 4 | 93 | 111 |
| 5 | 66 | 96 |
| 7 | 68 | 105 |
| 8 | 88 | 96 |
| 10 | 67 | 104 |
| 15 | 62 | 94 |
| 18 | 73 | 101 |
| 26 | 75 | 94 |
| 27 | 59 | 94 |
| 29 | 56 | 86 |
| 32 | 81 | 113 |
| 33 | 80 | 98 |
| 34 | 63 | 100 |
| 39 | 82 | 108 |
| 40 | 80 | 99 |
| 50 | 67 | 96 |
| 52 | 66 | 91 |
| 70 | 84 | 99 |
| 71 | 91 | 103 |
| 74 | 95 | 102 |
| 83 | 89 | 104 |
| 86 | 86 | 96 |
| 87 | 86 | 101 |
| 94 | 96 | 101 |
| 98 | 84 | 97 |
| 138 | 65 | 102 |

C. COMPOSITION EXAMPLES

"Active ingredient" (a.i.) as used throughout these examples relates to a compound of formula (I), including any stereochemically isomeric form thereof, a pharmaceutically acceptable salt thereof or a solvate thereof; in particular to any one of the exemplified compounds.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound of formula (I)

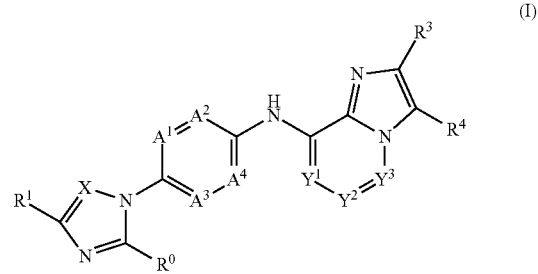

(I)

or a stereoisomeric form thereof, wherein
$R^0$ is hydrogen, or $C_{1-4}$alkyl;
$R^1$ is hydrogen, or $C_{1-4}$ alkyl;
X is $CR^7$ or N; wherein $R^7$ is hydrogen;
$A^1$ is $CR^2$ or N;
$A^2$ is $CR^8$ or N;
$A^3$ and $A^4$ each independently are CH or N;
provided that no more than two of $A^1$, $A^2$, $A^3$ and $A^4$ are N;
$R^2$ is hydrogen, halo or $C_{1-4}$alkyloxy;
$R^8$ is hydrogen or halo;
$R^3$ is hydrogen; $C_{1-6}$alkyl optionally substituted with one or more substituents each independently selected from the group consisting of hydroxyl, halo, morpholinyl, piperidinyl, pyrrolidinyl, tetrahydropyranyl, Ar, $C_{1-6}$alkyloxy, cyclo$C_{3-7}$alkyloxy, and cyclo$C_{3-7}$alkyl; carboxyl; $C_{2-4}$alkenyl; $NR^5R^6$-carbonyl; cyclo$C_{3-7}$ alkyl; Ar; tetrahydropyranyl; $C_{1-6}$alkylcarbonyl; $C_{1-6}$alkyloxycarbonyl; or Ar—O—$CH_2$—;
wherein each Ar independently is phenyl optionally substituted with one or more substituents each independently selected from the group consisting of halo, $C_{1-4}$alkyloxy, cyano, $NR^5R^6$, morpholinyl, $C_{1-4}$alkyl, and $C_{1-4}$alkyl substituted with one or more substituents each independently selected from the group consisting of halo, $C_{1-4}$alkyloxy, and $NR^5R^6$; benzimidazolyl optionally substituted with one or more substituents each independently selected from C$_{1-4}$alkyl; or pyridinyl optionally substituted with one or more substituents each independently selected from the group consisting of halo, C$_{1-4}$alkyloxy, cyano, C$_{1-4}$alkyl, and C$_{1-4}$alkyl substituted with one or more substituents each independently selected from halo;

each R$^5$ independently is hydrogen, C$_{1-4}$alkyl, C$_{1-6}$alkylcarbonyl, or C$_{1-4}$alkyloxy(CH$_2$CH$_2$O)$_n$—CH$_2$-carbonyl;

n is an integer selected from 1, 2, 3, 4, 5 or 6, each R$^6$ independently is hydrogen or C$_{1-4}$alkyl;

R$^4$ is hydrogen; cyano; halo; phenyl optionally substituted with one or more substituents each independently selected from the group consisting of halo and phenyl; phenylcarbonyl optionally substituted with one or more substituents each independently selected from halo; C$_{1-4}$alkyloxy; C$_{1-6}$alkyl optionally substituted with one or more substituents each independently selected from the group consisting of halo, NR$^5$R$^6$, C$_{1-4}$alkyloxy, hydroxyl, and formylamino;

Y$^1$ is CH;
Y$^2$ is CR$^9$;
Y$^3$ is CH;

R$^9$ is hydrogen; halo; tetrahydropyranyl; C$_{2-4}$alkenyl; phenyl optionally substituted with one or more substituents each independently selected from C$_{1-4}$alkyloxy; or C$_{1-4}$alkyl optionally substituted with one or more substituents each independently selected from halo;

or a pharmaceutically acceptable addition salt or a solvate thereof.

2. The compound according to claim 1 wherein the compound is a compound of formula (I-a)

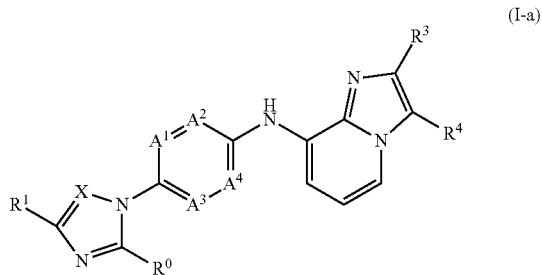

(I-a)

or a stereoisomeric form thereof, wherein
R$^0$ is hydrogen or C$_{1-4}$alkyl;
R$^1$ is hydrogen, or C$_{1-4}$alkyl;
X is CR$^7$ or N; wherein R$^7$ is hydrogen;
A$^1$ is CR$^2$ or N;
A$^2$, A$^3$ and A$^4$ each independently are CH or N;
provided that no more than two of A$^1$, A$^2$, A$^3$ and A$^4$ are N;
R$^2$ is hydrogen, halo or C$_{1-4}$alkyloxy;
R$^3$ is hydrogen; C$_{1-6}$alkyl optionally substituted with one or more substituents each independently selected from the group consisting of halo, morpholinyl, piperidinyl, pyrrolidinyl, Ar, C$_{1-6}$alkyloxy, cycloC$_{3-7}$alkyloxy, and cycloC$_{3-7}$alkyl; cycloC$_{3-7}$alkyl; tetrahydropyranyl; Ar; or Ar—O—CH$_2$—;
wherein each Ar independently is phenyl optionally substituted with one or more substituents each independently selected from the group consisting of halo, C$_{1-4}$alkyloxy, cyano, NR$^5$R$^6$, morpholinyl, C$_{1-4}$alkyl, and C$_{1-4}$alkyl substituted with one or more substituents each independently selected from halo; benzimidazolyl optionally substituted with one or more substituents each independently selected from C$_{1-4}$alkyl; or pyridinyl optionally substituted with one or more substituents each independently selected from the group consisting of halo, C$_{1-4}$alkyloxy, cyano, C$_{1-4}$alkyl, and C$_{1-4}$alkyl substituted with one or more substituents each independently selected from halo;

wherein each R$^5$ independently is hydrogen or C$_{1-4}$alkyl;

wherein each R$^6$ independently is hydrogen or C$_{1-4}$alkyl;

R$^4$ is hydrogen; cyano; halo; phenyl optionally substituted with one or more substituents each independently selected from the group consisting of halo and phenyl; phenylcarbonyl optionally substituted with one or more substituents each independently selected from halo; C$_{1-6}$alkyl optionally substituted with one or more substituents each independently selected from C$_{1-4}$alkyloxy; or C$_{1-4}$alkyl substituted with one or more substituents each independently selected from halo;

or a pharmaceutically acceptable addition salt or a solvate thereof.

3. The compound according to claim 1, or a stereoisomeric form thereof, wherein
R$^0$ is hydrogen or C$_{1-4}$alkyl;
R$^1$ is hydrogen or C$_{1-4}$alkyl;
X is CH or N;
R$^3$ is hydrogen; C$_{1-6}$alkyl optionally substituted with one or more substituents each independently selected from the group consisting of hydroxyl, halo, morpholinyl, piperidinyl, tetrahydropyranyl, Ar, C$_{1-6}$alkyloxy, and cycloC$_{3-7}$alkyl; carboxyl; C$_{2-4}$alkenyl; NR$^5$R$^6$-carbonyl; cycloC$_{3-7}$alkyl; Ar; tetrahydropyranyl; C$_{1-6}$alkylcarbonyl; C$_{1-6}$alkyloxycarbonyl; or Ar—O—CH$_2$—;
wherein each Ar independently is phenyl optionally substituted with one or more substituents each independently selected from the group consisting of halo, C$_{1-4}$alkyloxy, cyano, NR$^5$R$^6$, morpholinyl, C$_{1-4}$alkyl, and C$_{1-4}$alkyl substituted with one or more substituents each independently selected from the group consisting of halo and NR$^5$R$^6$; benzimidazolyl optionally substituted with one or more substituents each independently selected from C$_{1-4}$alkyl; or pyridinyl;

n is 2;

R$^4$ is hydrogen; cyano; halo; phenyl optionally substituted with one or more substituents each independently selected from the group consisting of halo and phenyl; phenylcarbonyl optionally substituted with one or more substituents each independently selected from halo; C$_{1-4}$alkyloxy; C$_{1-6}$alkyl optionally substituted with one or more substituents each independently selected from the group consisting of NR$^5$R$^6$, C$_{1-4}$alkyloxy, hydroxyl, and formylamino;

Y$^1$ is CH;
y$^2$ is CR$^9$;
Y$^3$ is CH;

R$^9$ is hydrogen; halo; tetrahydropyranyl; C$_{2-4}$alkenyl; phenyl optionally substituted with one or more substituents each independently selected from C$_{1-4}$alkyloxy; or C$_{1-4}$alkyl optionally substituted with one or more substituents each independently selected from halo;

or a pharmaceutically acceptable addition salt or a solvate thereof.

4. The compound according to claim 1, or a stereoisomeric form thereof, wherein
$R^0$ is hydrogen or $C_{1-4}$alkyl;
$R^1$ is hydrogen, or $C_{1-4}$alkyl;
X is $CR^7$ or N; wherein $R^7$ is hydrogen;
$A^1$ is $CR^2$ or N;
$A^2$, $A^3$ and $A^4$ each independently are CH or N;
provided that no more than two of $A^1$, $A^2$, $A^3$ and $A^4$ are N;
$R^2$ is hydrogen, halo or $C_{1-4}$alkyloxy;
$R^3$ is hydrogen; $C_{1-6}$alkyl optionally substituted with one substituent selected from the group consisting of morpholinyl, piperidinyl, Ar, $C_{1-6}$alkyloxy and cyclo$C_{3-7}$alkyl; tetrahydropyranyl; Ar; or Ar—O—$CH_2$—;
wherein each Ar independently is phenyl optionally substituted with one or more substituents each independently selected from the group consisting of halo, $C_{1-4}$alkyloxy, cyano, $NR^5R^6$, morpholinyl, $C_{1-4}$alkyl, and $C_{1-4}$alkyl substituted with one or more substituents each independently selected from halo; benzimidazolyl optionally substituted with one or more substituents each independently selected from $C_{1-4}$alkyl; or pyridinyl;
wherein each $R^5$ independently is $C_{1-4}$alkyl;
wherein each $R^6$ independently is $C_{1-4}$alkyl;
$R^4$ is hydrogen; cyano; halo; phenyl optionally substituted with one or more substituents each independently selected from the group consisting of halo and phenyl; phenylcarbonyl optionally substituted with one or more substituents each independently selected from halo; $C_{1-6}$alkyl optionally substituted with one or more substituents each independently selected from $C_{1-4}$alkyloxy;
or $C_{1-4}$alkyl substituted with one or more substituents each independently selected from halo;
or a pharmaceutically acceptable addition salt or a solvate thereof.

5. The compound according to claim 1, or a stereoisomeric form thereof, wherein
$R^3$ is phenyl;
$R^4$ is methyl; or
$R^3$ is phenyl substituted in a meta position and optionally further substituted in other positions;
$R^4$ is hydrogen or methyl; or
$R^3$ is phenyl substituted in an ortho position and optionally further substituted in other positions;
$R^4$ is hydrogen or methyl;
or a pharmaceutically acceptable addition salt or a solvate thereof.

6. The compound according to claim 1, or a stereoisomeric form thereof, wherein
$R^3$ is methyl substituted with one or more phenyl groups, wherein phenyl is optionally substituted with one or more substituents each independently selected from the group consisting of halo, $C_{1-4}$alkyloxy, cyano, $NR^5R^6$, morpholinyl,
$C_{1-4}$alkyl, and $C_{1-4}$alkyl substituted with one or more substituents each independently selected from halo;
$R^4$ is hydrogen;
or a pharmaceutically acceptable addition salt or a solvate thereof.

7. The compound according to claim 1, or a stereoisomeric form thereof, wherein
X is N;
or a pharmaceutically acceptable addition salt or a solvate thereof.

8. The compound according to claim 1, or a stereoisomeric form thereof, wherein
$R^0$ is hydrogen;
$R^1$ is $C_{1-4}$alkyl;
X is CH or N;
$A^1$ is $CR^2$;
$A^2$ is N;
$A^3$ and $A^4$ are CH;
$R^2$ is $C_{1-4}$alkyloxy;
$R^3$ is Ar; or $C_{1-4}$alkyl optionally substituted with one or more substituents each independently selected from halo;
wherein Ar is phenyl optionally substituted with one or more substituents each independently selected from halo;
$R^4$ is hydrogen or $C_{1-6}$alkyl;
or a pharmaceutically acceptable addition salt or a solvate thereof.

9. The compound according to any one of claims 1 and 3 to 8, wherein
$Y^1$ is CH;
$Y^2$ is CH; and
$Y^3$ is CH.

10. The compound according to claim 1, wherein the compound is 2-(2-chlorophenyl)-N-[6-methoxy-5-(3-methyl-1H-1,2,4-triazol-1-yl)-2-pyridinyl]-3-methyl-imidazo[1,2-a]pyridin-8-amine,
N-[6-methoxy-5-(4-methyl-1H-imidazol-1-yl)-2-pyridinyl]-2-(2,2,2-trifluoroethyl)-imidazo[1,2-a]pyridin-8-amine, or
N-[6-methoxy-5-(3-methyl-1H-1,2,4-triazol-1-yl)-2-pyridinyl]-2-(2,2,2-trifluoroethyl)-imidazo[1,2-a]pyridin-8-amine,
or any stereochemically isomeric form thereof or a pharmaceutically acceptable addition salt or a solvate thereof.

11. A pharmaceutical composition comprising a pharmaceutically acceptable carrier and, as active ingredient, a therapeutically effective amount of a compound as defined in any one of claims 1 to 10.

12. A method for the treatment of a disease or condition selected from Alzheimer's disease, traumatic brain injury, mild cognitive impairment, senility, dementia, dementia with Lewy bodies, cerebral amyloid angiopathy, multi-infarct dementia, Down's syndrome, dementia associated with Parkinson's disease and dementia associated with beta-amyloid comprising administering an effective amount of a compound as defined in claim 1 to a mammal in need thereof.

13. The method according to claim 12 wherein the disease is Alzheimer's disease.

* * * * *

UNITED STATES PATENT AND TRADEMARK OFFICE
CERTIFICATE OF CORRECTION

PATENT NO.        : 8,546,440 B2                                    Page 1 of 1
APPLICATION NO. : 13/133027
DATED             : October 1, 2013
INVENTOR(S)      : Gijsen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 50 days.

Signed and Sealed this
Fifteenth Day of September, 2015

Michelle K. Lee
*Director of the United States Patent and Trademark Office*